United States Patent
Lindholm et al.

(10) Patent No.: US 12,060,429 B2
(45) Date of Patent: *Aug. 13, 2024

(54) METHOD OF TREATING TYPE 1 INTERFERON (IFN)-MEDIATED DISEASE USING A SUBCUTANEOUS DOSING REGIMEN COMPRISING ANIFROLUMAB

(71) Applicant: ASTRAZENECA AB, Södertäje (SE)

(72) Inventors: Catharina Lindholm, Södertäje (SE); Yen Lin Chia, Wilmington, DE (US); Rajendra Tummala, Wilmington, DE (US); Lorin Roskos, Gaithersburg, MD (US); Joachim Almquist, Södertäje (SE); Thomas Rouse, Södertäje (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/305,235

(22) Filed: Apr. 21, 2023

(65) Prior Publication Data

US 2023/0365698 A1 Nov. 16, 2023

Related U.S. Application Data

(63) Continuation of application No. PCT/EP2022/060592, filed on Apr. 21, 2022.

(60) Provisional application No. 63/178,739, filed on Apr. 23, 2021, provisional application No. 63/245,285, filed on Sep. 17, 2021, provisional application No. 63/272,851, filed on Oct. 28, 2021.

(51) Int. Cl.
| | |
|---|---|
| *C07K 16/28* | (2006.01) |
| *A61K 39/00* | (2006.01) |
| *A61P 37/06* | (2006.01) |
| *A61P 43/00* | (2006.01) |

(52) U.S. Cl.
CPC .......... *C07K 16/2866* (2013.01); *A61P 37/06* (2018.01); *A61P 43/00* (2018.01); *A61K 2039/505* (2013.01); *A61K 2039/54* (2013.01); *A61K 2039/545* (2013.01); *C07K 2317/21* (2013.01); *C07K 2317/565* (2013.01); *C07K 2317/92* (2013.01)

(58) Field of Classification Search
CPC ............ C07K 16/2866; C07K 2317/21; C07K 2317/565; C07K 2317/92; A61P 37/06; A61K 2039/505; A61K 2039/54; A61K 2039/545

See application file for complete search history.

(56) References Cited

U.S. PATENT DOCUMENTS

| | | |
|---|---|---|
| 9,493,570 B2 | 11/2016 | Higgs et al. |
| 2006/0029601 A1 | 2/2006 | Cardarelli et al. |
| 2008/0113011 A1 | 5/2008 | Quay et al. |
| 2009/0186021 A1 | 7/2009 | Dingivan |
| 2011/0008365 A1 | 1/2011 | Coyle |
| 2011/0159513 A1 | 6/2011 | Schoeberl et al. |
| 2011/0183866 A1 | 7/2011 | Clarke et al. |
| 2011/0250168 A1 | 10/2011 | Nauwynck et al. |
| 2011/0287022 A1 | 11/2011 | Yao et al. |
| 2015/0158949 A1 | 6/2015 | Higgs et al. |
| 2017/0051066 A1 | 2/2017 | Depaz et al. |
| 2020/0399381 A1 | 12/2020 | Cao et al. |
| 2022/0340669 A1 | 10/2022 | Lindholm et al. |
| 2022/0348669 A1 | 11/2022 | Lindholm et al. |

FOREIGN PATENT DOCUMENTS

| | | |
|---|---|---|
| CN | 113521276 B | 4/2022 |
| WO | WO-2008070137 A1 | 6/2008 |
| WO | WO-2011028933 A1 | 3/2011 |
| WO | WO-2017031288 A1 | 2/2017 |
| WO | WO-2018023976 A1 | 2/2018 |
| WO | WO-2020165437 A1 | 8/2020 |
| WO | WO-2021094378 A1 | 5/2021 |
| WO | WO-2021239928 A2 | 12/2021 |
| WO | WO-2022074123 A1 | 4/2022 |
| WO | WO-2022106460 A2 | 5/2022 |

OTHER PUBLICATIONS

Tummala R, et al.(2018) Lupus Science & Medicine. 2018(5):e000252. (doi:10.1136/lupus-2017-000252).*

Goldberg, A., et al., "A Phase 1 Multicenter, Open-Label Study of MEDI-546, a Human Anti-Type I Interferon Receptor Monoclonal Antibody, in Adults with Scleroderma," 2012 ACRIARHP Annual Meeting, Abstract No. 692, MedImmune, Gaithersburg, MD, United States (2012).

Goldberg, A., et al., "Dose-escalation of human anti-interferon-a receptor monoclonal antibody MEDI-546 in subjects with systemic sclerosis: a phase 1, multicenter, open label study," Arthritis Research & Therapy, 16(1): R57, BioMed Central Ltd., United Kingdom (Feb. 2014).

Higgs, B.W., et al., "Patients with systemic lupus erythematosus, myositis, rheumatoid arthritis and scleroderma share activation of a common type I interferon pathway," Annals of the Rheumatic Diseases, 70: 2029-2036, BMJ Publishing Group (Nov. 2011).

Merrill, J., et al., "Safety public and clinical activity of sifalimumab, a fully human anti-interferon a monoclonal antibody, in systemic lupus erythematosus: a phase 1, multicentre, double-blind randomised study," Annals of the Rheumatic Diseases, 70(11): 1905-1913, BMJ Publishing Group, United Kingdom (Nov. 2011).

Wang, B., et al., "Pharmacogenomics and Translational Simulations to Bridge Indications for an Anti-Interferon-a Receptor Antibody," Clinical Pharmacology & Therapeutics, 93(6): 483-492 (Jun. 2013).

Furie, R.A., et al., "Type I interferon inhibitor anifrolumab in active systemic lupus erythematosus (TULIP-I): a randomized, controlled, phase 3 trial, " Lancet Rheumatology 1:e208-e219, Elsevier, Netherlands (Dec. 2019).

(Continued)

*Primary Examiner* — Robert S Landsman
(74) *Attorney, Agent, or Firm* — Sterne, Kessler, Goldstein & Fox P.L.L.C.

(57) ABSTRACT

The disclosure relates to methods and compositions for the treatment of type I IFN mediated disease. Specifically, the disclosure relates to a subcutaneous dose of a type I IFN receptor inhibitor.

10 Claims, 52 Drawing Sheets

Figure 1A:
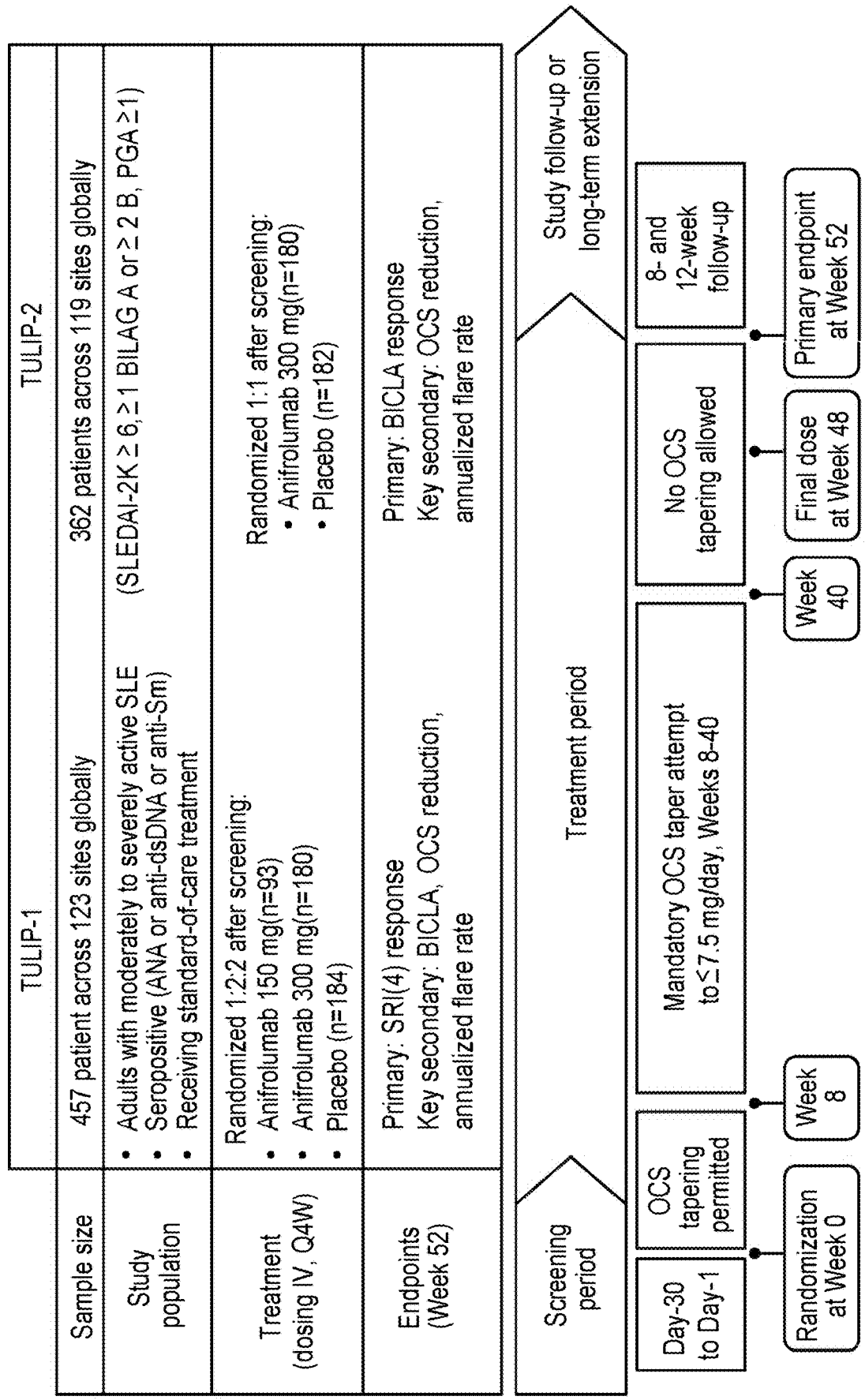

Specification includes a Sequence Listing.

(56) References Cited

OTHER PUBLICATIONS

Patel, J., et al., "An Update on the Pathogenesis of Cutaneous Lupus Erythematosus and Its Role in Clinical Practice," Current Rheumatology Reports 22:69, Springer, United States (Aug. 2020).

International Search Report and Written Opinion for International Application No. PCT/EP2021/077702, European Patent Office, Netherlands, mailed Feb. 28, 2022, 14 pages.

Morand, E., et al., "Efficacy and Safety of Anifrolumab in Patients with Moderate to Severe Systemic Lupus Erythematosus: Results of the Second Phase 3 Randomized Controlled Trial," ACR/ARP Annual Meeting: Abstract L17, pp. 1-6, United States (Oct. 2019). Accessed at https://acrabstracts.org/abstract/efficacy-and-safety-of-anifrolumab-in-patients-with-moderate-tp-severe-sysetmic-lupus-erythermatosus-results-of-the-second-phase-3-randomized-controlled-trial/.

Furie, R., et al., "Anifrolumab, an Anti-Interfeon-[alpha] Receptor Monoclonal Antibody, in Moderate-to-Severe Systemic Lupus Erythematosus: Anifrolumab in Moderate-to-Severe SLE," Arthritis & Rheumatology (Hoboken) 69:376-386, American College of Rheumatology, United States (Feb. 2017).

Furie, R., et al., "A Phase 3 Randomized Controlled Trial of Anifrolumab in Patients with Moderate to Severe Systemic Lupus Erythematosus," ACRIARP Annual Meeting: Abstract 1763, pp. 1-4, United States (Nov. 2019), Accessed at https://acrabstracts.org/abstract/a-phase-3-randomized-contorlled-trial-of-anifrolumab-in-patients-with-moderate-to-severe-systempic-lupus-erythematosus/.

International Search Report and Written Opinion for International Application No. PCT/EP2020/081770, European Patent Office, Netherlands, mailed Feb. 5, 2021, 15 pages.

Morand, E.F., et al., "Trial of Anifrolumab in Active Stsremic Lupus Erythematosus," New England Journal of Medicine 382:211-221, Massachusetts Medical Society, United States (Jan. 2020).

International Search Report and Written Opinion of International Application No. PCT/EP2022/060592, European Patent Office, Netherlands, mailed Aug. 31, 2022, 20 pages.

Viola, M., et al., " Subcutaneous delivery of monoclonal antibodies: How do we get there?," Journal of Controlled Release 286:301-314, Elsevier, Netherlands (Sep. 2018).

Saphnelo Prescribing Information, saphnelo.com accessed at https://www.saphnelo.com/, accessed on Nov. 18, 2022, 8 pages.

\* cited by examiner

Figure 18
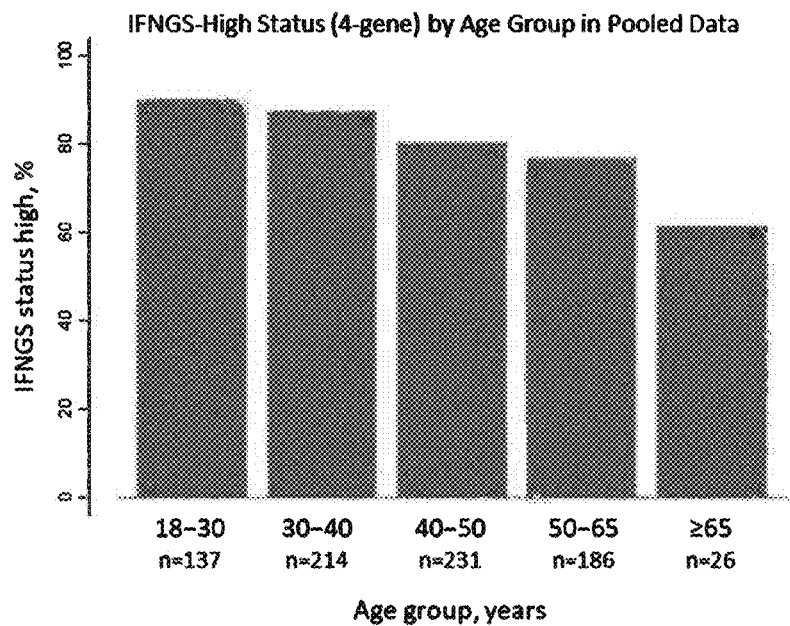
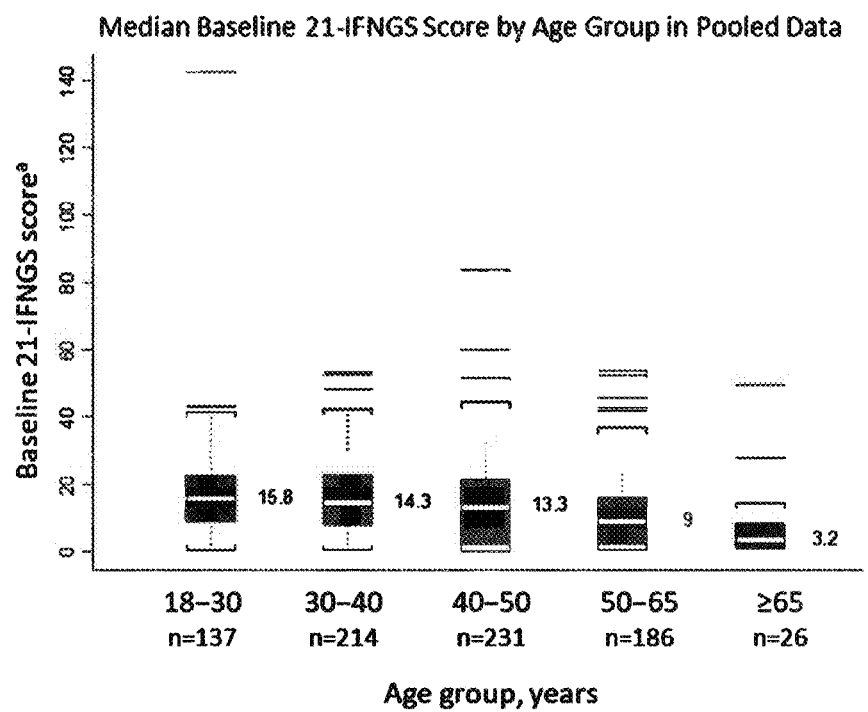

Figure 23
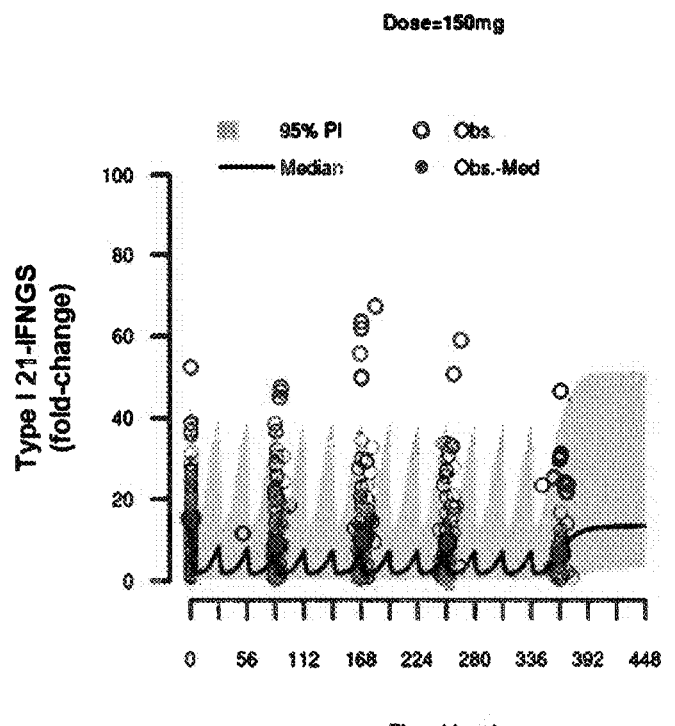
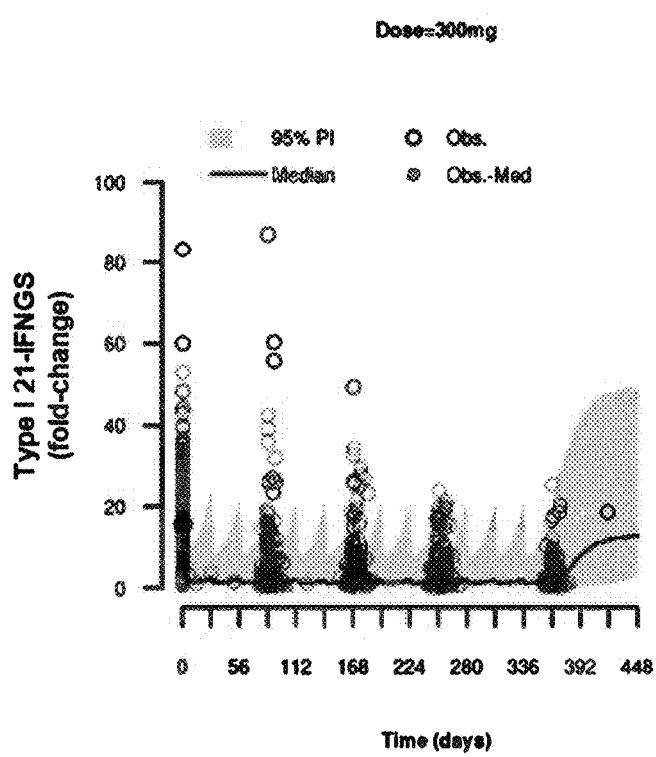

Figure 28

| Gene title | Gene symbol | Gene Probe ID |
|---|---|---|
| Interferon, alpha-inducible protein 27 | IFI27 | 202411 |
| Interferon, alpha-inducible protein 6 | IFI6 | 204415 |
| Radical S-adenosyl methionine domain containing 2 | RSAD2 | 213797 |
| Interferon-induced protein 44 | IFI44 | 214059 |
| Interferon-induced protein 44-like | IFI44L | 204439 |
| Ubiquitin specific peptidase 18 | USP18 | 219211 |
| Lymphocyte antigen 6 complex, locus E | LY6E | 202145 |
| 2,5-oligoadenylate synthetase 1, 40/46 kDa | OAS1 | 202869 |
| Sialic acid binding Ig-like lectin 1, sialoadhesin | SIGLEC1 | 44673 |
| ISG15 ubiquitin-like modifier | ISG15 | 205483 |
| Interferon-induced protein with tetratricopeptide repeats 1 | IFIT1 | 203153 |
| 2'-5'-oligoadenylate synthetase 3, 100 kDa | OAS3 | 218400 |
| Hect domain and RLD 5 | HERC5 | 219863 |
| Myxovirus (influenza virus) resistance 1 | MX1 | 202086 |
| Lysosomal-associated membrane protein 3 | LAMP3 | 205569 |
| Epithelial stromal interaction 1 (breast) | EPSTI1 | 227609 |
| Interferon-induced protein with tetratricopeptide repeats 3 | IFIT3 | 204747 |
| 2'-5'-oligoadenylate synthetase 2, 69/71 kDa | OAS2 | 204972 |
| Receptor (chemosensory) transporter protein 4 | RTP4 | 219684 |
| Phospholipid scramblase 1 | PLSCR1 | 241916 |
| DNA polymerase-transactivated protein 6 | DNAPTP6 | 241812 |

- Pooled data

OCS dosage ≥10 mg/day, p=0.01
Anti-RNP positive, p<0.001
Anti-SM positive, p<0.001
Anti-dsDNA positive, p<0.001
Complement 4 low, p<0.001
Complement 3 low, p<0.001
CLASI ≥ 10, p<0.001
SLEDAI-2k ≥ 10, p<0.001

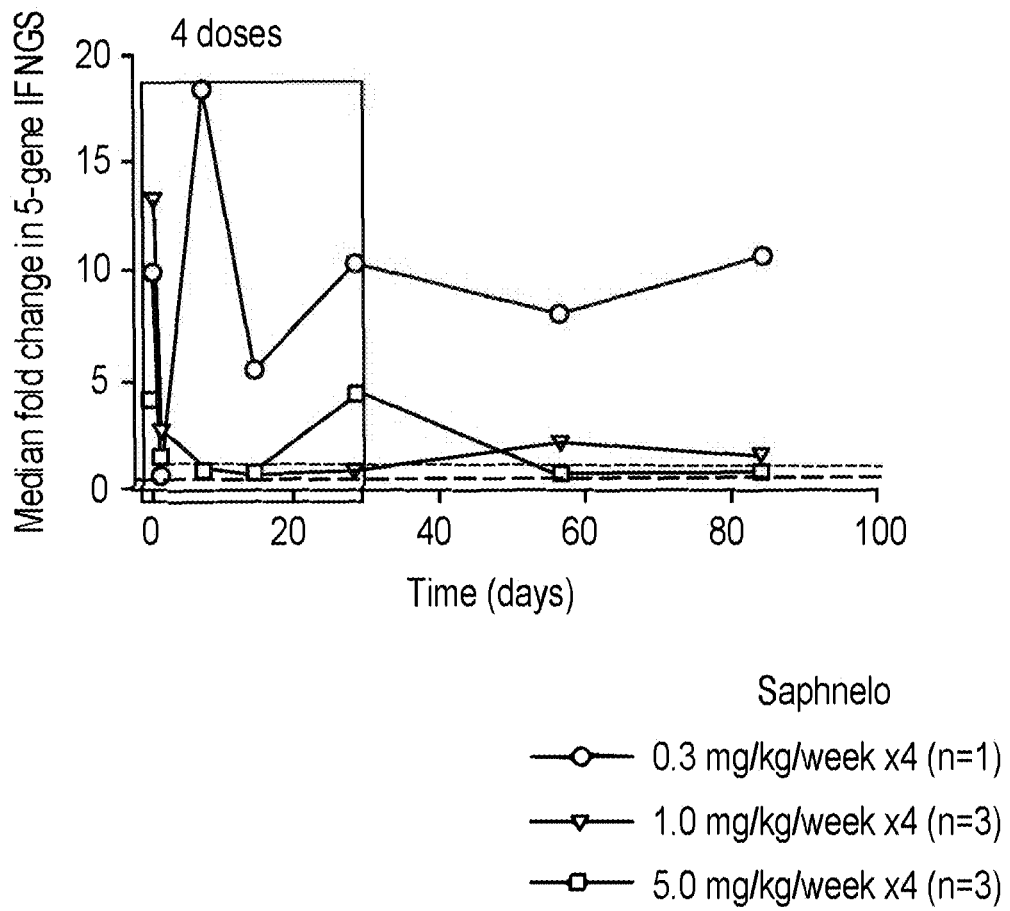

Modulation of Collagen Deposition

Improvement in Skin Scores

Figure 43
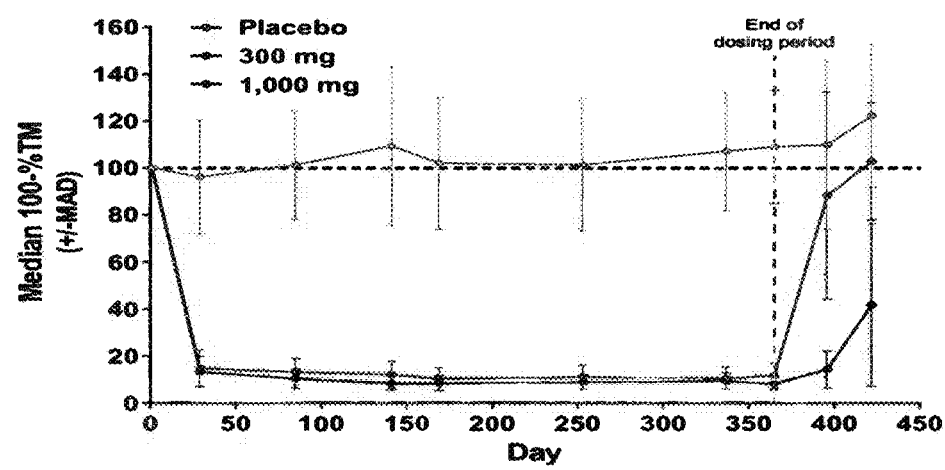
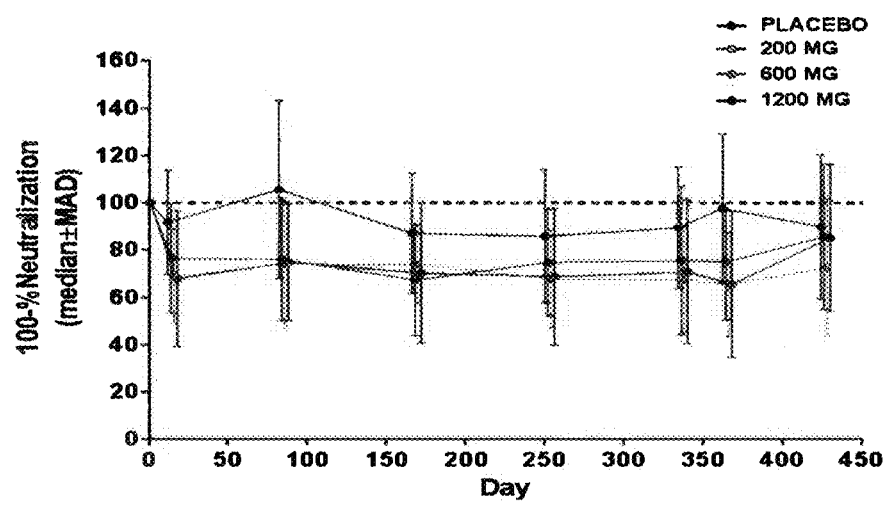

Figure 48

```
Consensus               EVQLVQSGAEVKKPGESLKISCKGSGYIFTNYWIAWVRQMPGKGLESMGIIYPGDSDIRYSPSFQGQVTISADKSITTAY    80
SEQ ID NO: 1_anifro-VH  EVQLVQSGAEVKKPGESLKISCKGSGYIFTNYWIAWVRQMPGKGLESMGIIYPGDSDIRYSPSFQGQVTISADKSITTAY    80
SEQ ID NO: 3_anifro-HCDR1 ----------------------------NYWIA-------------------------------------------------  50
SEQ ID NO: 4_anifro-HCDR2 ---------------------------------------------IIYPGDSDIRYSPSFQG-----------------   31
SEQ ID NO: 5_anifro-HCDR2 --------------------------------------------------------------------------------
SEQ ID NO: 10_anifro-HFc --------------------------------------------------------------------------------
SEQ ID NO: 11_anifro-HC EVQLVQSGAEVKKPGESLKISCKGSGYIFTNYWIAWVRQMPGKGLESMGIIYPGDSDIRYSPSFQGQVTISADKSITTAY    80
INN - anifro-HC         EVQLVQSGAEVKKPGESLKISCKGSGYIFTNYWIAWVRQMPGKGLESMGIIYPGDSDIRYSPSFQGQVTISADKSITTAY    80

Consensus               LQWSSLKASDTAMYYCARHDIEGFDYWGRGTLVTVSSASTKGPSVFPLAPSSKSTSGGTAALGCLVKDYFPEPVTVSWNS   160
SEQ ID NO: 1_anifro-VH  LQWSSLKASDTAMYYCARHDIEGFDYWGRGTLVTVSS-------------------------------------------   160
SEQ ID NO: 3_anifro-HCDR1 --------------------------------------------------------------------------------  130
SEQ ID NO: 4_anifro-HCDR2 --------------------------------------------------------------------------------  111
SEQ ID NO: 5_anifro-HCDR2 -----------------HDIEGFDY-------------------------------------------------------   62
SEQ ID NO: 10_anifro-HFc -------------------------------ASTKGPSVFPLAPSSKSTSGGTAALGCLVKDYFPEPVTVSWNS         43
SEQ ID NO: 11_anifro-HC LQWSSLKASDTAMYYCARHDIEGFDYWGRGTLVTVSSASTKGPSVFPLAPSSKSTSGGTAALGCLVKDYFPEPVTVSWNS   160
INN - anifro-HC         LQWSSLKASDTAMYYCARHDIEGFDYWGRGTLVTVSSASTKGPSVFPLAPSSKSTSGGTAALGCLVKDYFPEPVTVSWNS   160

Consensus               GALTSGVHTFPAVLQSSGLYSLSSVVTVPSSSLGTQTYICNVNHKPSNTKVDKRVEPKSCDKTHTCPPCPAPEFEGGPSV   240
SEQ ID NO: 1_anifro-VH  --------------------------------------------------------------------------------  240
SEQ ID NO: 3_anifro-HCDR1 --------------------------------------------------------------------------------  210
SEQ ID NO: 4_anifro-HCDR2 --------------------------------------------------------------------------------  191
SEQ ID NO: 5_anifro-HCDR2 --------------------------------------------------------------------------------  142
SEQ ID NO: 10_anifro-HFc GALTSGVHTFPAVLQSSGLYSLSSVVTVPSSSLGTQTYICNVNHKPSNTKVDKRVEPKSCDKTHTCPPCPAPEFEGGPSV   123
SEQ ID NO: 11_anifro-HC GALTSGVHTFPAVLQSSGLYSLSSVVTVPSSSLGTQTYICNVNHKPSNTKVDKRVEPKSCDKTHTCPPCPAPEFEGGPSV   240
INN - anifro-HC         GALTSGVHTFPAVLQSSGLYSLSSVVTVPSSSLGTQTYICNVNHKPSNTKVDKRVEPKSCDKTHTCPPCPAPEFEGGPSV   240

Consensus               FLFPPKPKDTLMISRTPEVTCVVVDVSHEDPEVKFNWYVDGVEVHNAKTKPREEQYNSTYRVVSVLTVLHQDWLNGKEYK   320
SEQ ID NO: 1_anifro-VH  --------------------------------------------------------------------------------  320
SEQ ID NO: 3_anifro-HCDR1 --------------------------------------------------------------------------------  290
SEQ ID NO: 4_anifro-HCDR2 --------------------------------------------------------------------------------  271
SEQ ID NO: 5_anifro-HCDR2 --------------------------------------------------------------------------------  222
SEQ ID NO: 10_anifro-HFc FLFPPKPKDTLMISRTPEVTCVVVDVSHEDPEVKFNWYVDGVEVHNAKTKPREEQYNSTYRVVSVLTVLHQDWLNGKEYK   203
SEQ ID NO: 11_anifro-HC FLFPPKPKDTLMISRTPEVTCVVVDVSHEDPEVKFNWYVDGVEVHNAKTKPREEQYNSTYRVVSVLTVLHQDWLNGKEYK   320
INN - anifro-HC         FLFPPKPKDTLMISRTPEVTCVVVDVSHEDPEVKFNWYVDGVEVHNAKTKPREEQYNSTYRVVSVLTVLHQDWLNGKEYK   320

Consensus               CKVSNKALPASIEKTISKAKGQPREPQVYTLPPSREEMTKNQVSLTCLVKGFYPSDIAVEWESNGQPENNYKTTPPVLDS   400
SEQ ID NO: 1_anifro-VH  --------------------------------------------------------------------------------  400
SEQ ID NO: 3_anifro-HCDR1 --------------------------------------------------------------------------------  370
SEQ ID NO: 4_anifro-HCDR2 --------------------------------------------------------------------------------  351
SEQ ID NO: 5_anifro-HCDR2 --------------------------------------------------------------------------------  302
SEQ ID NO: 10_anifro-HFc CKVSNKALPASIEKTISKAKGQPREPQVYTLPPSREEMTKNQVSLTCLVKGFYPSDIAVEWESNGQPENNYKTTPPVLDS   283
SEQ ID NO: 11_anifro-HC CKVSNKALPASIEKTISKAKGQPREPQVYTLPPSREEMTKNQVSLTCLVKGFYPSDIAVEWESNGQPENNYKTTPPVLDS   400
INN - anifro-HC         CKVSNKALPASIEKTISKAKGQPREPQVYTLPPSREEMTKNQVSLTCLVKGFYPSDIAVEWESNGQPENNYKTTPPVLDS   400

Consensus               DGSFFLYSKLTVDKSRWQQGNVFSCSVMHEALHNHYTQKSLSLSPGK                                    447
SEQ ID NO: 1_anifro-VH  -----------------------------------------------                                    117
SEQ ID NO: 3_anifro-HCDR1 -----------------------------------------------                                      5
SEQ ID NO: 4_anifro-HCDR2 -----------------------------------------------                                     17
SEQ ID NO: 5_anifro-HCDR2 -----------------------------------------------                                      8
SEQ ID NO: 10_anifro-HFc DGSFFLYSKLTVDKSRWQQGNVFSCSVMHEALHNHYTQKSLSLSPGK                                    330
SEQ ID NO: 11_anifro-HC DGSFFLYSKLTVDKSRWQQGNVFSCSVMHEALHNHYTQKSLSLSPGK                                    447
INN - anifro-HC         DGSFFLYSKLTVDKSRWQQGNVFSCSVMHEALHNHYTQKSLSLSPGK                                    447
```

Figure 49

```
Consensus              EIVLTQSPGTLSLSPGERATLSCRASQSVSSSFFAWYQQKPGQAPRLLIYGASSRATGIPDRLSGSGSGTDFTLTITRLE
SEQ ID NO: 2_anifro-VK     EIVLTQSPGTLSLSPGERATLSCRASQSVSSSFFAWYQQKPGQAPRLLIYGASSRATGIPDRLSGSGSGTDFTLTITRLE   80
SEQ ID NO: 6_anifro-LCDR1  ----------------------------RASQSVSSSFFA---------------------------------------   80
SEQ ID NO: 7_anifro-LCDR2  ---------------------------------------------------GASSRAT---------------------   57
SEQ ID NO: 8_anifro-LCDR3  -------------------------------------------------------------------------------   30
SEQ ID NO: 09_anifro-LFc   -------------------------------------------------------------------------------
SEQ ID NO: 12_anifro-LC    EIVLTQSPGTLSLSPGERATLSCRASQSVSSSFFAWYQQKPGQAPRLLIYGASSRATGIPDRLSGSGSGTDFTLTITRLE   80

Consensus              PEDFAVYYCQQYDSSAITFGQGTRLEIKRTVAAPSVFIFPPSDEQLKSGTASVVCLLNNFYPREAKVQWKVDNALQSGNS
SEQ ID NO: 2_anifro-VK     PEDFAVYYCQQYDSSAITFGQGTRLEIK---------------------------------------------------  160
SEQ ID NO: 6_anifro-LCDR1  -------------------------------------------------------------------------------  160
SEQ ID NO: 7_anifro-LCDR2  -------------------------------------------------------------------------------  137
SEQ ID NO: 8_anifro-LCDR3  ----QQYDSSAIT------------------------------------------------------------------  110
SEQ ID NO: 09_anifro-LFc   ---------------------RTVAAPSVFIFPPSDEQLKSGTASVVCLLNNFYPREAKVQWKVDNALQSGNS         71
SEQ ID NO: 12_anifro-LC    PEDFAVYYCQQYDSSAITFGQGTRLEIKRTVAAPSVFIFPPSDEQLKSGTASVVCLLNNFYPREAKVQWKVDNALQSGNS   52
                                                                                                             160

Consensus              QESVTEQDSKDSTYSLSSTLTLSKADYEKHKVYACEVTHQGLSSPVTKSFNRGEC
SEQ ID NO: 2_anifro-VK     ------------------------------------------------------  215
SEQ ID NO: 6_anifro-LCDR1  ------------------------------------------------------  108
SEQ ID NO: 7_anifro-LCDR2  ------------------------------------------------------   12
SEQ ID NO: 8_anifro-LCDR3  ------------------------------------------------------    7
SEQ ID NO: 09_anifro-LFc   QESVTEQDSKDSTYSLSSTLTLSKADYEKHKVYACEVTHQGLSSPVTKSFNRGEC    9
SEQ ID NO: 12_anifro-LC    QESVTEQDSKDSTYSLSSTLTLSKADYEKHKVYACEVTHQGLSSPVTKSFNRGEC  107
                                                                                  215
```

METHOD OF TREATING TYPE 1 INTERFERON (IFN)-MEDIATED DISEASE USING A SUBCUTANEOUS DOSING REGIMEN COMPRISING ANIFROLUMAB

CROSS REFERENCE TO RELATED APPLICATIONS

This patent application is a continuation of International Application No. PCT/EP2022/060592, filed on Apr. 21, 2022, which claims the benefit of U.S. Provisional Patent Application No. 63/178,739, filed Apr. 23, 2021, U.S. Provisional Patent Application No. 63/245,285, filed Sep. 17, 2021, and U.S. Provisional Patent Application Ser. No. 63/272,851, filed Oct. 28, 2021. The entire contents of the above-referenced patent applications are incorporated herein by reference.

REFERENCE TO A SEQUENCE LISTING SUBMITTED ELECTRONICALLY VIA EFS-WEB

The content of the electronically submitted sequence listing in ASCII text file (Name: 2943_2640003_Sequence-Listing_ST26; Size: 27,899 bytes; and Date of Creation: Apr. 21, 2023) is herein incorporated by reference in its entirety.

1. BACKGROUND

To date, clinical studies of the type I IFN receptor (IFNAR1) inhibitor anifrolumab have focused mainly on treatment of type 1 interferon-mediated diseases such as systemic lupus erythematosus (SLE) by intravenous (IV) administration of the antibody. However, intravenous administration requires the patient to visit a hospital or clinic in order that the procedure can be performed by a medical professional. Intravenous administration is therefore inconvenient to the patient and places a burden on both the patient and the health care system.

1.1. Systemic Lupus Erythematosus (SLE)

Systemic lupus erythematosus (SLE) is a chronic, multisystemic, disabling autoimmune rheumatic disease of unknown etiology. There is substantial unmet medical need in the treatment of SLE, particularly in patients with moderate or severe disease. Long-term prognosis remains inadequate for many patients. There has been only one new treatment (belimumab) for SLE has been approved by the United States (US) Food and Drug Administration (FDA) and European Medicines Agency (EMA) in the approximately 60 years since hydroxychloroquine was approved for use in discoid lupus and SLE. Many agents currently used to treat SLE, such as azathioprine, cyclophosphamide, and mycophenolate mofetil/mycophenolic acid, have not been approved for the disease. Furthermore, these drugs all have well-documented safety issues and are not effective in all patients for all manifestations of lupus. Glucocorticoids remain the mainstay treatment with doses varying depending on severity of disease manifestation. There is no "safe" dose of oral glucocorticoids in relation to the risk for development of glucocorticoid-induced damage such as cataracts, osteoporosis and coronary artery disease, and whereas higher glucocorticoid-exposure has been shown to be associated with increased overall damage accrual, fairly low to moderate doses can also be related to increased damage.

Clinical manifestations of SLE include, but are not limited to, constitutional symptoms such as fatigue and fever, alopecia, rashes, serositis, arthritis, nephritis, vasculitis, lymphadenopathy, splenomegaly, hemolytic anemia, cognitive dysfunction and other nervous system involvement. These disease manifestations cause a significant burden of illness and can lead to permanent organ damage, reduced physical function, loss of employment, and greater health-related quality of life (QoL) impairments. Increased hospitalizations and side effects of medications including chronic glucocorticoids at high doses and other immunosuppressive treatments critically add to disease burden in SLE. All of the therapies currently used for the treatment of SLE have well known adverse effect profiles and there is a medical need to identify new targeted therapies, particularly agents that may reduce the requirement for glucocorticoids and cytotoxic agents.

1.2. Subcutaneous Administration

Compared to the intravenous route of administration, subcutaneous administration has the advantage of enabling home administration and thus of reducing the frequency of hospital visits by the patient. Subcutaneous (SC) administration is therefore particular advantageous during a global pandemic such as the SARS-Cov2 pandemic as it avoids the need for potentially immunologically vulnerable patients to put themselves at risk of SARS-Cov2 infection by visiting hospital.

Despite the advantages of subcutaneous administration compared to intravenous injection, switching from intravenous to subcutaneous administration is not straightforward. Conversion to subcutaneous dosing may sometimes require development of a new formulation and the consideration of factors such as differences in the bioavailability pharmacokinetic properties and immunogenicity of subcutaneous versus intravenous administration [1].

The pharmacokinetic profiles of subcutaneous and intravenous formulations differ. Infusion of a monoclonal antibody directly into the bloodstream usually results in immediate maximum serum concentrations ($C_{max}$). By contrast, the pharmacokinetic (PK) profile of subcutaneously injected therapeutic proteins is typically characterized by a delayed absorption rate and $C_{max}$ levels below those achieved with intravenous dosing [2]. Furthermore, subcutaneous administration results in incomplete bioavailability of the injected molecule, which can range widely from 50 to 80% for mAbs [2]. Incomplete bioavailability typically results in the need for a higher dose for subcutaneous administration than for intravenous infusions. Predicting the PK of a therapeutic administered SC is therefore challenging [2].

Predicting a safe and therapeutically effective subcutaneous dose based on intravenous dose is particularly complicated in heterogenous autoimmune diseases such as lupus (e.g. SLE). The difficulty of using data from intravenous administration of a biologic to predict a safe and effective subcutaneous dose for the treatment of SLE is demonstrated by the previous failed attempts to do so. In a SLE phase I study, for example, a single dose of tabalumab, an anti-BAFF monoclonal antibody, was administered intravenously to a total of 5 patients with SLE [3]. In the subsequent phase III ILLUMINATE™ trials (NCT01205438 and NCT01196091), subcutaneous dosing was selected instead or the intravenous route [4,5]. In the phase I trial, SLE patients received single doses of intravenous tabalumab, either 0.125 or 2.0 mg/kg [3]. In the phase III ILLUMINATE™ trials, subjects were given an initial subcutaneous loading dose of 240 mg, followed by 120 mg subcutaneously either biweekly or monthly. The primary endpoint, SRI-5 response, was not met for either dose group. The investigators commented that a possible reason for the failure of the trials was the selection of an inappropriate SC dose [4] and that, even following the trial, the optimal SC dose was unknown [5].

1.3. Anifrolumab

Anifrolumab is a human immunoglobulin G1 kappa (IgG1$_K$) monoclonal antibody (mAb) directed against subunit 1 of the type I interferon receptor (IFNAR1). Despite the advantages of subcutaneous versus intravenous administration, a subcutaneous dose of anifrolumab that is safe and effective in SLE patients had not previously been determined.

The present invention solves one or more of the above-mentioned problems, by providing a dose of an IFNAR1 inhibitor (e.g. anifrolumab) for subcutaneous administration.

2. SUMMARY

The present invention relates to a subcutaneous dose of a type I IFN receptor (IFNAR1, also referred to as IFNAR) inhibitor. The present invention also relates to a subcutaneous dose of IFNAR1 inhibitor for use in method of treating a type I IFN-mediated disease such as lupus (e.g. SLE) in a subject. The invention is supported by data showing that a common type I IFN gene signature (IFNGS) is elevated in subjects suffering from type I IFN-mediated disease, including lupus, myositis, scleroderma and Sjogren's syndrome, that this IFNGS is associated with severity of disease, and identification of a safe and effective dose of an IFNAR1 inhibitor that neutralizes the IFNGS.

The invention is supported inter alia by efficacy, safety and PK data relating a IFNAR1 inhibitor (anifrolumab) from 2 phase 3, multicenter, multinational, randomized, double-blind, placebo-controlled clinical trials in SLE patients (NCT02446899 and NCT02962960), a phase 2, multinational, multicenter, randomized, double-blind, placebo controlled, parallel-group clinical trial in SLE patients (NCT02962960), a phase I, Randomized, Placebo-Controlled, Double-Blind clinical trial in health subjects (NCT02601625), a phase II study to characterize the pharmacokinetics, pharmacodynamics, and safety of anifrolumab in adult type I Interferon test high SLE Subjects (NCT02962960), data analyses of which are presented herein for the first time. The present inventors used innovative data modelling to identify the optimal subcutaneous dose of the IFNAR1 inhibitor that would provide equivalent safety and efficacy to the intravenous dose.

3. BRIEF DESCRIPTION OF FIGURES

Figure 1B:
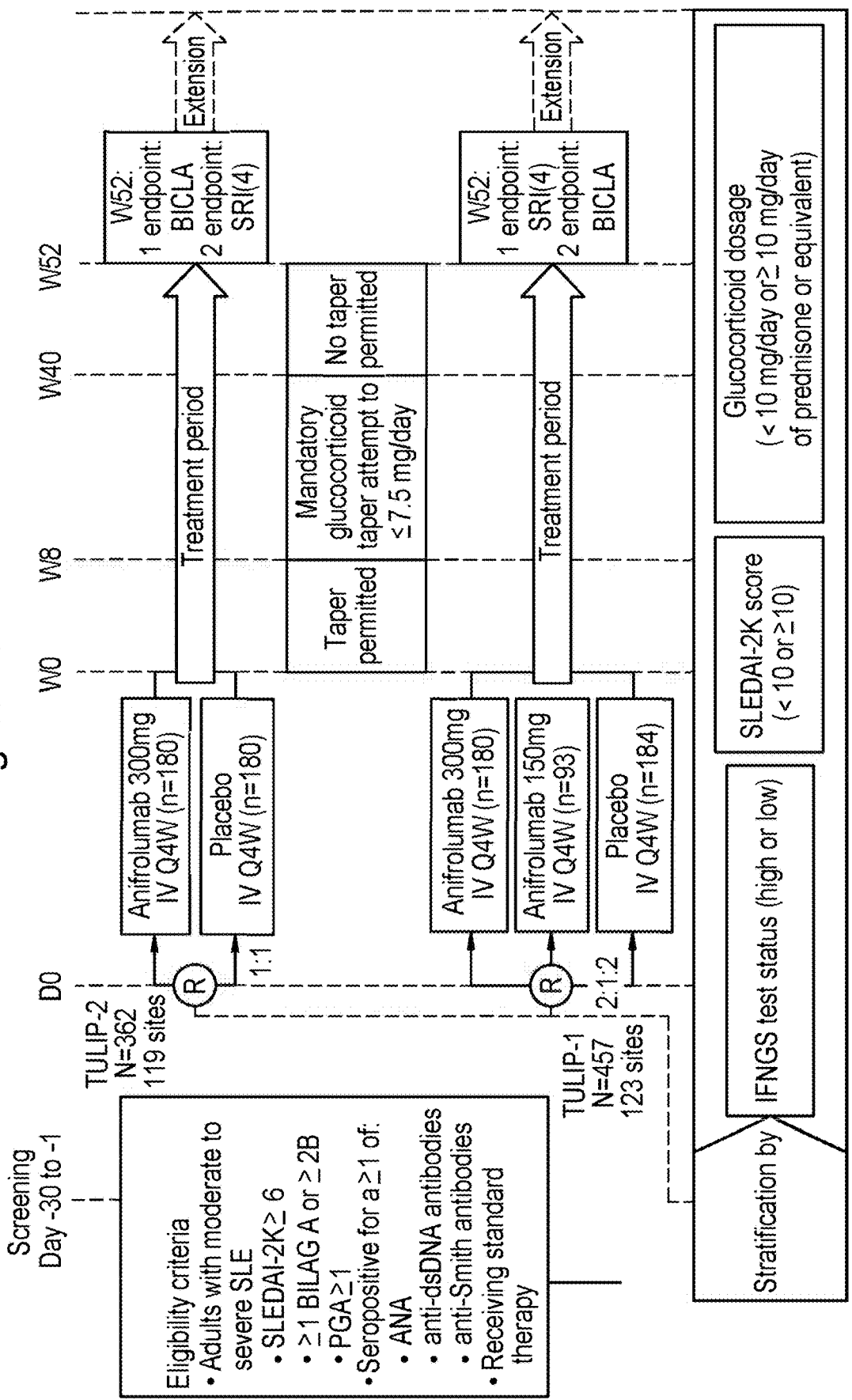

FIG. 1A-1B: TULIP-1 and TULIP-2 study design

ACR: American College of Rheumatology; ANA: antinuclear antibodies; anti-dsDNA: anti-double-stranded DNA; anti-Sm: anti-Smith antibodies; BICLA: BILAG-based Composite Lupus Assessment; BILAG: British Isles Lupus Assessment Group; IFNGS: interferon gene signature; IV: intravenous; OCS: oral corticosteroid; PGA: Physician's Global Assessment; Q4W: every 4 weeks; SLE: systemic lupus erythematosus; SLEDAI-2K: SLE Disease Activity Index 2000; SRI(4): SLE Responder Index. [a]Eligible patients fulfilled ACR classification for SLE; [b]Patients were stratified by IFNGS status, SLEDAI-2K score, and OCS dosage; [c]For patients with baseline OCS of prednisone ≥10 mg/day or equivalent.

Figure 2:
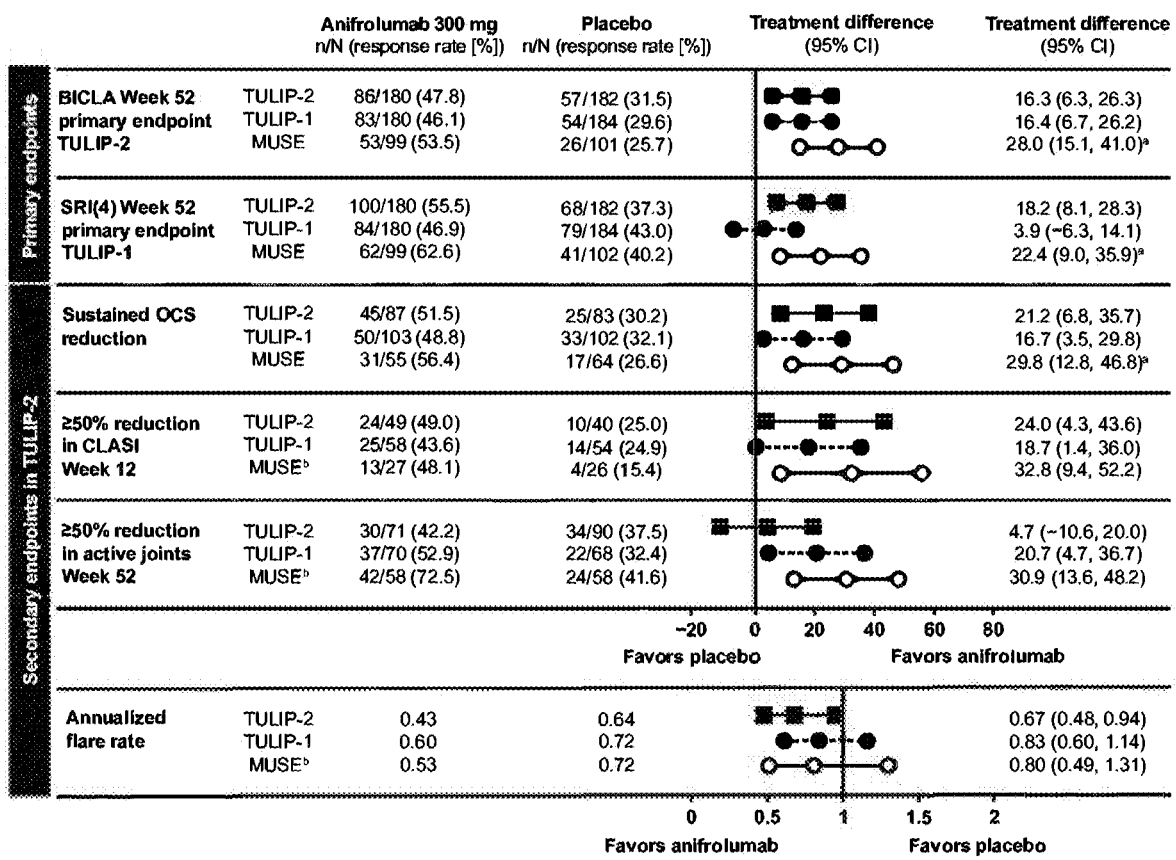

FIG. 2: TULIP-1 and TULIP-2 efficacy results

Overall efficacy results for TULIP-1, TULIP-2, and MUSE. BICLA: BILAG-based Composite Lupus Assessment; BILAG: British Isles Lupus Assessment Group; CI: confidence interval; CLASI: Cutaneous Lupus Erythematosus Disease Area and Severity Index; IFNGS: interferon gene signature; OCS: oral corticosteroid; SRI(4): SLE Responder Index. Analytic methods and definitions differ across trials. [a]Published data expressed as odds ratio; [b]Previously unpublished data.

Figure 3A:
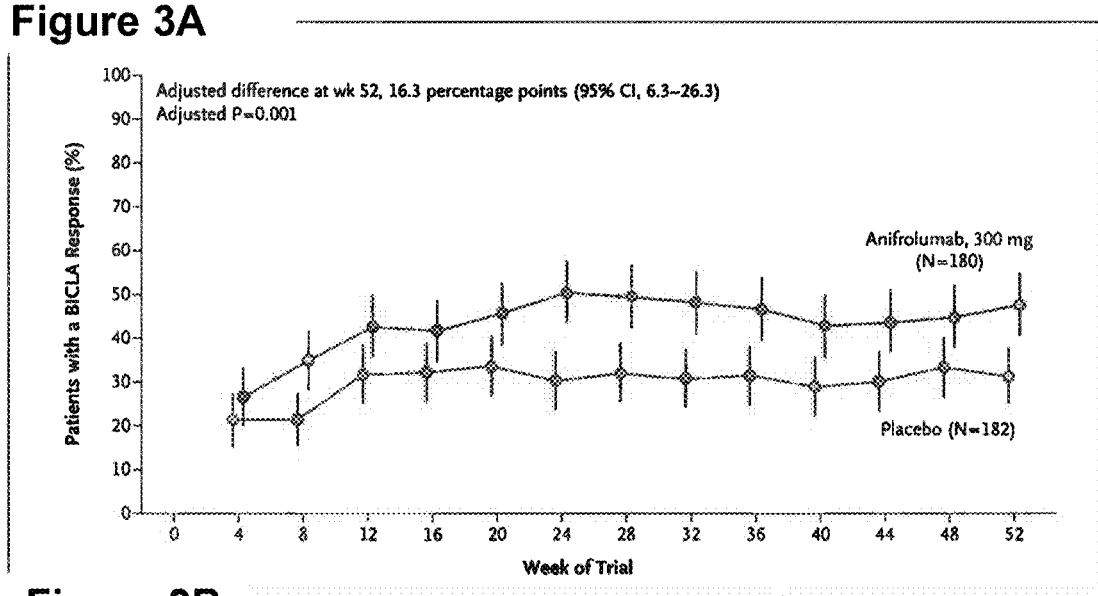
Figure 3B:
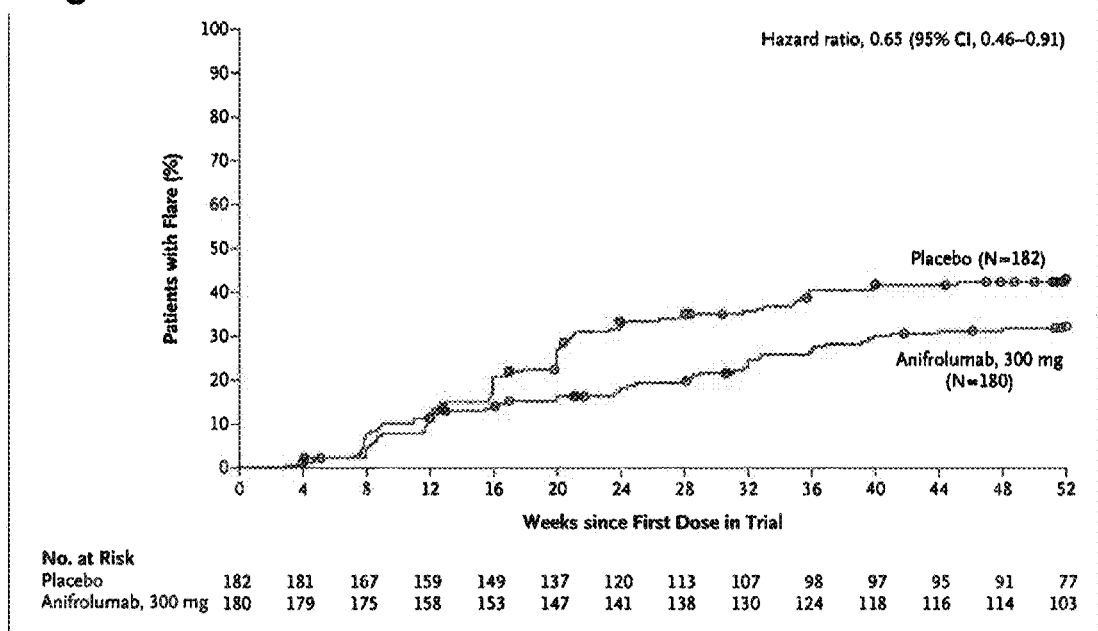

FIG. 3A-3B: Study 05, BICLA Responses over Time and Time to First Flare

FIG. 3A shows the percentage of patients with a British Isles Lupus Assessment Group (BILAG)-based Composite Lupus Assessment (BICLA) response; the vertical bars indicate 95% confidence intervals (CIs). FIG. 3B shows the time to first flare, with flare defined as at least one new A item on the BILAG 2004 index (BILAG-2004) or at least two new BILAG-2004 B items as compared with the previous visit. BILAG-2004 is an assessment of 97 clinical and laboratory variables covering nine organ systems, with scores ranging from A (severe) to E (never involved) for each organ system. The open black circles in this panel indicate censored data. Time to first flare was evaluated with the use of a Cox proportional-hazards model but was not adjusted for multiple comparisons, and no inferences can be drawn from this result.

Figure 4:
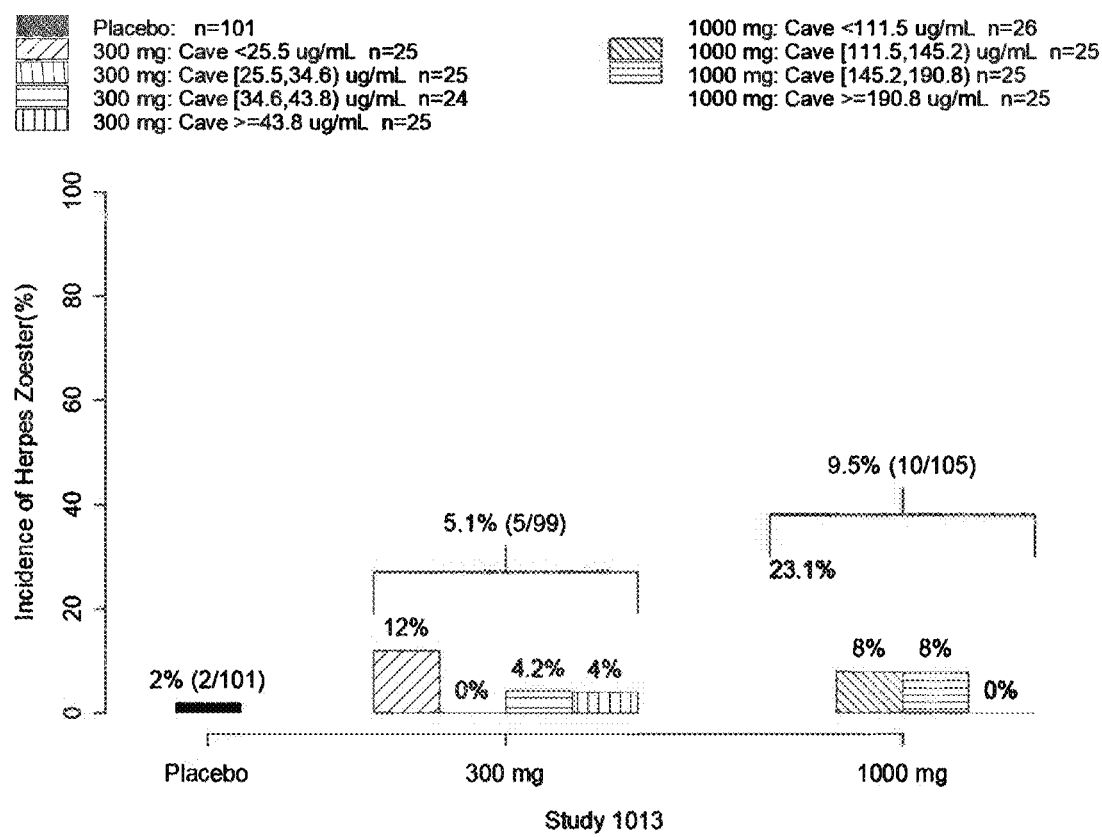

FIG. 4: Average anifrolumab concentration versus herpes zoster incidence

The incidence of Herpes Zoster (%) in patients in the Study 1013 receiving placebo, 300 mg IV anifrolumab or 1000 mg IV anifrolumab.

Figure 5A:
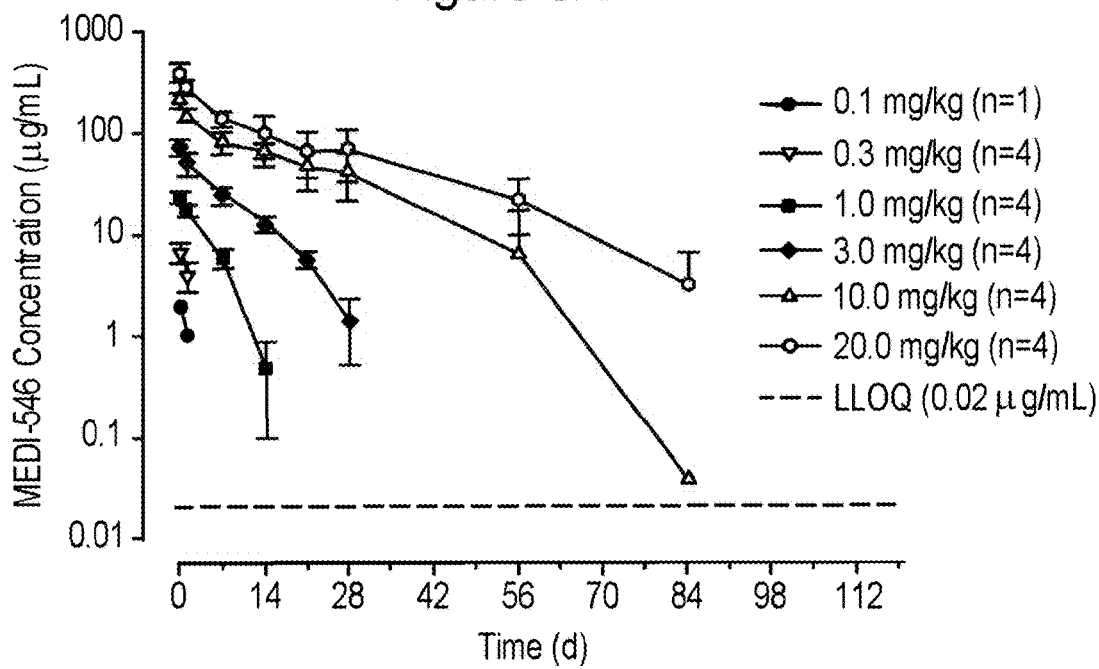
Figure 5B:
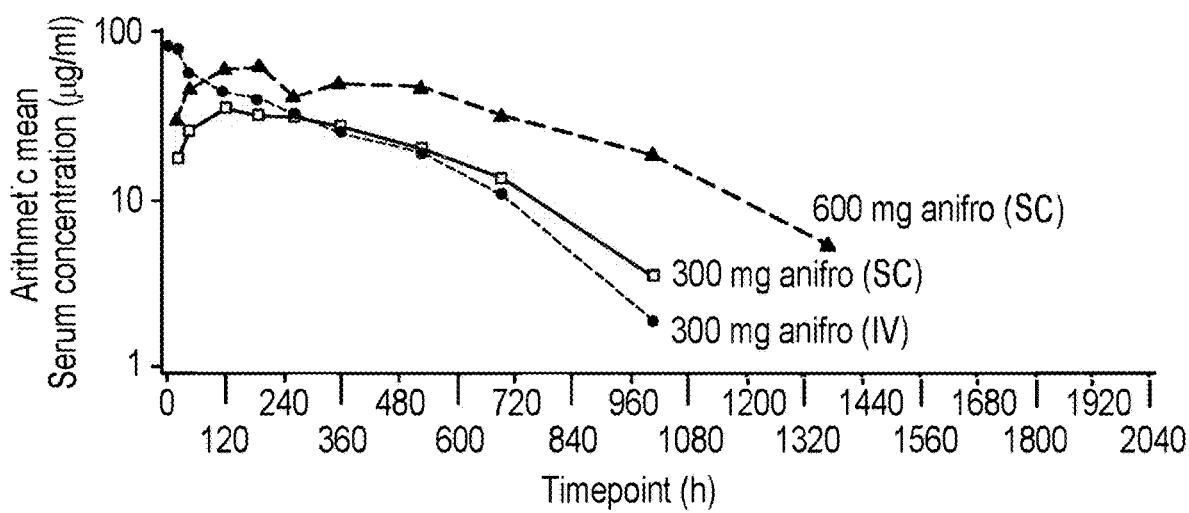

FIG. 5A-5B: Mean anifrolumab serum concentration-time profiles

FIG. 5A: Study MI-CP180 in SSc—Mean anifrolumab serum concentration-time profiles following a single IV dose. Data represent +/−SD. Mean data below LLOQ are not plotted. IV, intravenous; LLOQ, lower limit of quantification; MEDI 546, anifrolumab; n, number of patients in a subgroup; SSc, systemic sclerosis. FIG. 5B: Study 06 in healthy volunteers—Mean anifrolumab serum concentration-time profiles following a single SC and IV dose. Samples with actual collection time deviating from nominal collection time by >10% were excluded from the mean. IV, intravenous; N, number of subjects; SC, subcutaneous.

Figure 6A:
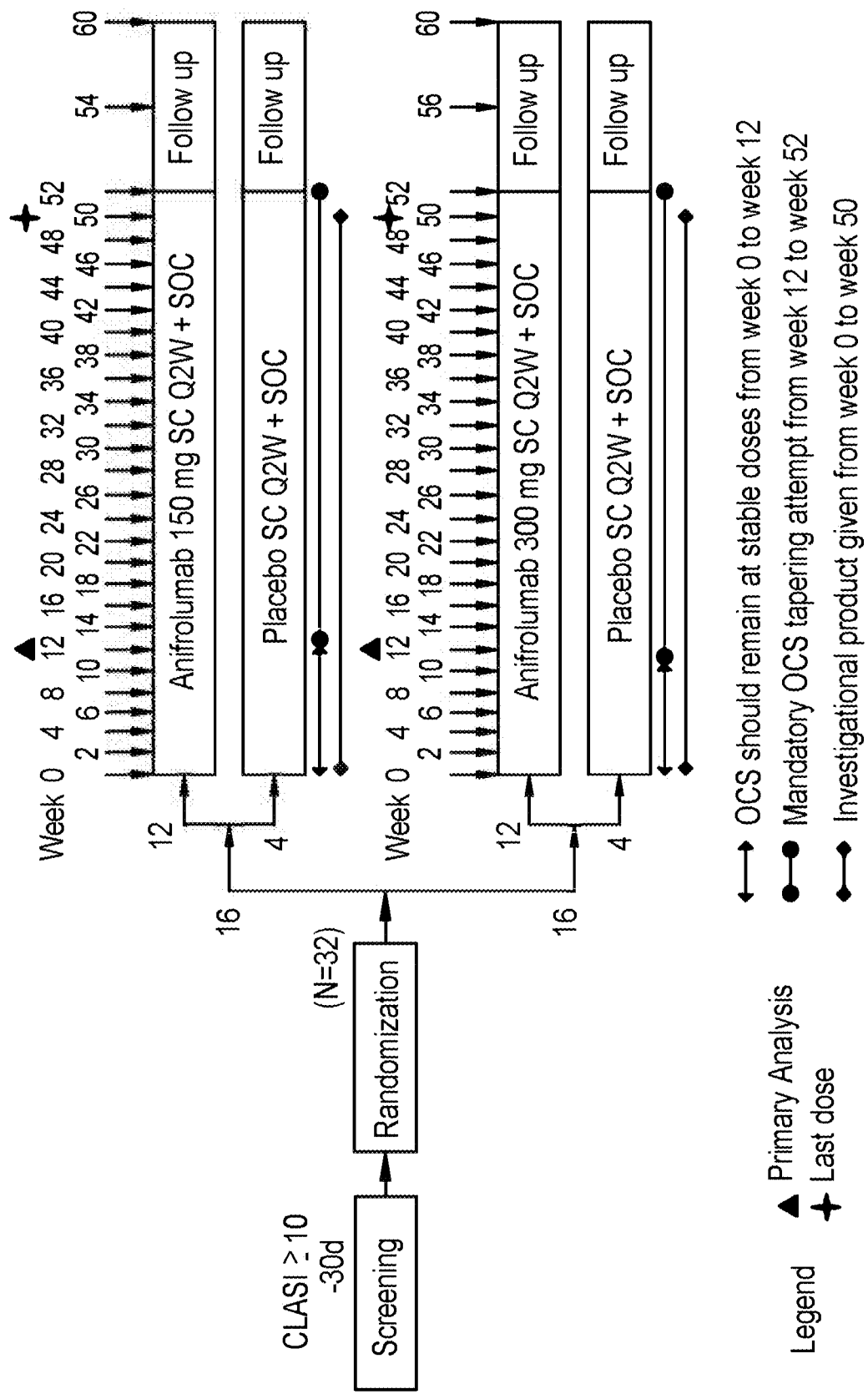
Figure 6B:
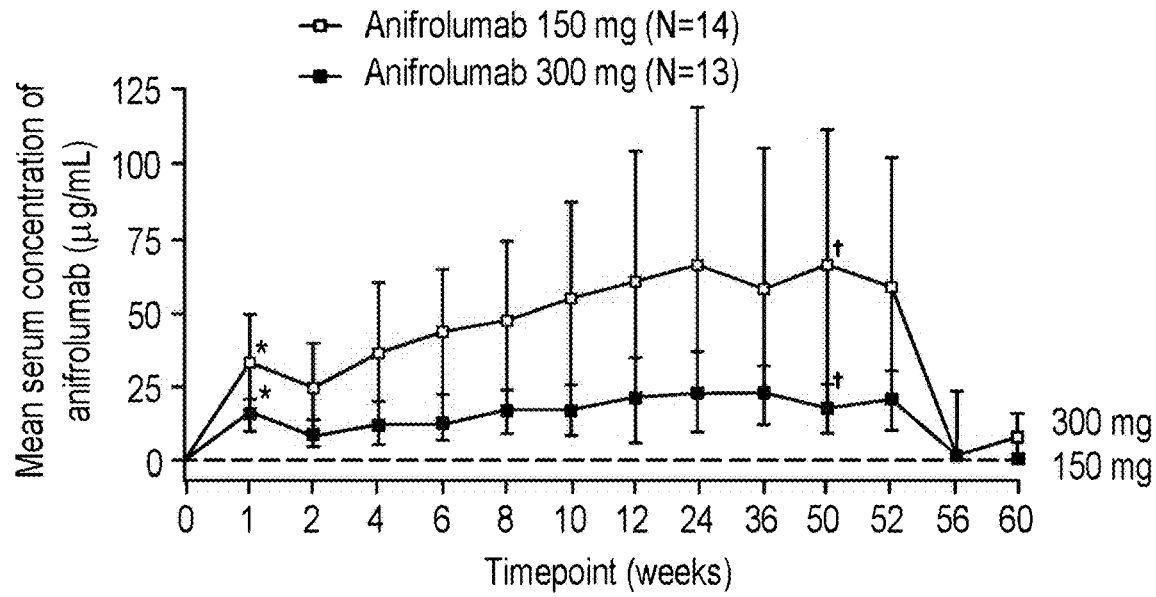
Figure 6C:
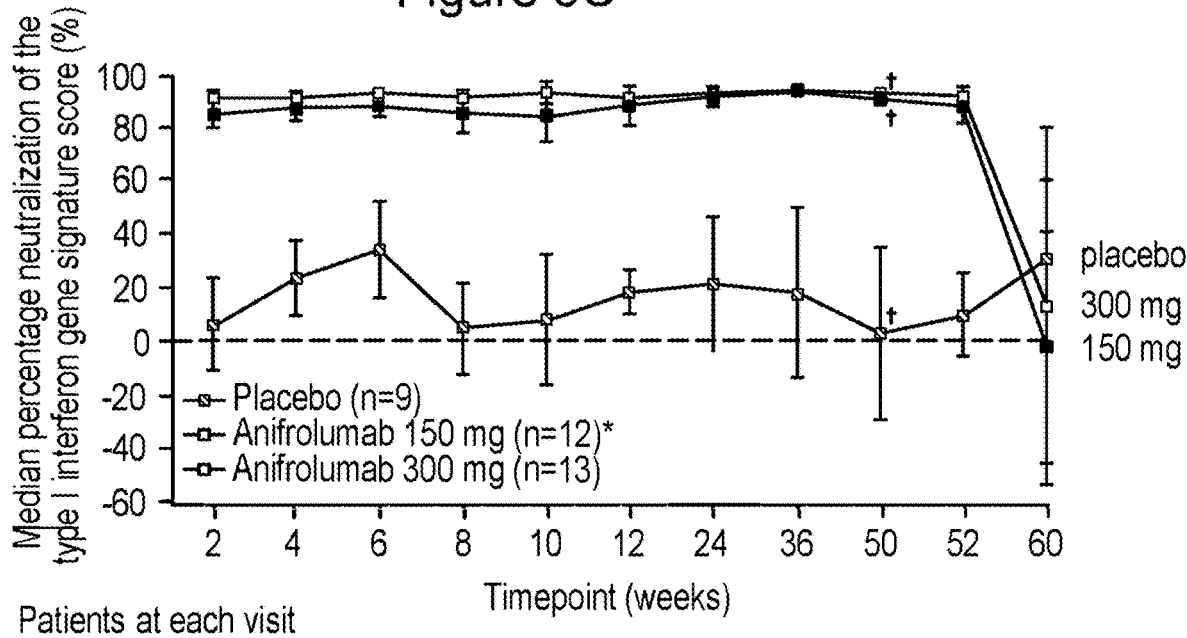

FIG. 6A-6C: Study 08 study design and results

FIG. 6A: Study design for phase II of SC anifrolumab in SLE patients. Study 08 (NCT02962960) evaluated the effect of two anifrolumab doses every other week. FIG. 6B: Mean serum concentration of anifrolumab over time. FIG. 6C: Anifrolumab neutralization of the type I IFN gene signature.

Figure 7A:
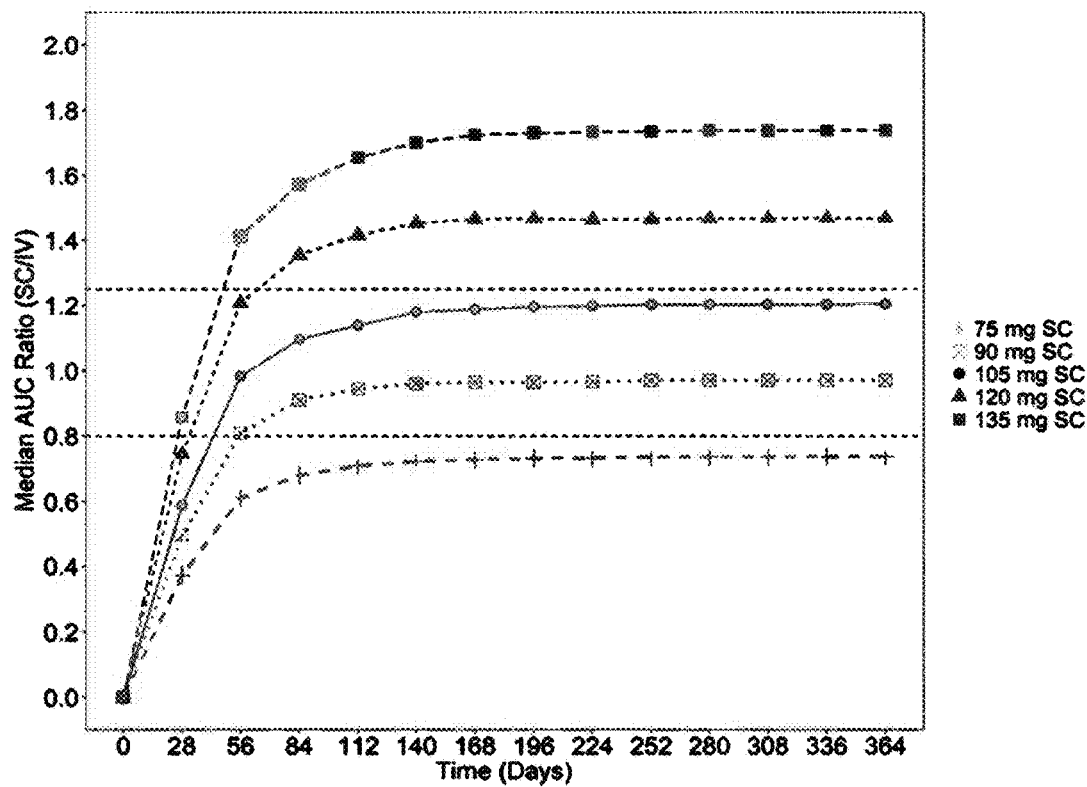
Figure 7B:
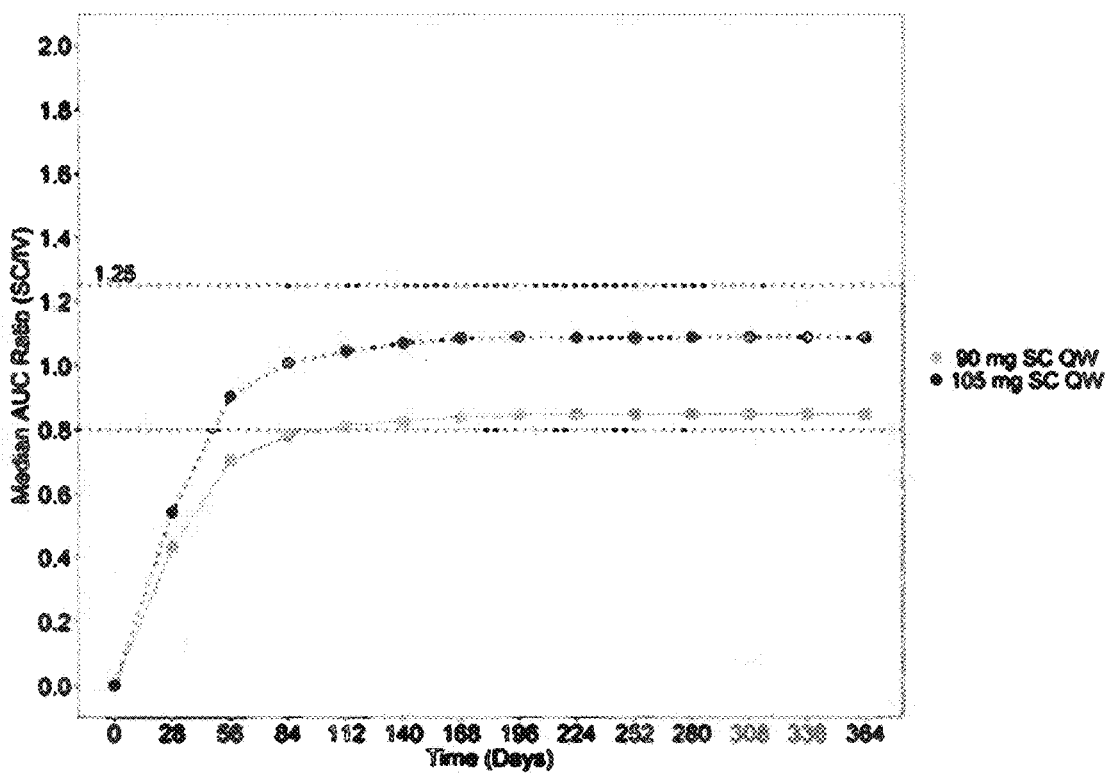

FIG. 7A-7B: Computed median AUC Ratios (SC/IV)

FIG. 7A: Computed median AUC Ratio (SC/IV) between weeks 0-52 for various SC doses. The computed median AUC Ratio (SC/IV), based on the estimated bioavailability from Study 06, between weeks 0-52, where the subcutaneous dose is either 75 mg (+ sign), 90 mg (empty squares), 105 mg (circles), 120 mg (triangles), or 135 mg (filled squares). The subcutaneous dose here is administered once every 7 days (QW); the IV dose is administered once every 4 weeks (Q4W) at a dose of 300 mg. Based on the AUC, both 90 and 105 mg SC QW appear similar to 300 mg IV. FIG. 7B: Computed median AUC ratio (SC/IV) for 90 mg and 105 mg SC QW. The computed median AUC Ratio (SC/IV), based on the estimated bioavailability ~7% lower than the bioavailability calculated from Study 06, between weeks 0-52, where the subcutaneous dose is either 90 mg SC QW or 105 mg SC.

Figure 8A:
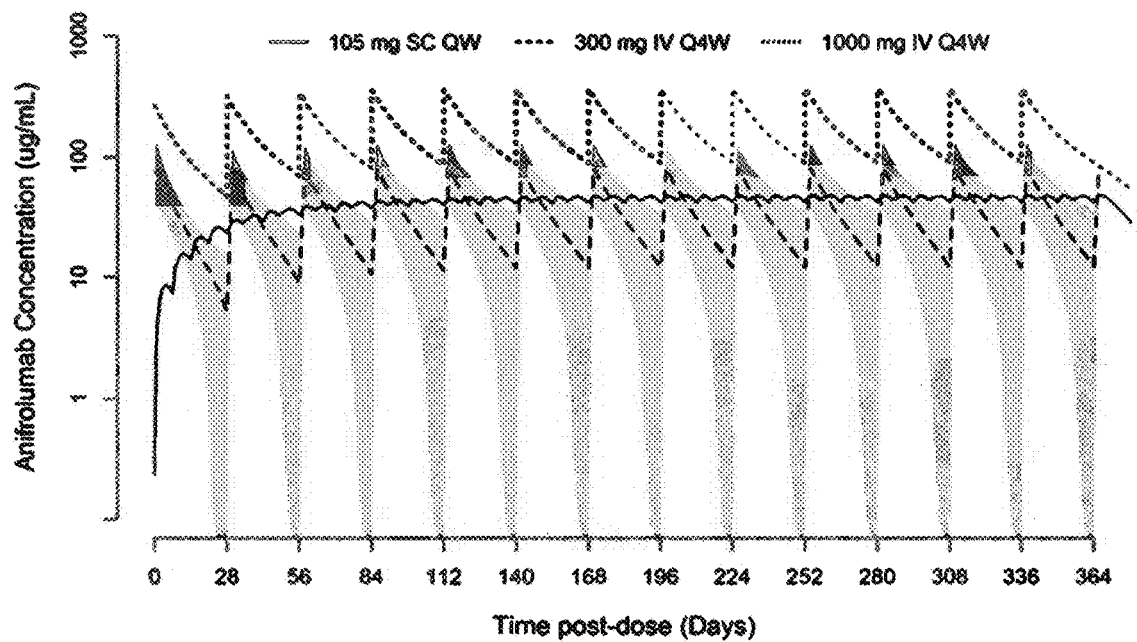
Figure 8B:
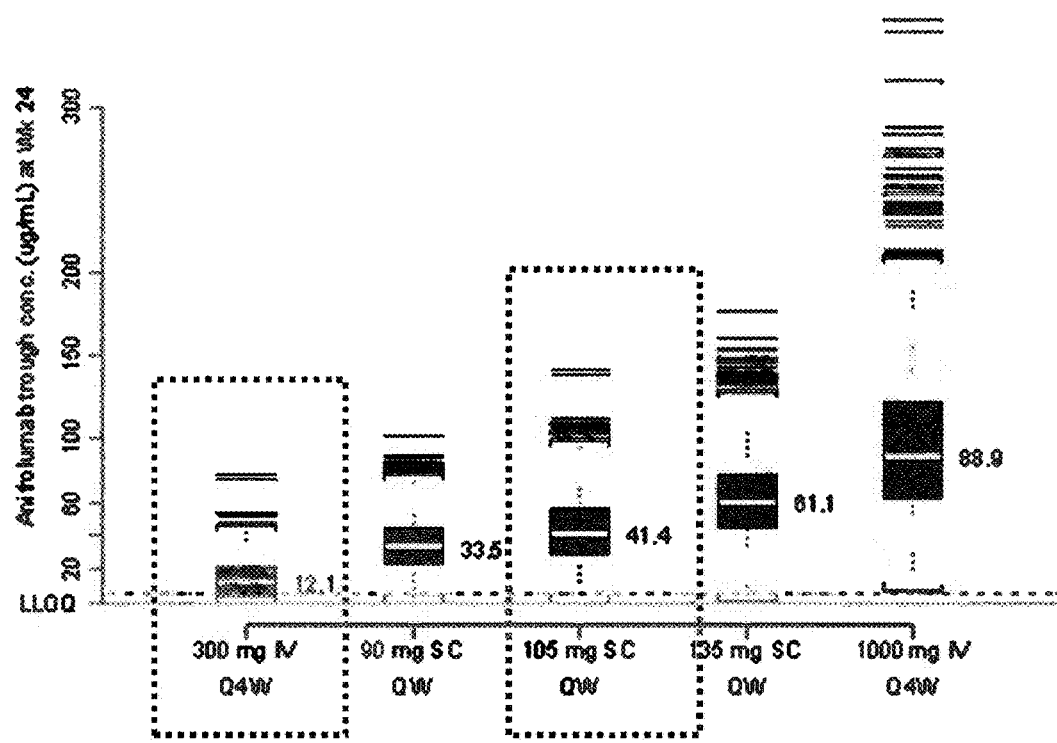

FIG. 8A-8B: Anifrolumab concentration over time at different doses

FIG. 8A: A plot showing (computed) trough concentrations of plasma anifrolumab in a patient administered either (i) 105 mg of anifrolumab subcutaneously, once every 7 days (straight line); (ii) 300 mg anifrolumab intravenously, once every 4 weeks (lower dotted line); (ii) 1000 mg anifrolumab intravenously, once every 4 weeks (upper dotted line). Shaded area represents the area between 5th and 95th percentiles of the 300 mg IV Q4W dose. FIG. 8B: Anifrolumab trough concentration in IFNGS high SLE subjects. Computed trough concentrations of anifrolumab in IFNGS high patients plasma after administration as follows: (i) 300 mg IV Q4W; (ii) 90 mg SC QW; (iii) 105 mg SC QW; (iv) 135 mg SC QW; (v) 1000 mg IV Q4W. SC=subcutaneous. Based on trough, both 90 and 105 mg SC QW were projected to have higher PD suppressions than 300 mg IV.

Figure 9A:
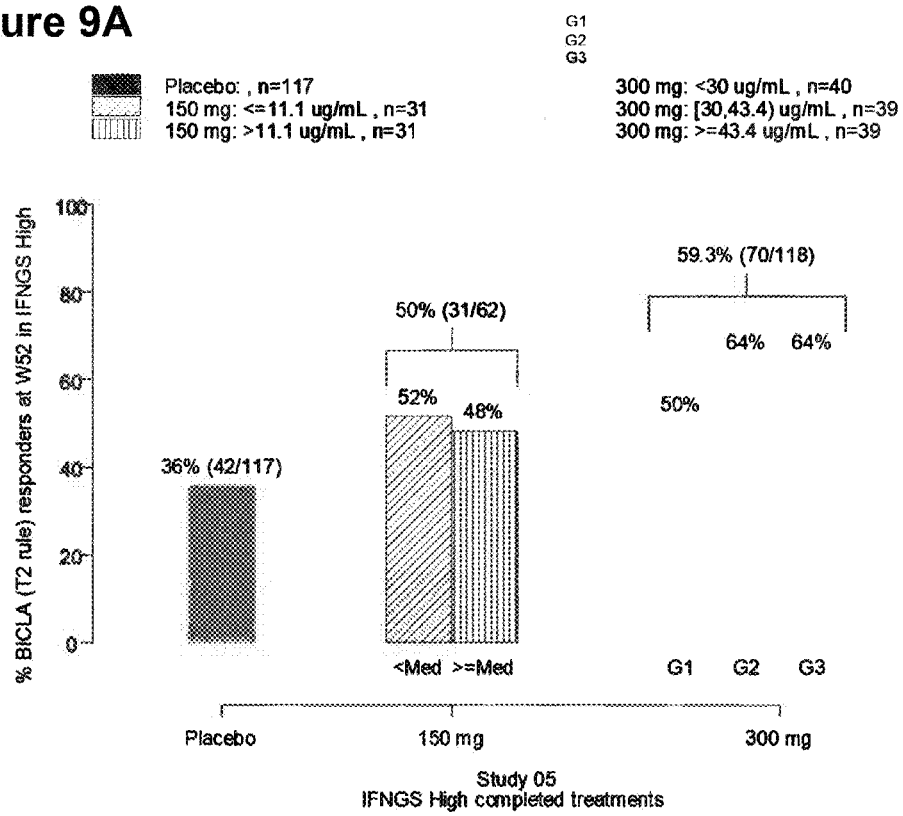
Figure 9B:
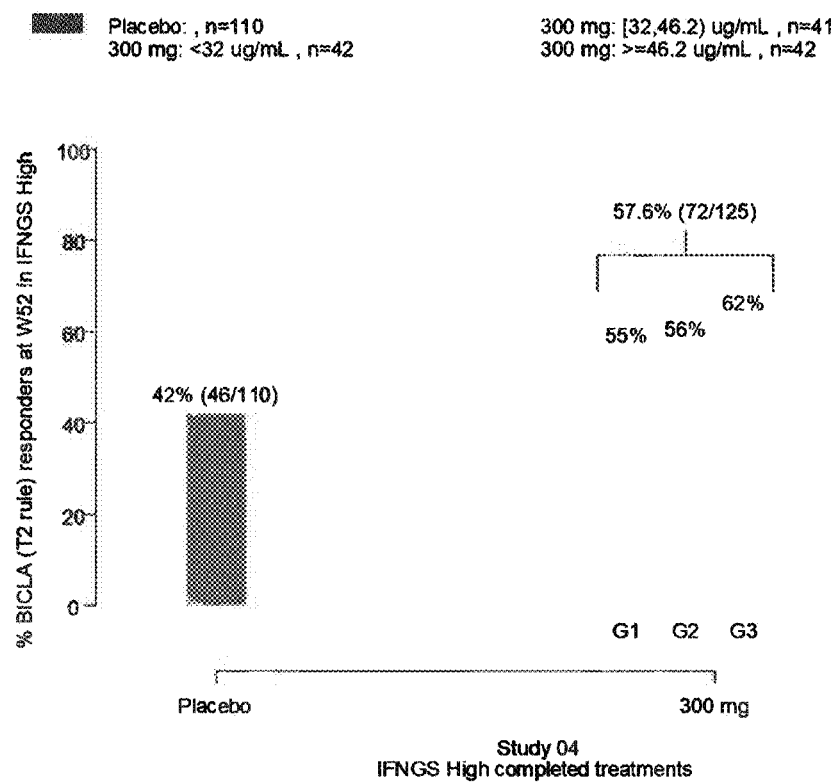

FIG. 9A-9B: Positive Exposure-BICLA relationship observed in TULIP 1 & TULIP 2 in IFNGS high patients FIG. 9A: TULIP I, for placebo, 150 mg and 300 mg anifrolumab. FIG. 9B: TULIP II, for placebo and 300 mg.

Figure 10A:
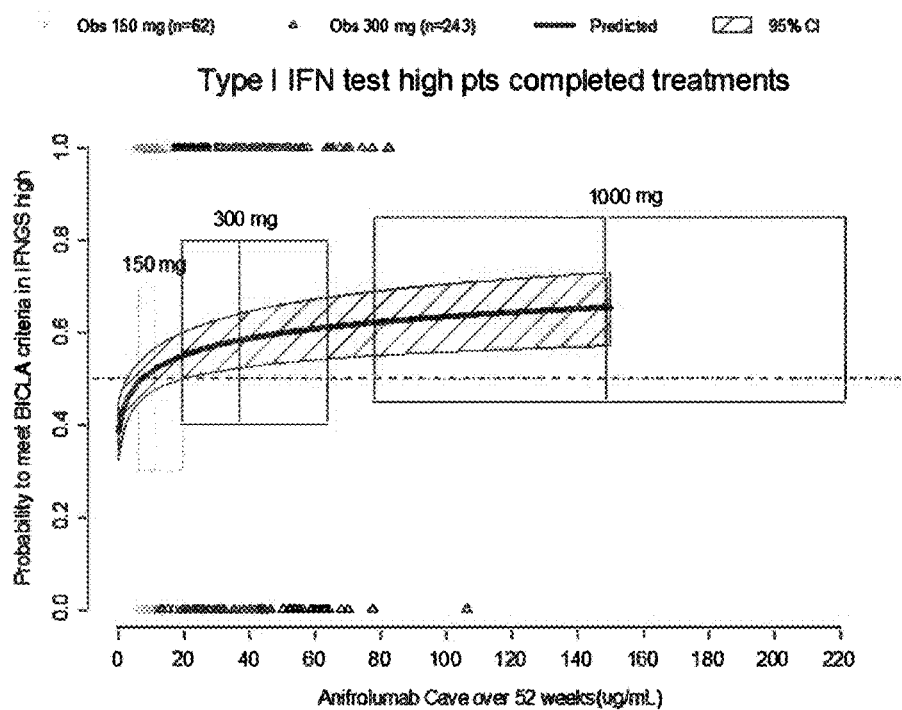
Figure 10B:
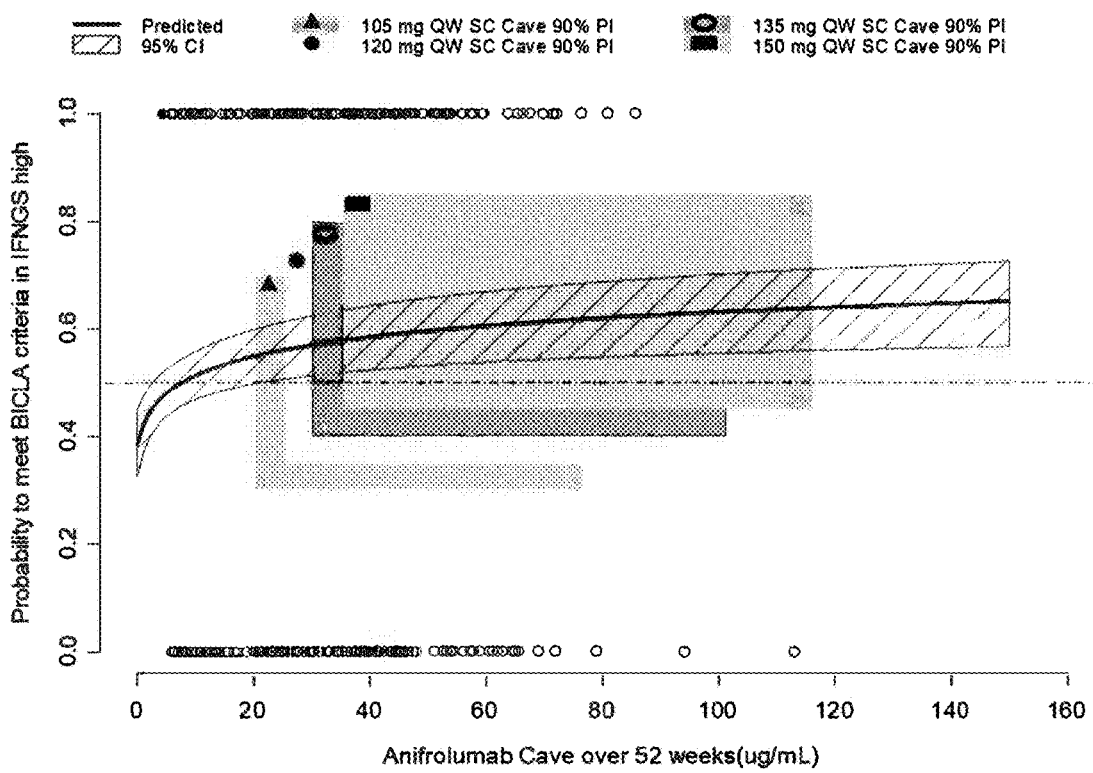

FIG. 10A-10B: BICLA dose response

FIG. 10A: Dose response curve, for probability of meeting BICLA response criteria (in IFNGS high patients) versus anifrolumab $C_{ave}$ over 52 weeks, showing the predicted mean (grey line) and 95% confidence interval (CI) (dashed area). Patients are grouped by dose (150 mg, n=62; 300 mg, n=242; and 1000 mg). FIG. 10B: Predicted PK and efficacy for different SC doses. The probability of meeting BICLA (in IFNGS high patients) for weekly subcutaneous doses starting from 105 mg, and up to 150 mg. Assumptions for generating the data include no dose delays/interruptions.

Figure 11A:
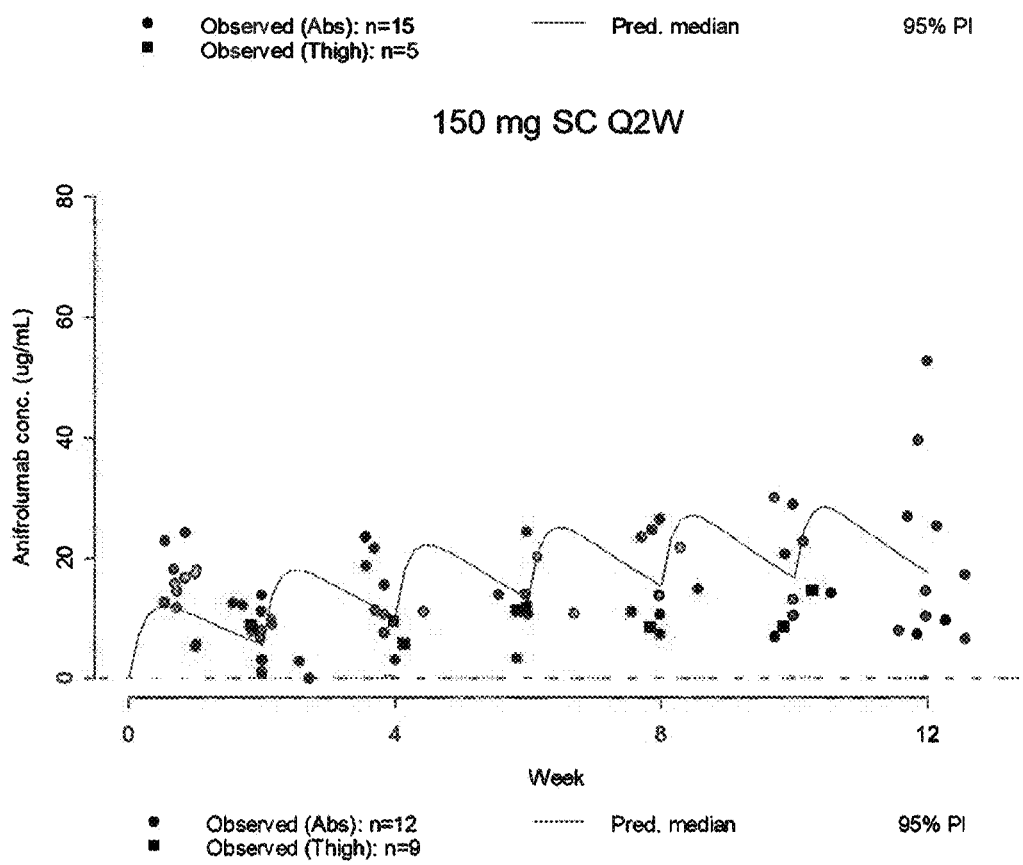
Figure 11B:
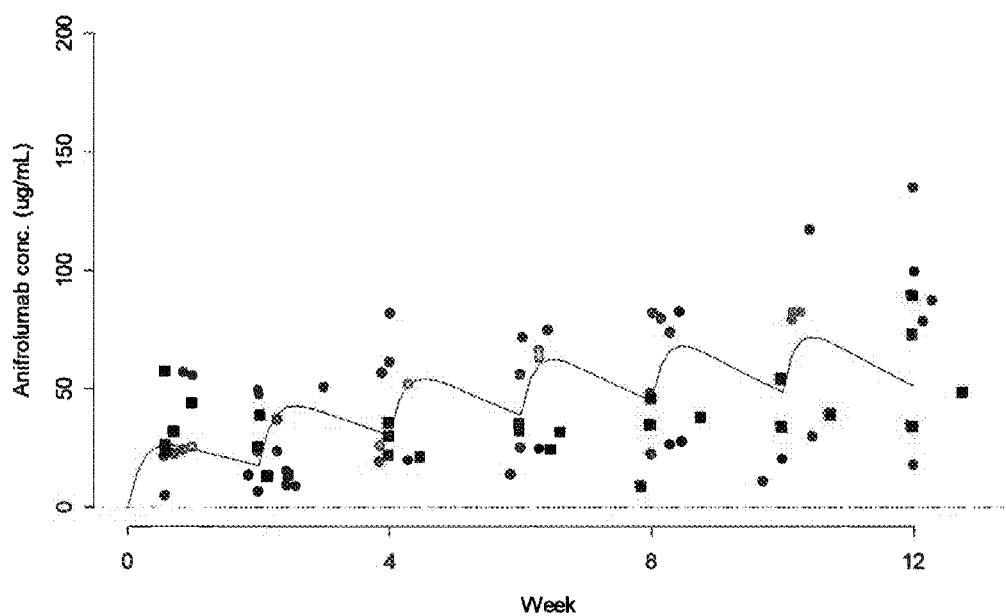

FIG. 11A-11B: $C_{troughs}$ following injection at thigh compared to injection at abdomen $C_{troughs}$ following injection at thigh trended downward compared to injection at abdomen. FIG. 11A: 150 mg SC Q2W. FIG. 11B: 300 mg SC Q2W.

Figure 12:
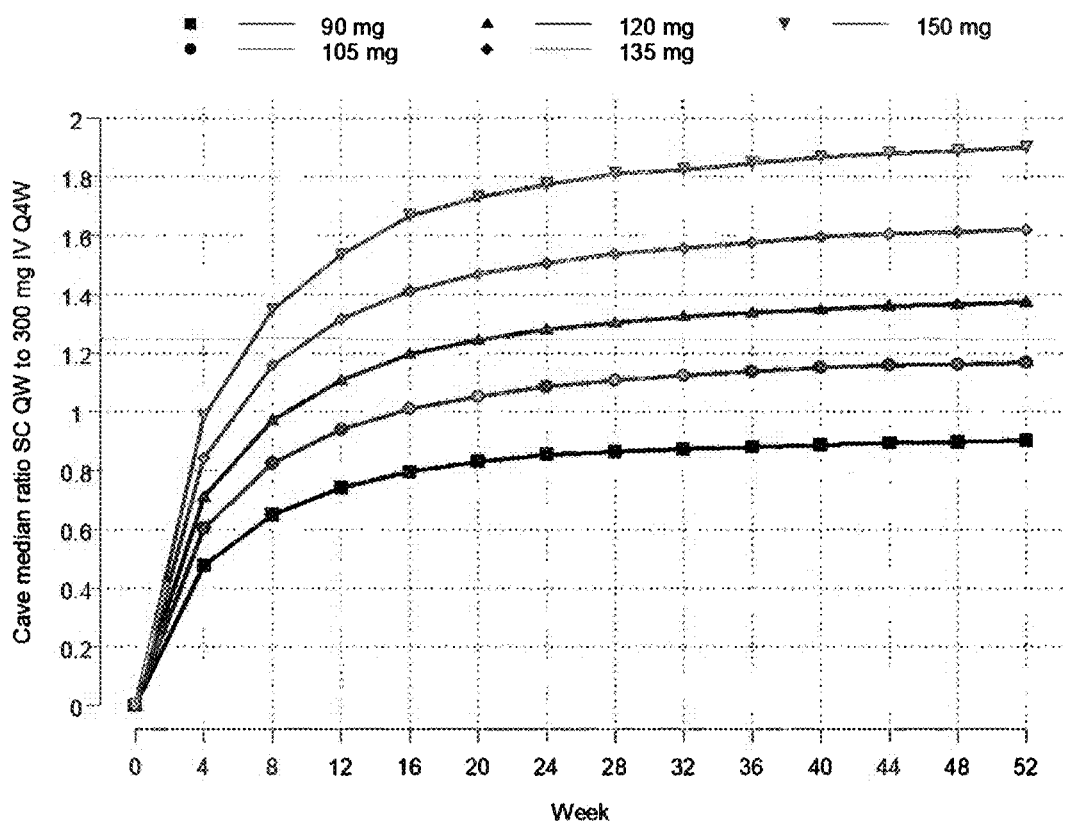

FIG. 12: Exposure prediction based on 81-87% bioavailability and preliminary PK modelling Anifrolumab $C_{ave}$ medium ratio predicted for 90-150 mg SC QW to 300 mg Q4W, based on PK preliminary modelling and bioavailability assumptions. If a bioavailability (F1) of 81-87% was assumed, 105 mg was initially projected to provide a comparable $C_{ave}$ to that of 300 mg IV.

Figure 13A:
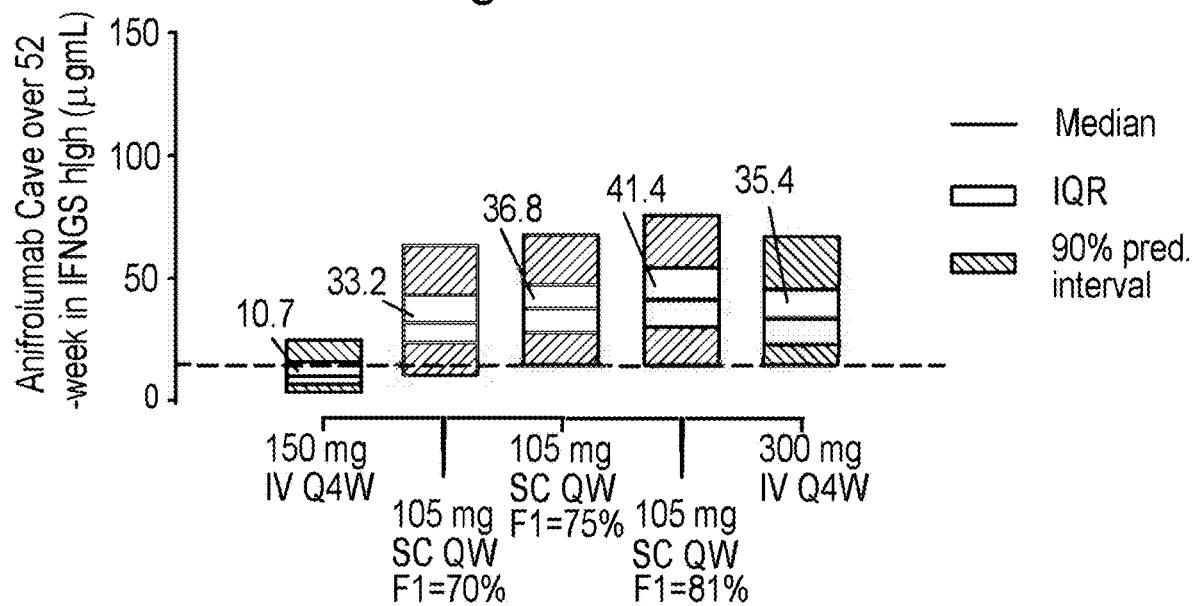
Figure 13B:
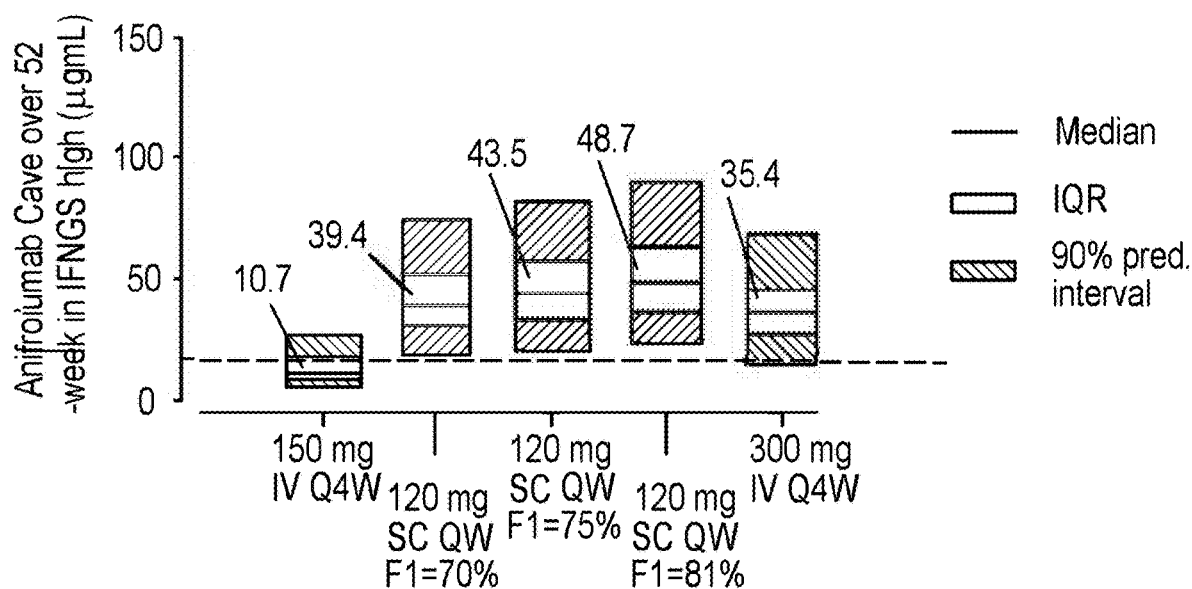
Figure 13C:
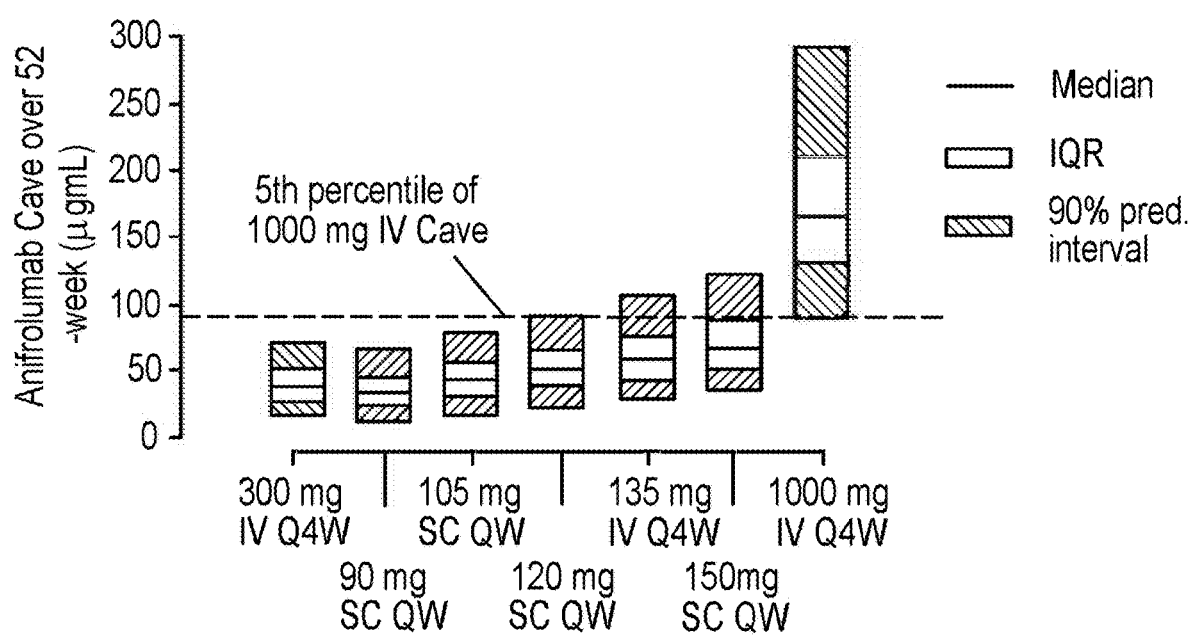

FIG. 13A-13C: Anifrolumab $C_{ave}$ over 52 weeks in IFNGS high patients for different SC and IV doses When the estimated bioavailability was reduced to ~70% or less, the median $C_{ave}$ of the 105 mg QW subcutaneous dose fell to below 1. FIG. 13A: 105 mg SC QW. FIG. 13B: 120 mg SC QW. FIG. 13C: Overlap with 1000 mg IV Q4W.

Figure 14A:
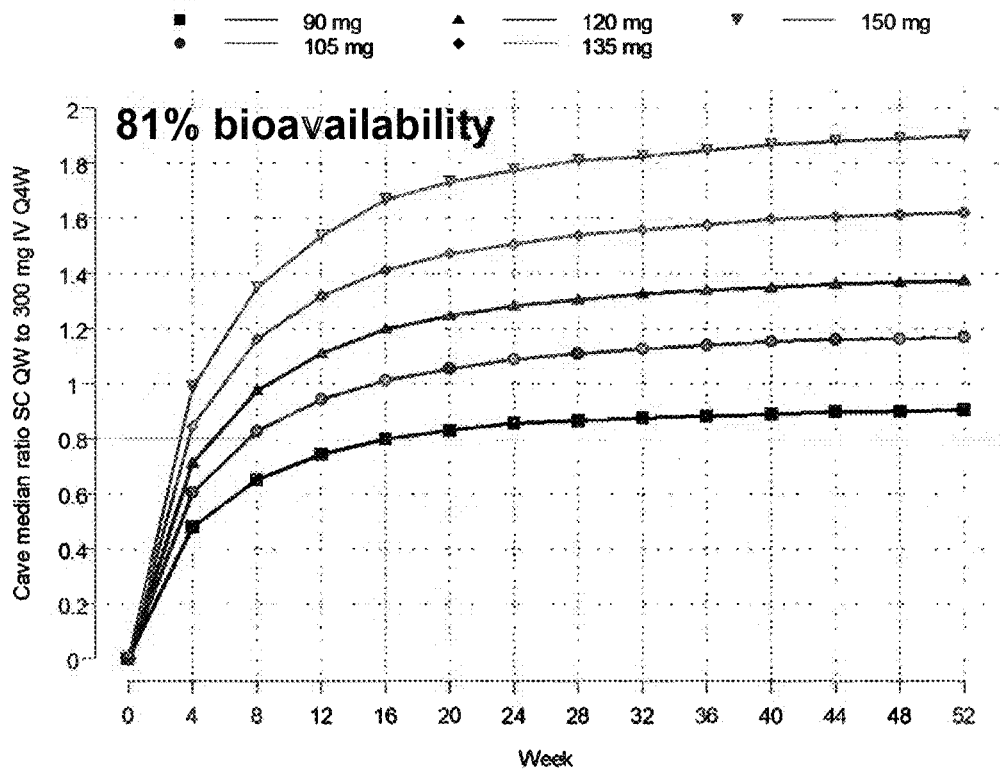
Figure 14B:
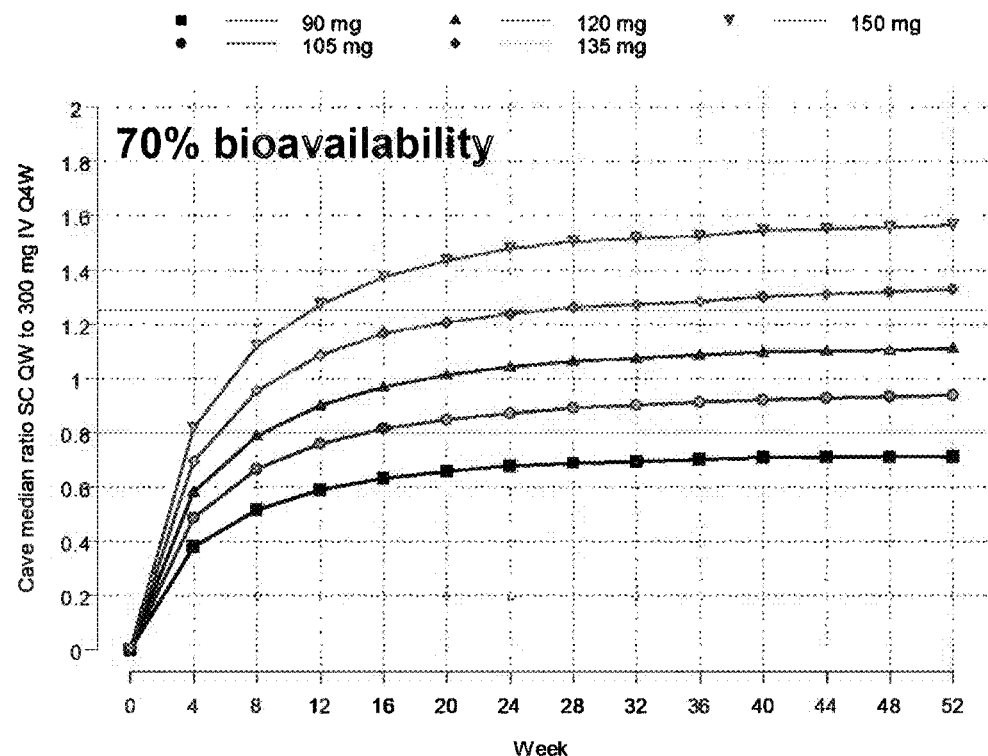

FIG. 14A-14B: $C_{ave}$ median ratio SC QW to 300 mg IV Q4W

Selection of a dose higher than 105 mg, preferably 120 mg or higher, optimizes the exposure-response by minimizing the impact of the variability of the onset of response and bioavailability in patients with lupus (e.g. SLE). FIG. 14A: 81% bioavailability assumed. FIG. 14B: 70% bioavailability assumed.

Figure 15:
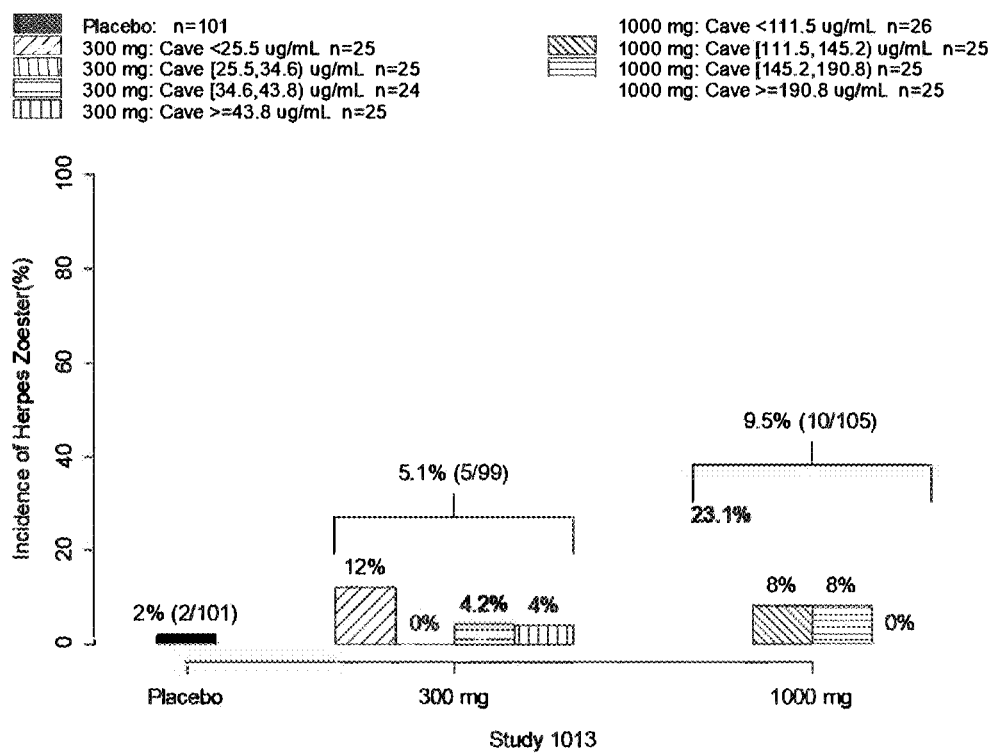

FIG. 15: Average anifrolumab concentration versus herpes zoster incidence

The incidence of Herpes Zoster (%) in patients in the Study 1013 receiving placebo, 300 mg IV anifrolumab or 1000 mg IV anifrolumab. A SC dose of below 150 mg QW is also desirable to reduce the risk of herpes zoster infection.

Figure 16:
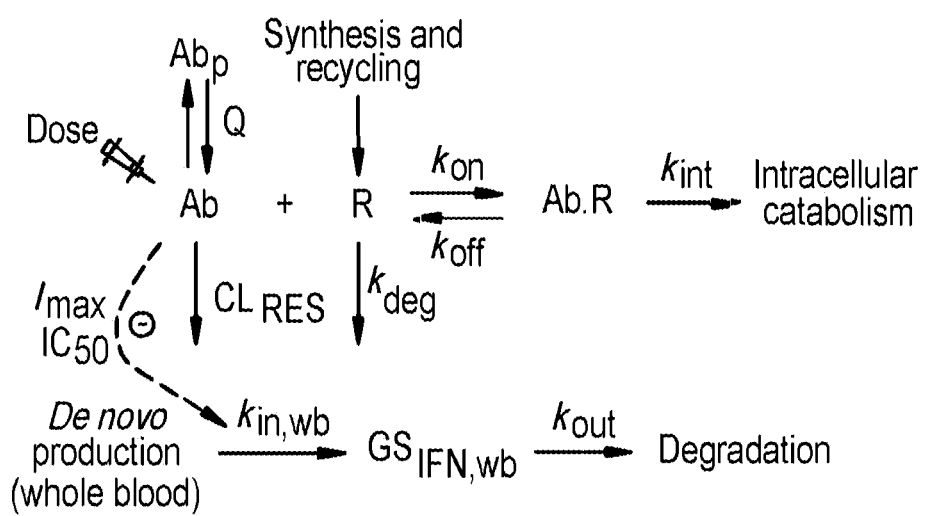

FIG. 16: Schematic of the PK/PD Model

A nonlinear mixed-effects model. Ab, anifrolumab in the central compartment; $Ab_p$, anifrolumab in the peripheral tissue compartment; Ab.R, anifrolumab-IFNAR1 complex; $CL_{RES}$, clearance by the reticuloendothelial system; $GS_{IFN,wb}$, type I IFN PD signature in the whole blood; $IC_{50}$, potency, anifrolumab concentration corresponding to half maximum inhibition of PD signature production; IFN, interferon; $I_{max}$, maximum fractional extent of inhibition of PD signature production by anifrolumab; $k_{deg}$, degradation rate constant of IFN-αR1; $k_{in,wb}$, production rate constant of IFN genes in the whole blood; $k_{int}$, internalization rate constant; $k_{off}$, dissociation rate constant; $k_{on}$ association rate constant; $k_{out}$, elimination rate constant of IFN genes; PD, pharmacodynamic; PK, pharmacokinetic; Q, inter-compartmental clearance; wb, whole blood.

Figure 17:
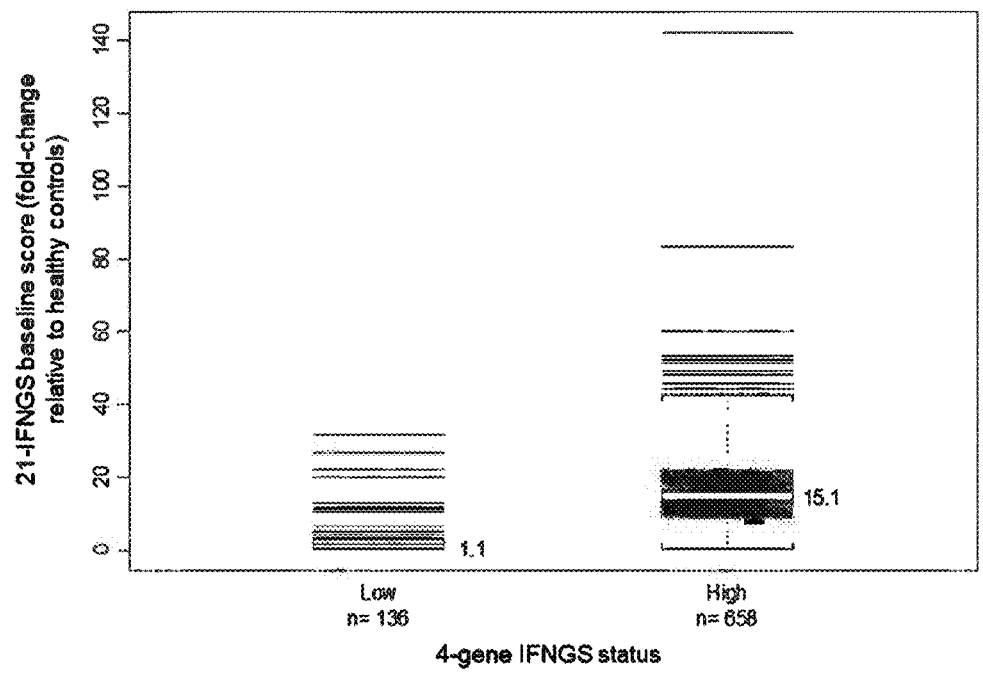

FIG. 17: Association Between 4-Gene IFNGS Status at Screening (High or Low) and Baseline 21-Gene IFNGS in Data Pooled From TULIP-1 and TULIP-2 Trials 21-IFNGS, 21-gene pharmacodynamic interferon gene signature; IFNGS, interferon gene signature; SLE, systemic lupus erythematosus. Data points are displayed as fold-change in 21-IFNGS in patients with SLE in the TULIP-1 and TULIP-2 trials relative to 30 pooled healthy controls. The numbers displayed indicate the median values for each group. Of 819 patients who received at least one dose of anifrolumab 300 mg, anifrolumab 150 mg, or placebo in the TULIP-1 and TULIP-2 trials, 25 patients (18 IFNGS-high and 6 IFNGS-low patients) were missing baseline 21-IFNGS score, and so only 794 patients were included in this analysis.

FIG. 18: IFNGS Status at Screening and 21-IFNGS Score at Baseline by Age Group in Data Pooled From TULIP-1 and TULIP-2

The negative association between age and IFNGS expression was observed for both the dichotomous IFNGS test at screening and median 21-IFNGS score at baseline. 21-IFNGS, 21-gene pharmacodynamic interferon gene signature; IFNGS, interferon gene signature.

Figure 19:
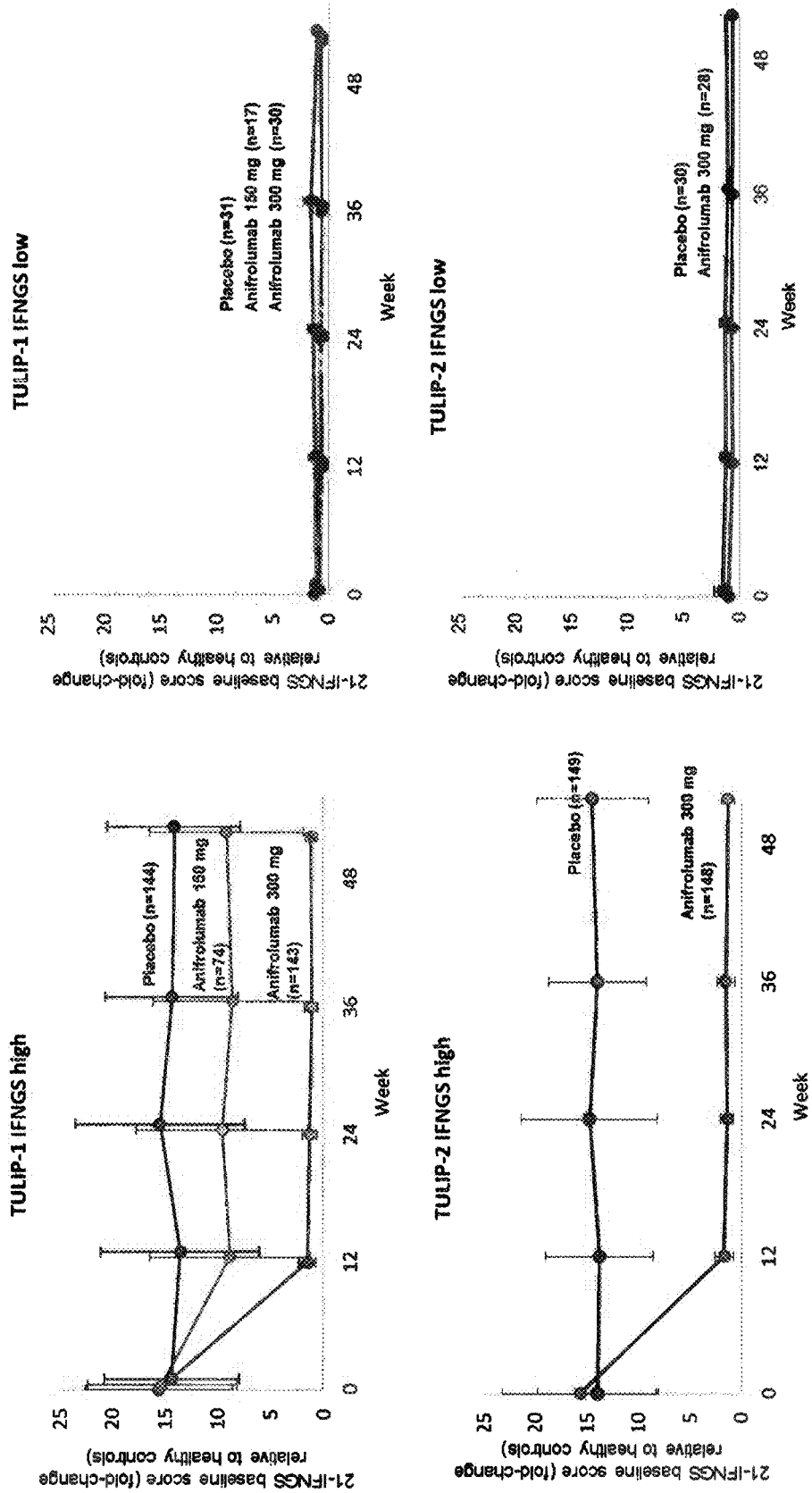

FIG. 19: 21-IFNGS Score (Fold-Change Relative to Healthy Controls) in IFNGS-high vs IFNGS-low Patients in TULIP-1 and TULIP-2

21-IFNGS, 21-gene pharmacodynamic interferon gene signature; IFNGS, interferon gene signature; SLE, systemic lupus erythematosus. The y-axes represent the median fold-change in 21-IFNGS in patients with SLE relative to 30 pooled healthy controls. Error bars represent median absolute deviation. This analysis included 439 patients in TULIP-1 and 355 patients in TULIP-2 with at least one baseline or post-baseline 21-IFNGS measurement.

Figure 20:
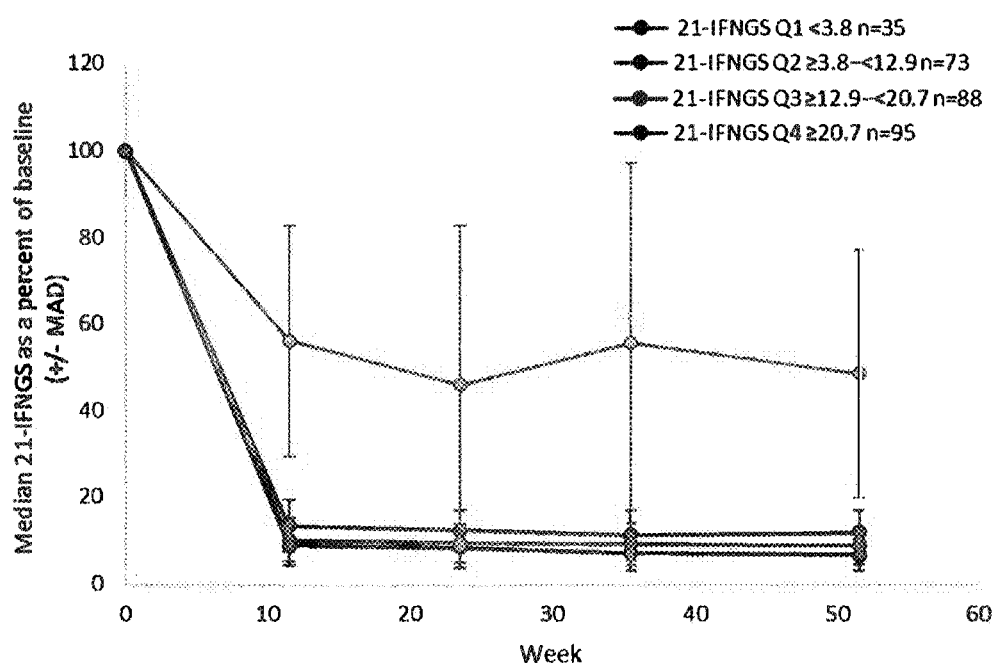

FIG. 20: Median 21-Gene IFNGS Neutralization by Baseline 21-IFNGS Quartiles Among Pooled Data from IFNGS-high Patients Treated With Anifrolumab 300 mg in TULIP-1 and TULIP-2

Patients in the lowest baseline 21-IFNGS quartile (who had baseline 21-IFNGS that was closest to that observed in IFNGS-low patients), had lower PD neutralization with larger variability than patients in higher baseline 21-IFNGS quartiles. 21-IFNGS, 21-gene pharmacodynamic interferon gene signature; IFNGS, interferon gene signature; MAD, median absolute deviation; PD, pharmacodynamic; Q, quartile. This analysis included the 291 IFNGS-high patients treated with anifrolumab 300 mg from TULIP-1 and TULIP-2 who had the baseline 21-IFNGS measurement. The baseline 21-IFNGS quartiles were calculated based on 794 patients (IFNGS-high or IFNGS-low) who received at least one dose of anifrolumab 300 mg, anifrolumab 150 mg, or placebo in the TULIP-1 and TULIP-2 trials, who had the baseline 21-IFNGS measurement; as this plot only includes IFNGS-high patients, numbers in each quartile are not equal.

Figure 21A:
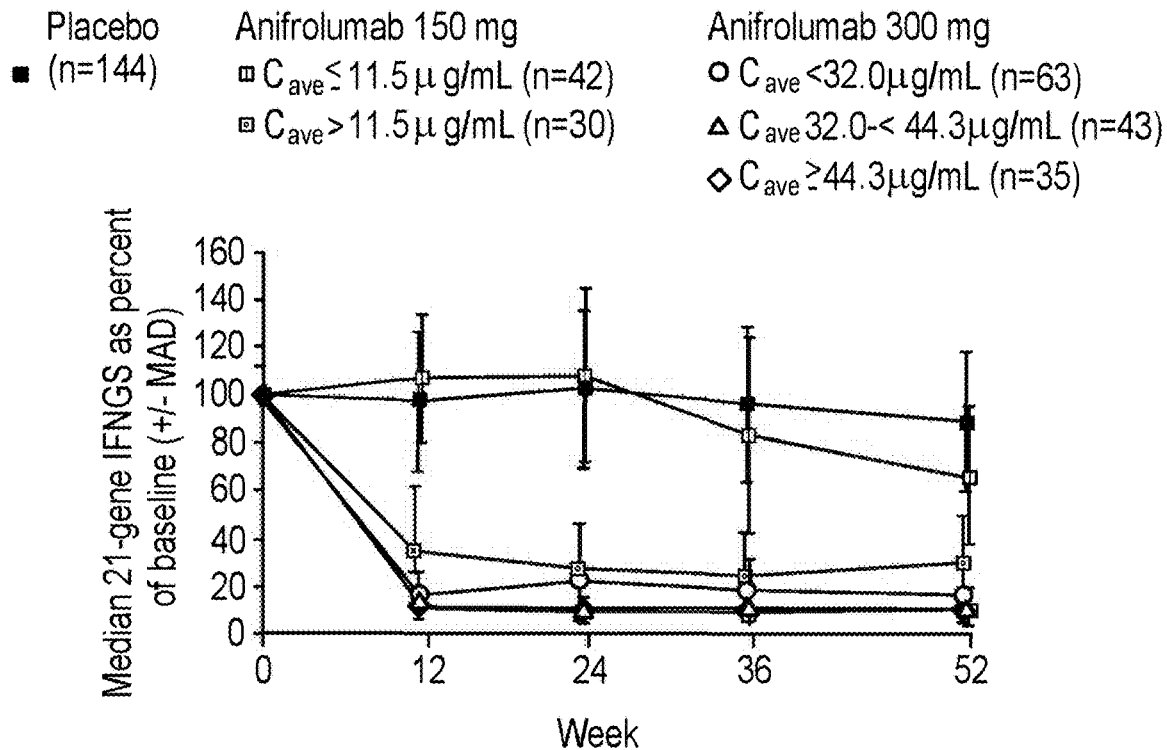
Figure 21B:
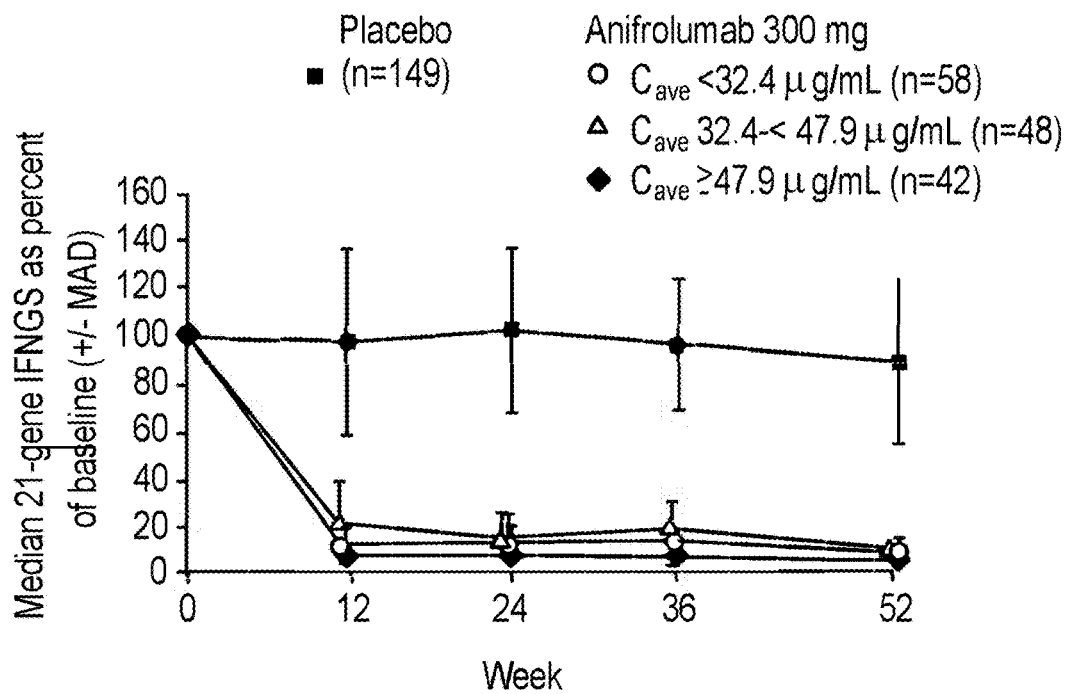

FIG. 21A-21B: Observed PD Neutralization of the 21-Gene Type I IFNGS According to Cave Subgroup Over the 52-Week Treatment Duration in TULIP-2 and TULIP-1

FIG. 21A: TULIP-2. FIG. 21B: TULIP-1. $C_{ave}$, average anifrolumab concentration over the treatment period; IFNGS, interferon gene signature; MAD, median absolute deviation; PD, pharmacodynamic; PK, pharmacokinetic. Figure includes IFNGS-high patients with ≥1 quantifiable serum PK observation and ≥1 PD measurement prior to discontinuation; PD measurements collected after discontinuation were not included.

Figure 22:
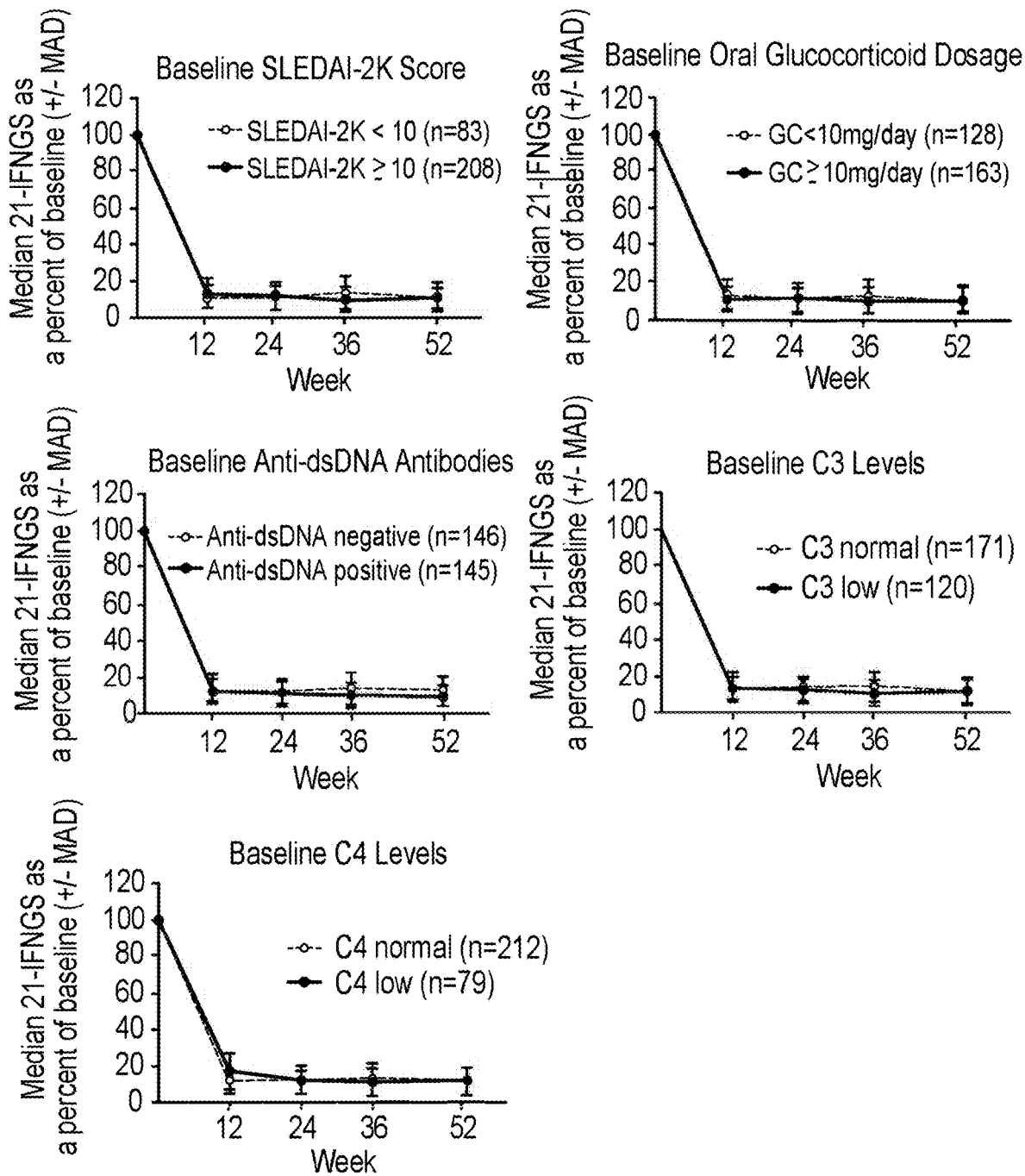

FIG. 22: 21-IFNGS Pharmacodynamic Neutralization in IFNGS-High Patients Treated With Anifrolumab 300 mg According to Baseline Disease Characteristics Substantial and sustained PD neutralization with anifrolumab 300 mg was observed consistently across baseline disease activity subgroups, including subgroups based on SLEDAI-2K score (<10 vs ≥10), oral glucocorticoid dosage (<10 vs ≥10 mg day$^{-1}$), and lupus serologies (anti-dsDNA antibodies, C3, and C4). 21-IFNGS, 21-gene pharmacodynamic interferon gene signature; anti-dsDNA, anti-double-stranded DNA; C3, complement 3; C4, complement 4; GC, glucocorticoid; IFNGS, interferon gene signature; MAD, median absolute deviation; SLEDAI-2K, Systemic Lupus Erythematosus Disease Activity Index 2000.

FIG. 23: Visual Predictive Check of PK/PD Model for Anifrolumab 150 mg and 300 mg The PK/PD modeling analysis included 646 IFNGS-high patients from the pooled TULIP-1 and TULIP-2 trials who received placebo (n=289), anifrolumab 150 mg (n=70), or anifrolumab 300 mg (n=287). The PK/PD indirect response model adequately captured the observed data by the 95% prediction interval as demonstrated by visual predictive checks. 21-IFNGS, 21-gene pharmacodynamic interferon gene signature; Obs, observed; Obs-Med, observed median; PD, pharmacodynamic; PK, pharmacokinetic; PI, prediction interval. The dark line shows the predicted median percent neutralization of the 21-IFNGS expression. Analysis was based on 646 IFNGS-high patients in the PK/PD analysis set (289 in placebo, 70 in the 150 mg group, and 287 in the 300 mg group).

Figure 24:
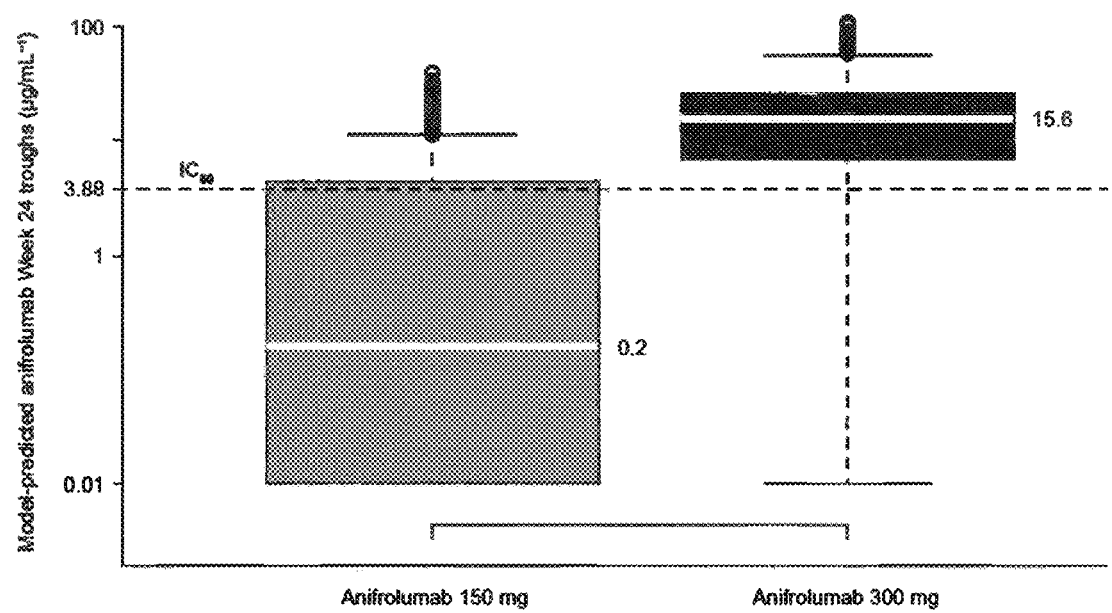
Figure 25A:
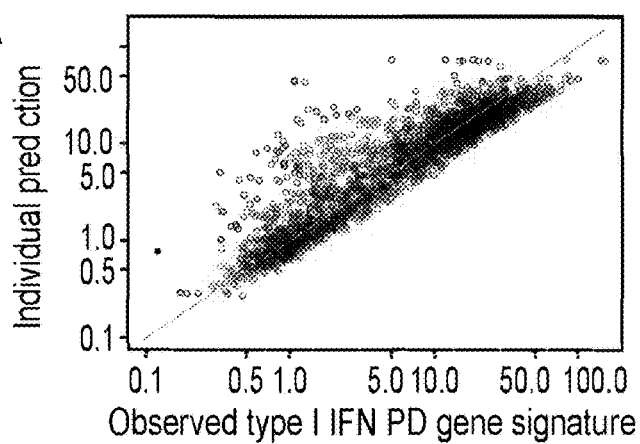
Figure 25B:
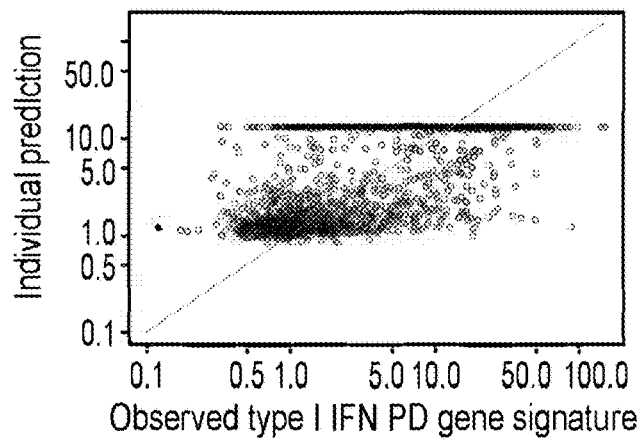
Figure 25C:
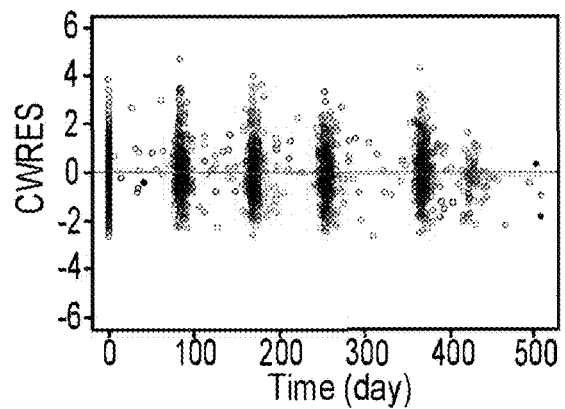
Figure 25D:
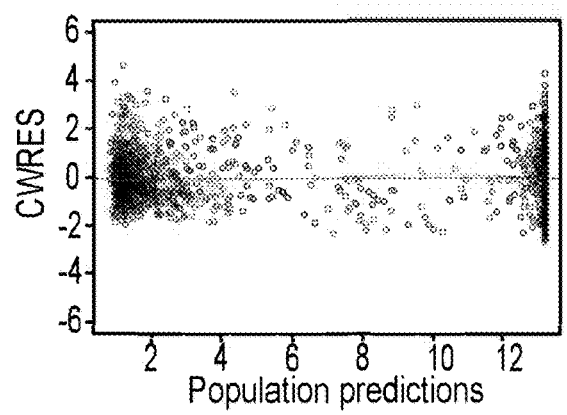

FIG. 24: PK/PD Model-Predicted Week 24 Anifrolumab Concentration Troughs for Anifrolumab 150 mg and 300 mg The estimated median Week 24 $C_{trough}$ was higher with anifrolumab 300 mg than with anifrolumab 150 mg (15.6 vs 0.2 µg mL$^{-1}$), owing to nonlinearity. 21-IFNGS, 21-gene type I interferon gene signature; PD, pharmacodynamic; PK, pharmacokinetic. $IC_{80}$ is the approximate anifrolumab concentration required to produce 80% of the maximum inhibition of the 21-IFNGS expression. Predicted values based on 5000 simulations of the nonlinear mixed-effects PK/PD model implemented into the software NONMEM® (version 7.3 or higher).

FIG. 25A-25D: Diagnostic Plots for PK/PD Model

CWRES, conditional weighted residuals; IFN, interferon; PD, pharmacodynamic; PK, pharmacokinetic. The green line represents the line of identity in FIG. 25A and FIG. 25B and the LOESS (locally weighted smoothing) line in FIG. 25C and FIG. 25D.

Figure 26A:
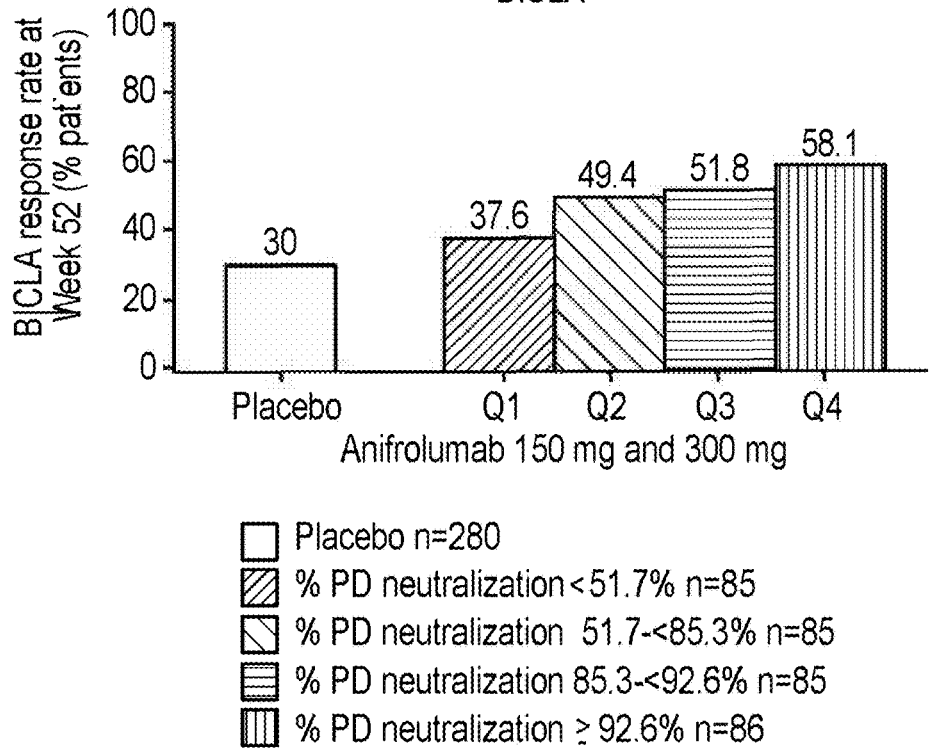
Figure 26B:
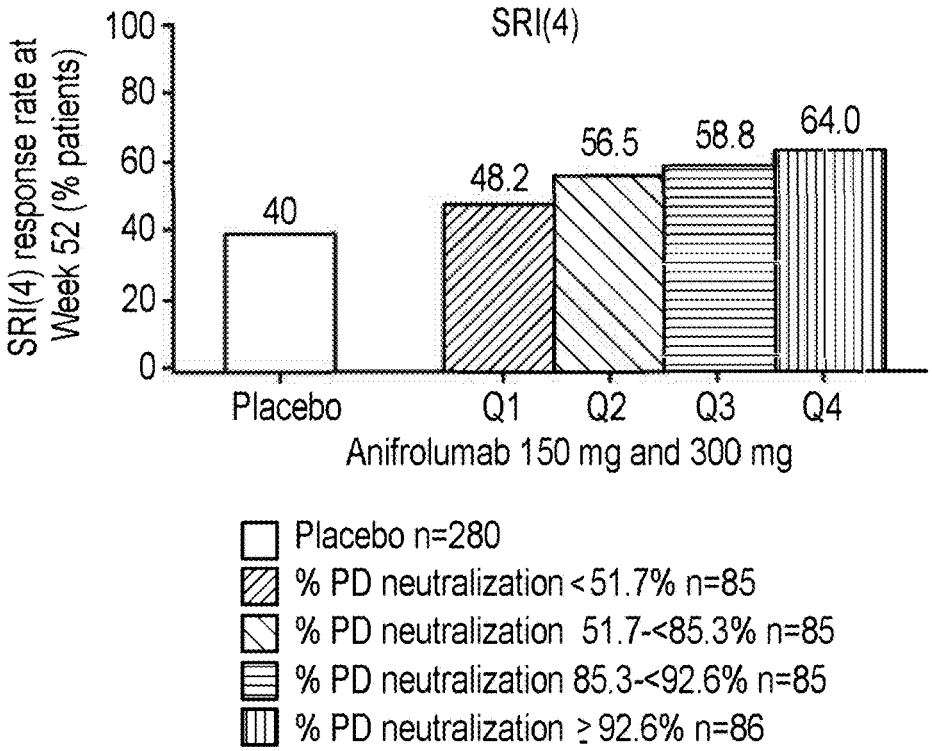

FIG. 26A-26B: BICLA and SRI(4) Response Rates at Week 52 by Median Type I 21-IFNGS PD Neutralization Quartiles in Type I IFNGS-high Patients FIG. 26A: BICLA; FIG. 26B: SRI(4). BICLA, British Isles Lupus Assessment Group (BILAG)-based Composite Lupus Assessment; IFNGS, interferon gene signature; PD, pharmacodynamic; SRI(4), Systemic Lupus Erythematosus Responder Index ≥4. The analysis included IFNGS-high patients with baseline and at least one post-baseline PD assessment before discontinuation, who received anifrolumab 150 mg or 300 mg (n=341) or placebo (n=280) in the TULIP-1 and TULIP-2 trials. PD measurements collected after discontinuation were excluded.

Figure 27:
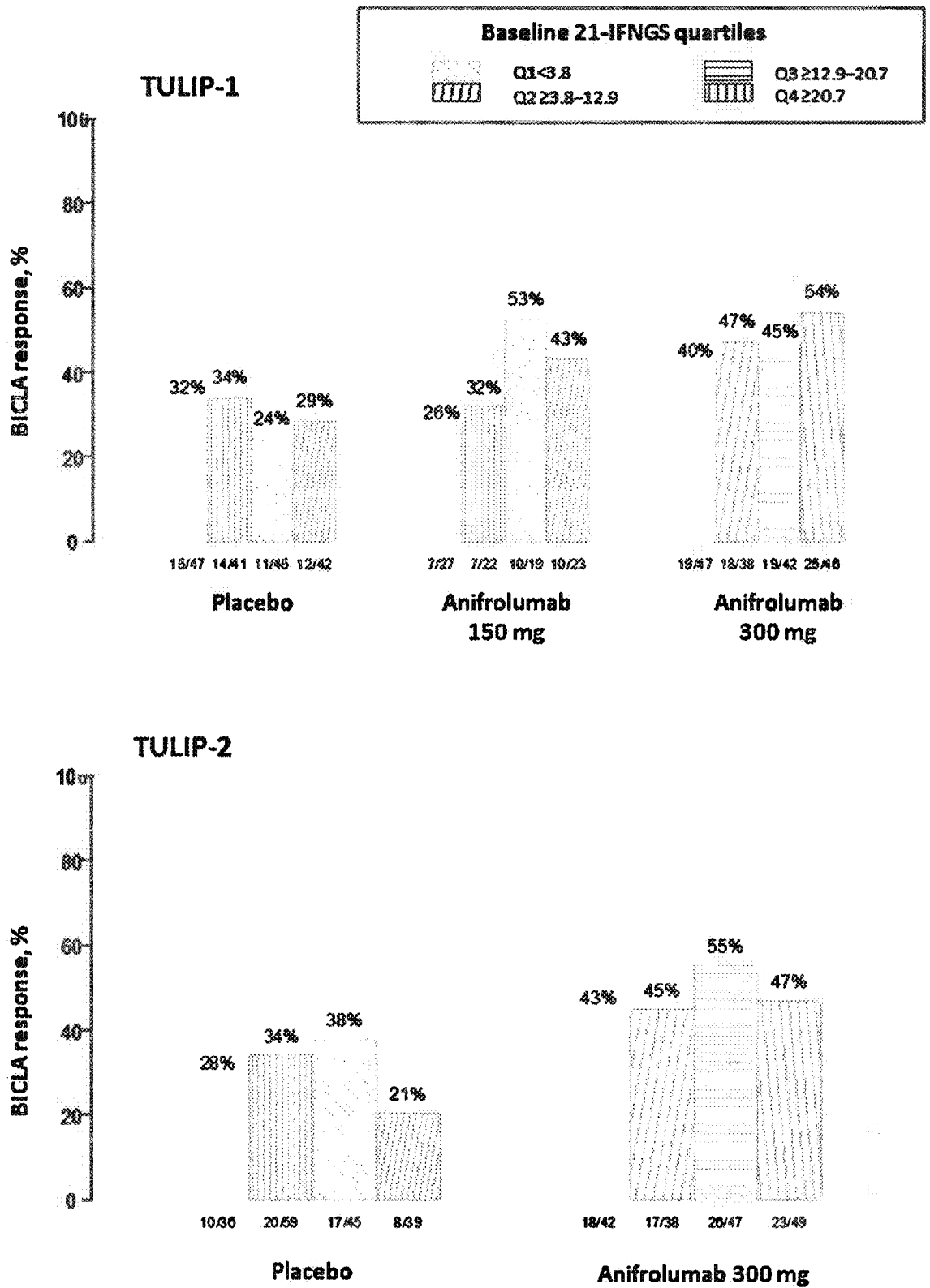

FIG. 27: BICLA Response Rate in All-Comers According to Baseline 21-IFNGS Quartiles in TULIP-1 and TULIP-2

BICLA responses were higher with anifrolumab 300 mg versus placebo across all baseline 21-IFNGS score quartiles in TULIP-1 and TULIP-2. 21-IFNGS, 21-gene pharmacodynamic interferon gene signature; BICLA, British Isles Lupus Assessment Group (BILAG)-Based Composite Lupus Assessment. Of 819 patients who received at least one dose of anifrolumab 300 mg, anifrolumab 150 mg, or placebo in the TULIP-1 and TULIP-2 trials, 25 patients (18 IFNGS-high and 7 IFNGS-low patients) were missing baseline 21-IFNGS score, and so only 794 patients were included in this analysis. The baseline 21-IFNGS quartiles were calculated based on the same population.

Figure 29A:
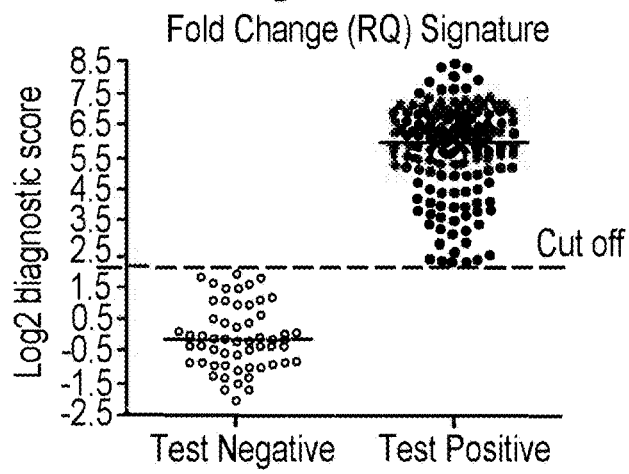
Figure 29B:
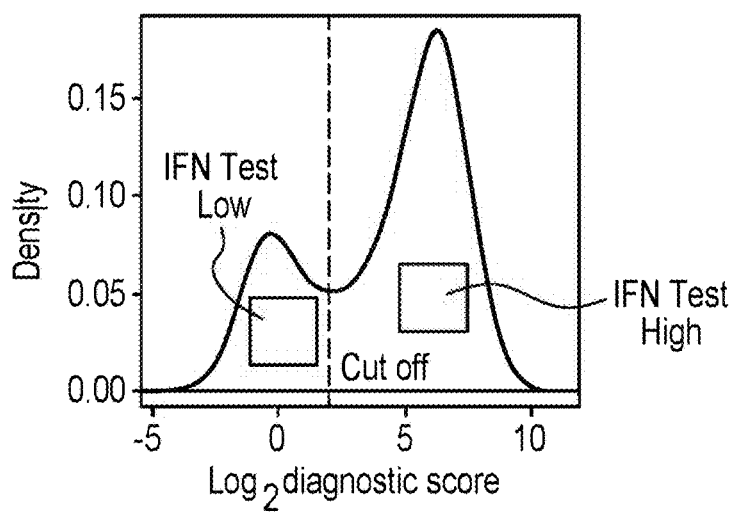
Figure 29C:
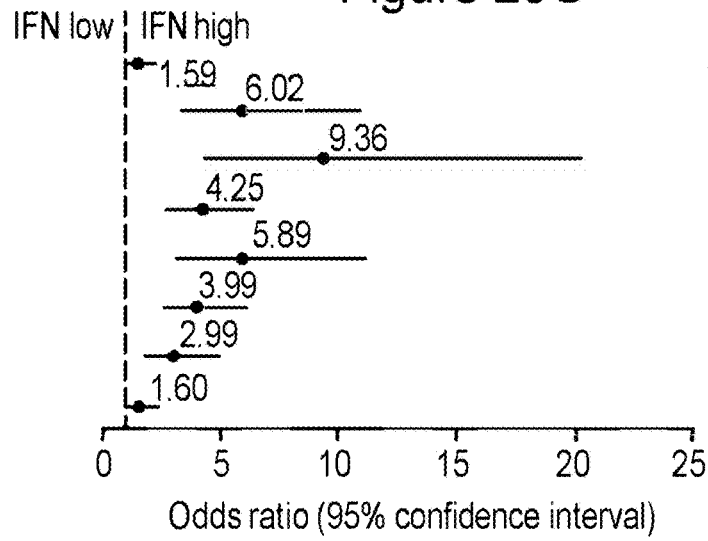

FIG. 28: 21 Interferon-α/β-Inducible Genes Constituting the 21-Gene Pharmacodynamic Interferon Gene Signature FIG. 29A-29C: Interferon gene signature (IFNGS)

There is a clear boundary between diagnostic test positive and negative patients in SLE. FIG. 29A: Fold change (RQ) signature. FIG. 29B: Distribution of transcript scores for each SLE patients. The result of the test is a score that is compared with a pre-established cut-off that classifies patients into 2 groups with low or high levels of IFN inducible gene expression. FIG. 29C: High type I IFN gene signature is associated with increased disease activity and steroid use in SLE.

Figure 30A:
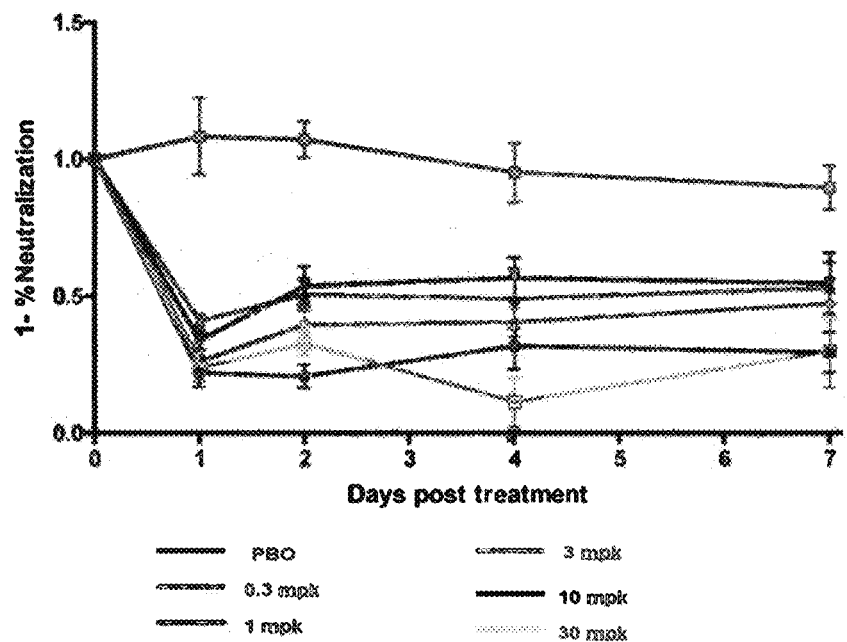
Figure 30B:
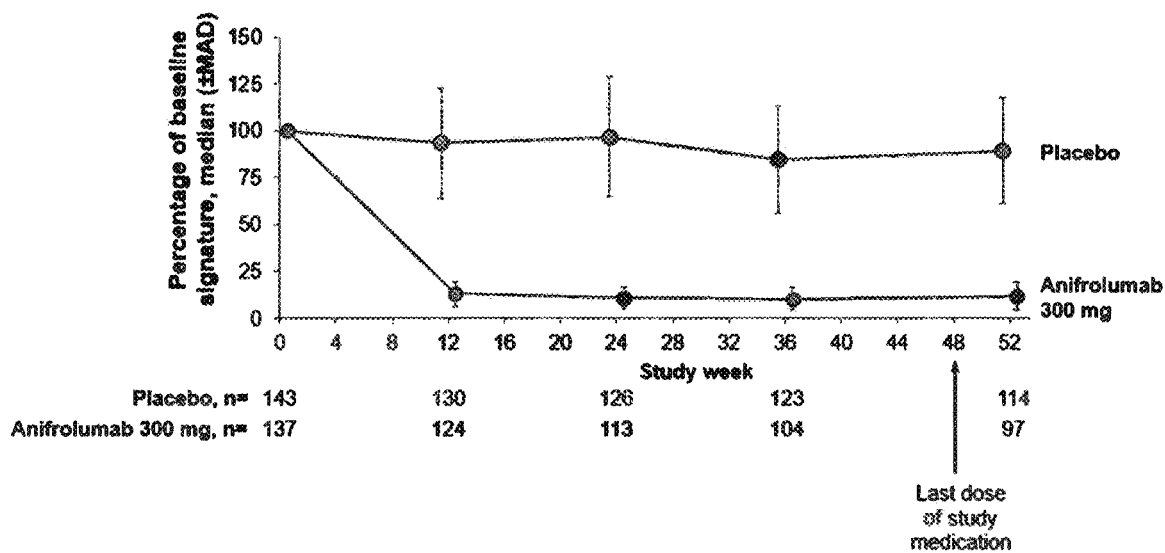

FIG. 30A-30B: IFNGS neutralization

FIG. 30A: Study CP152 of sifalimumab treatment in SLE patients. FIG. 30B: Change in type I IFNGS in patients with high baseline IFNGS. IFNGS: interferon gene signature; MAD, median absolute deviation.

Figure 31A:
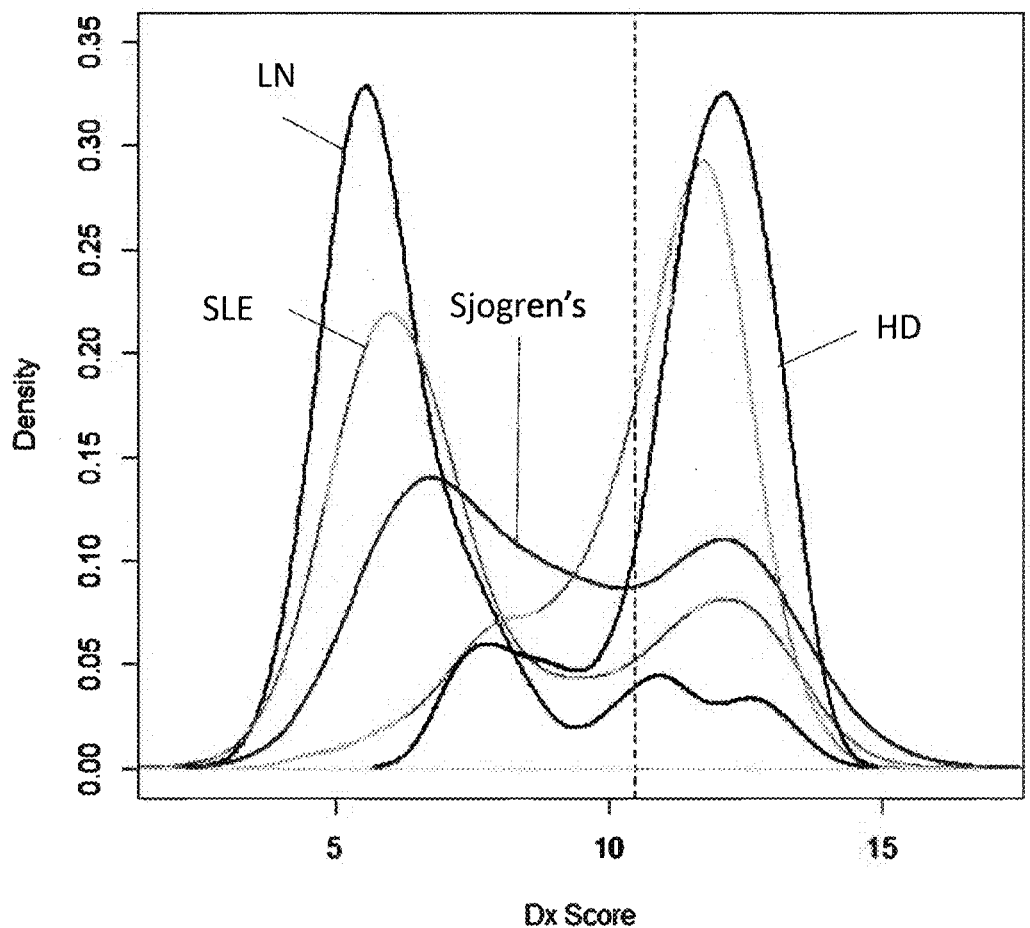
Figure 31B:
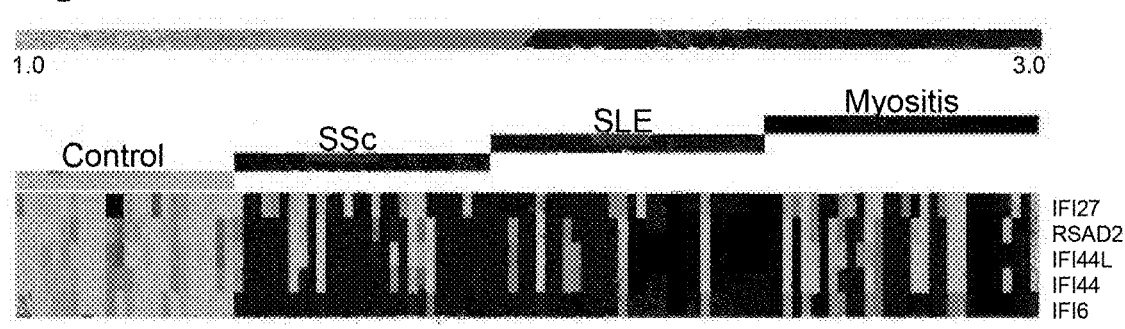

FIG. 31A-31B: Distribution of IFNGS in type I IFN mediated disease

FIG. 31A: Distribution of the IFNGS in patients with SLE, LN and Sjogren's syndrome. LN: lupus nephritis; SLE: Systemic Lupus Erythematosus; HD: healthy donor. FIG. 31B: Microarray analysis of whole blood and skin from patients in Study MI-CP180. IFN score is defined as the median fold change (FC) of 5 type I IFN-inducible genes, which were among the highest differentially regulated genes in scleroderma patients compared to healthy control. The baseline (day 0) score was used to determine if a patient was IFN signature positive or negative. The 5 genes are a subset of the 21 gene set used to measure PD in SLE.

Figure 32B:
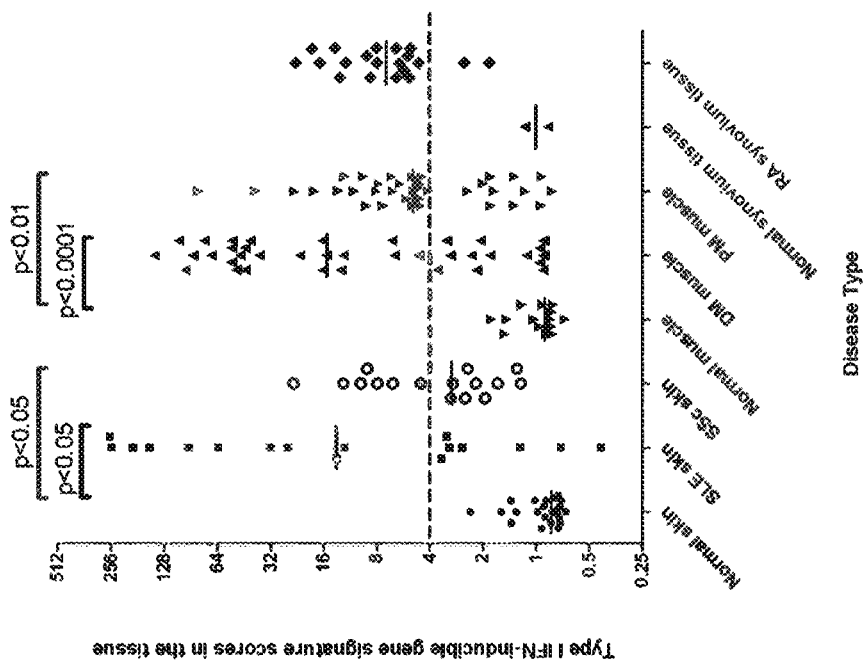
Figure 32A:
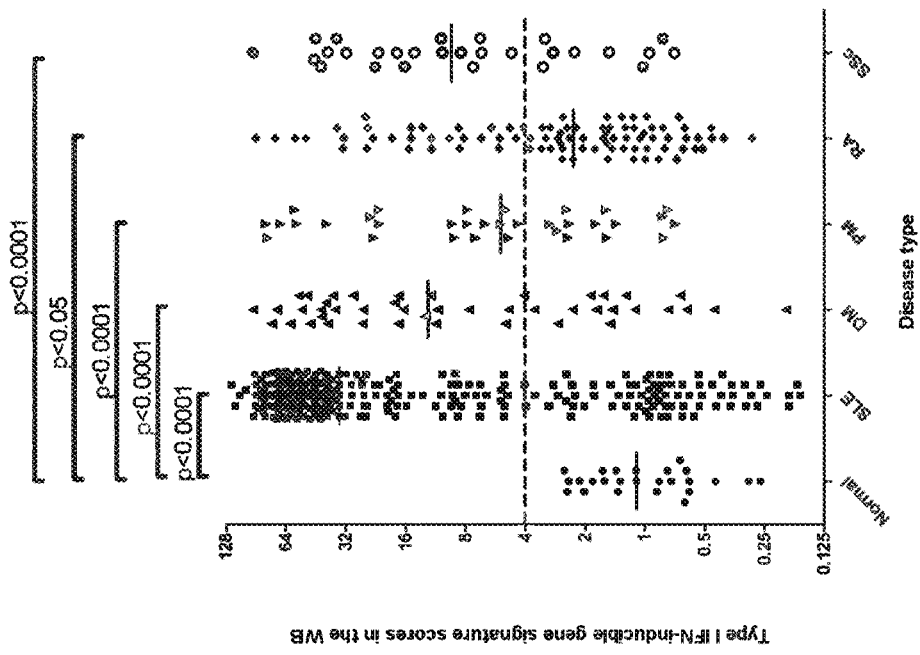

FIG. 32A-32B: Baseline gene signatures using 5-gene IFNGS

FIG. 32A: Type I IFN-inducible gene signature scores in the whole blood (WB). FIG. 32B: Type I IFN-inducible gene signature scores in the skin. 5-genes score: (IFI27, RSAD2, IFI44L, IFI44, IFI6).

Figure 33:
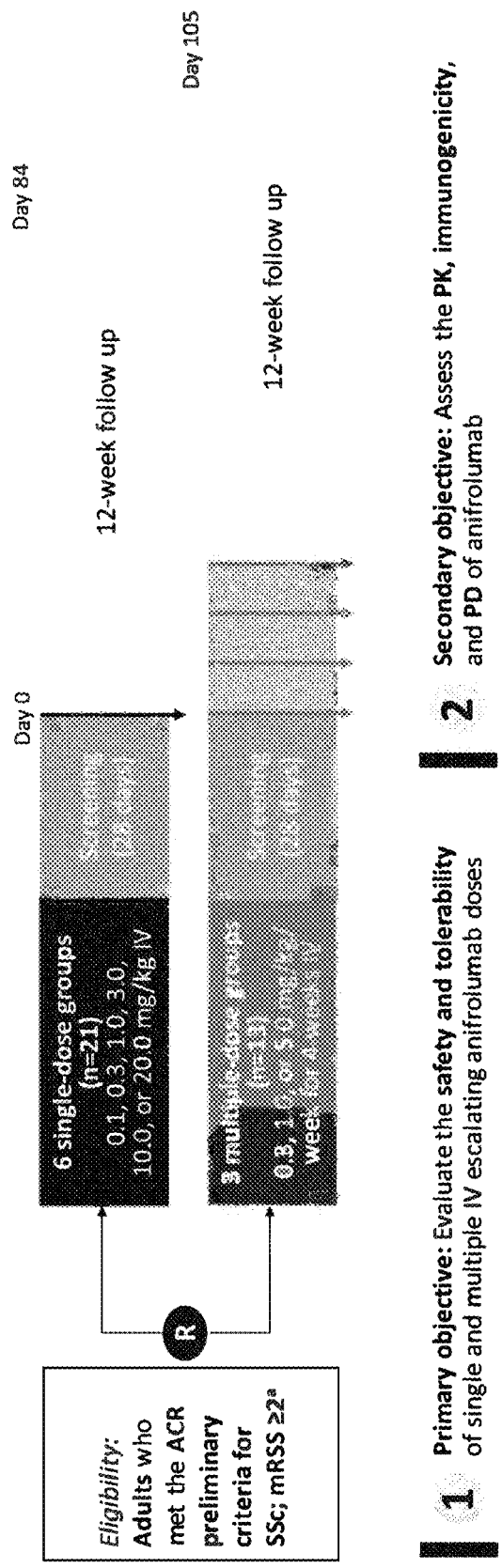

FIG. 33: Anifroluamb in SSc: Phase I study design

Multicenter, open-label dose-escalation study; 34 patients from 7 US sites (NCT00930683).

Figure 34A:
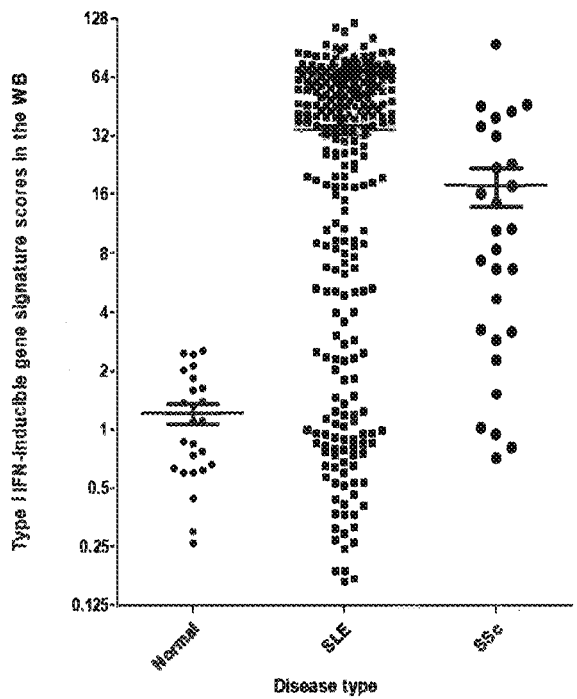
Figure 34B:
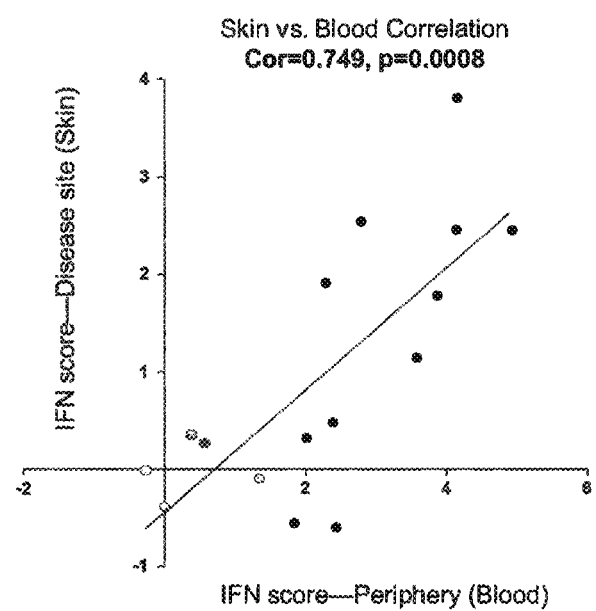
Figure 34C:
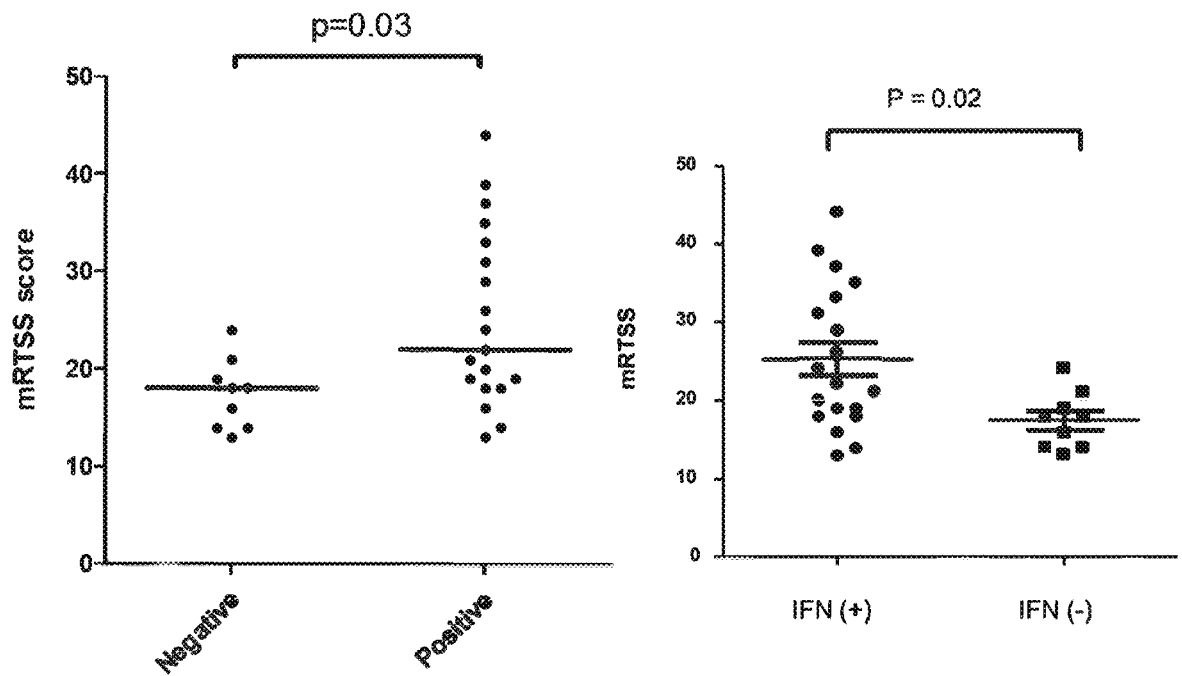

FIG. 34A-34C: Baseline type I IFN score correlates with disease activity in scleroderma patients FIG. 34A: Comparison of distribution of 5 gene signatures in SSc and SLE at baseline. FIG. 34B: IFNGS in the periphery correlates with IFNGS in disease tissue. RNA was isolated from WB and skin at baseline and the IFN score was determined by calculating the median fold change (FC) of 5

IFN-inducible genes (IFI27, IF16, IFI44, IFI44L, and RSAD2). The correlation between the periphery and disease tissue was evaluated. FIG. 34C: Baseline IFNGS correlates with disease activity score (mRTSS score). RNA was isolated from WB and skin at baseline and the IFN score was measured. Modified Rodnan total skin score (mRTSS), an assessment of disease activity in SSc, was determined by a clinician. (A) The correlation between the IFN score and mRTSS in all patients is shown. (B) mRTSS scores in IFN (+) vs. IFN (−) patients reveal a significant increase in disease activity among IFN signature (+) patients. Patients were determined to be signature (+) based on a cutoff of IFN score ≥3 in WB and IFN score ≥2 in skin.

FIG. 35: Dose-dependent neutralization of the (5-gene) IFN score in WB and skin of signature positive scleroderma patients.

Patients were given a single administration of anifrolumab at multiple dose levels. The % neutralization was calculated relative to the baseline IFN score.

Figure 36A:
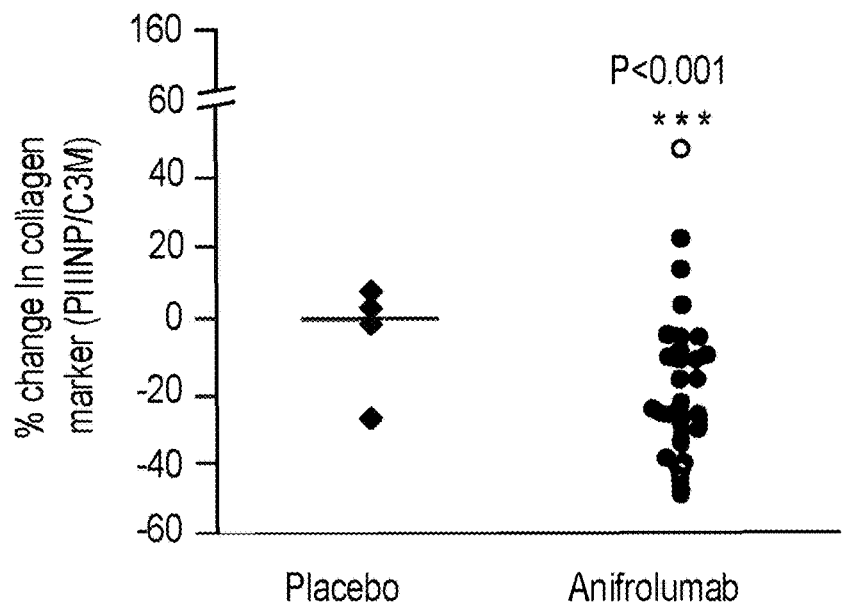
Figure 36B:
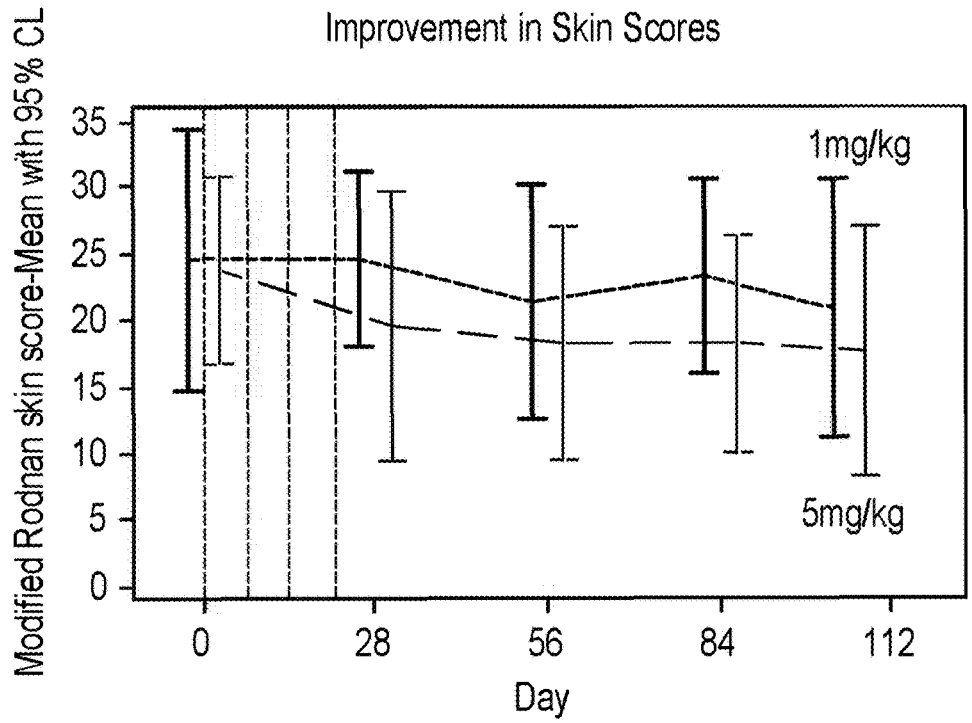

FIG. 36A-36B: Treatment effects of anifrolumab in SSc patients.

Patients were given a single administration of anifrolumab at multiple dose levels. Modulation of collagen deposition (FIG. 36A) and improvement in skin scores (FIG. 36B) were determined.

Figure 37:
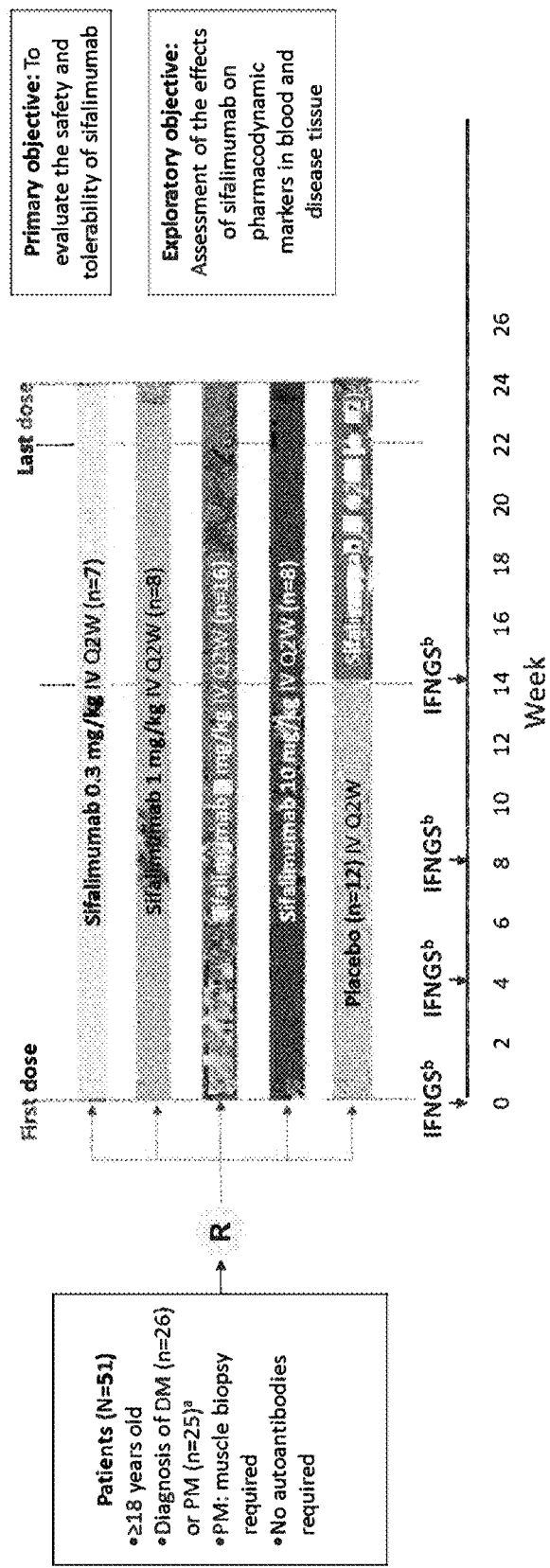

FIG. 37: Phase Ib trial of sifalimumab, an anti-IFN-α monoclonal antibody in patients with DM and PM Protocol summary for Study MI-CP151. DM, dermatomyositis; IFN, interferon; IFNGS, interferon gene signature; IV, intravenous; PM, polymyositis; Q2W, every 2 weeks; R, randomization. $^a$Evaluated with the Bohan and Peter 1975 criteria$^2$. $^b$Represents when the pharmacodynamic IFNGS measurement was performed.

Figure 38:
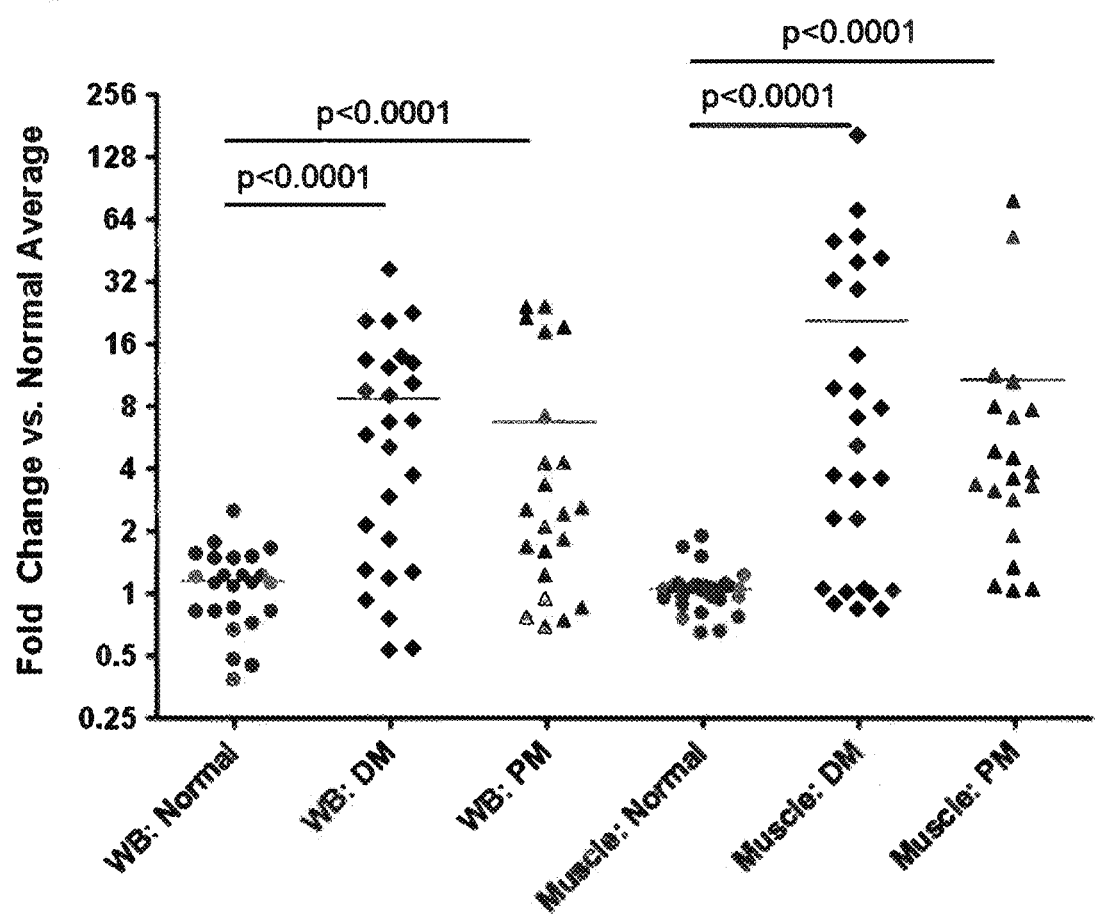

FIG. 38: IFNGS in myositis patients (Study MI-CP151)

Baseline type I IFN gene signature (13 gene score) values for DM and PM patients in muscle and blood were determined, revealing elevated IFNGS score in the whole blood and muscle of both BM and PM patients.

Figure 39A:
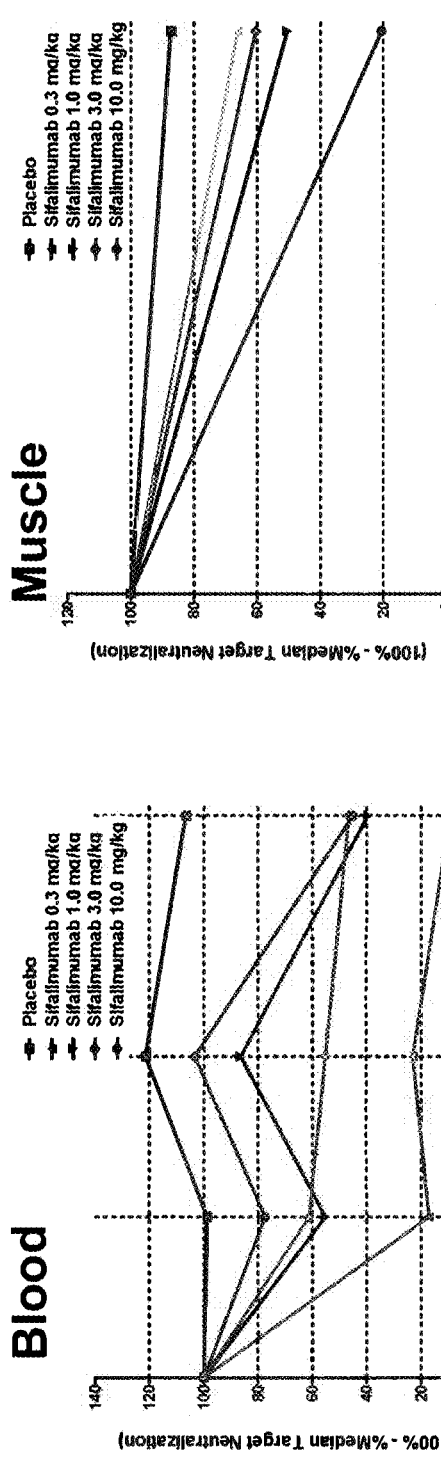
Figure 39B:
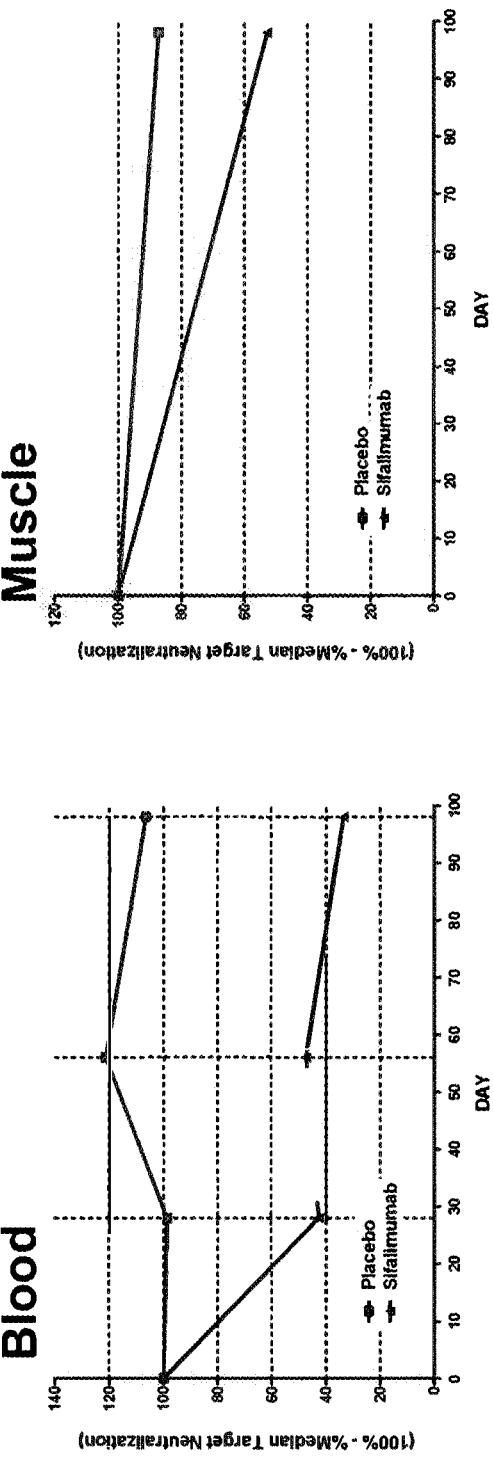

FIG. 39A-39B: Neutralization of the IFNGS in myositis patients (Study MI-CP151)

Target modulation by sifalimumab of the type I IFN gene signature in DM (FIG. 39A) or PM (FIG. 39B) patient blood and muscle in study MI-CP151.

Figure 40A:
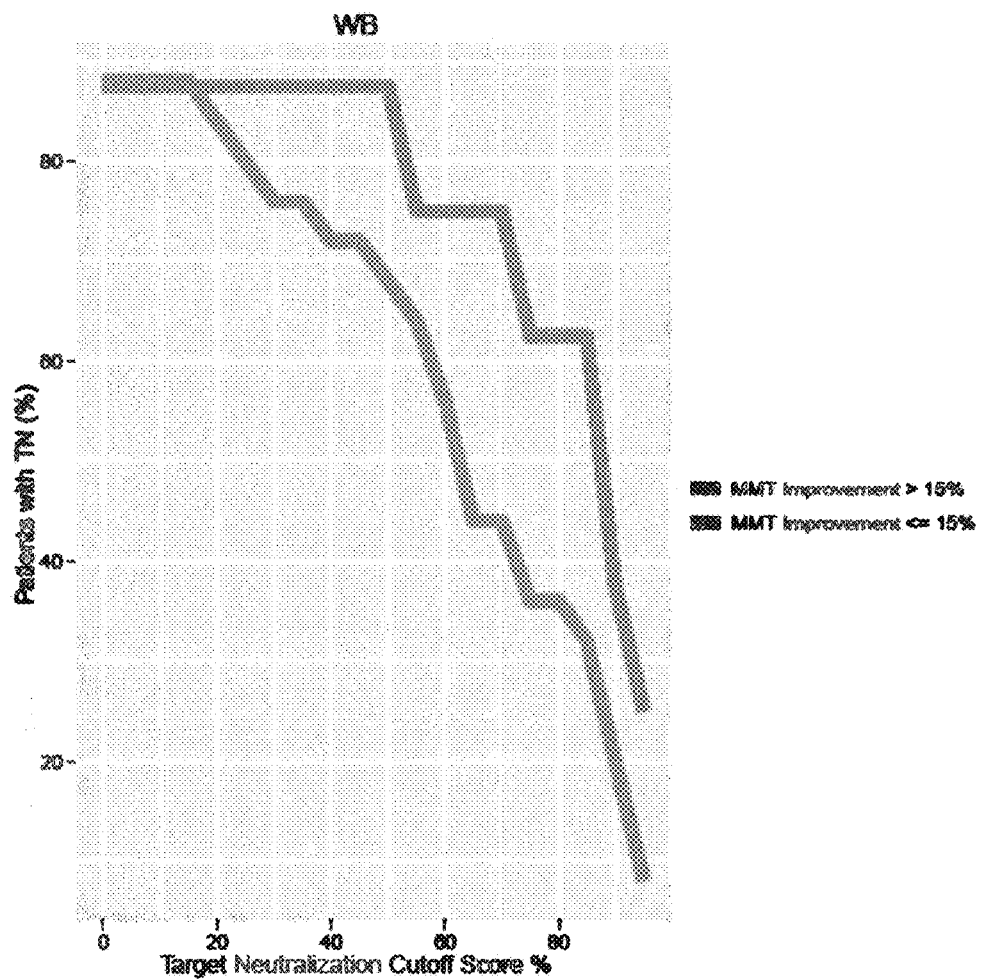
Figure 40B:
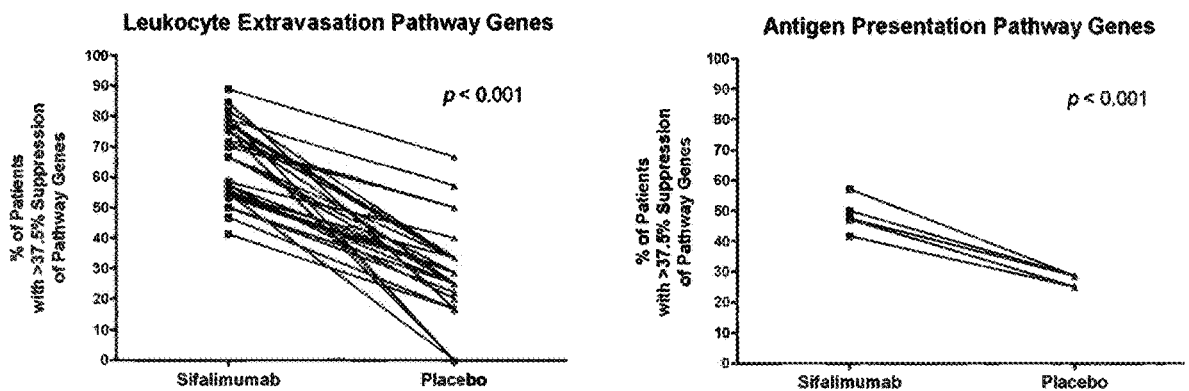

FIG. 40A-40B: Target modulation of the type I IFN gene signature in blood shows a correlative trend with disease activity in DM and PM patients (Study MI-CP151)

FIG. 40A: Stratified target neutralization curves representing the proportion of patients with DM or PM treated with sifalimumab that demonstrate suppression of their type I IFN gene signature at day 98 at the provided threshold value on the x-axis. Patients that exhibited at least 15% improvement in MMT8 score at day 98 (compared to day 0) are represented by the orange lines, while those patients that did not are represented by the blue lines. All type I IFN signature positive patients (27) treated with sifalimumab pre-dosing. FIG. 40B: Target suppression of the type I IFN gene signature is correlated with suppression of important signaling events in the muscle tissue.

Figure 41:
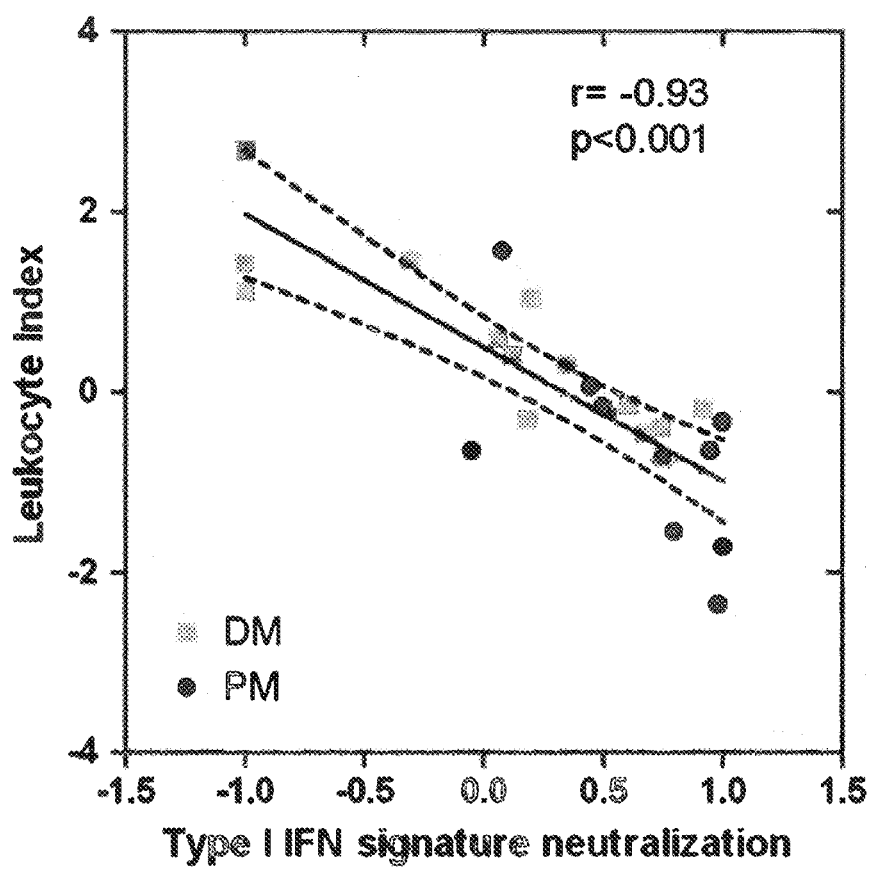

FIG. 41: IFNα inhibition reduces immune cell infiltration into myositis muscle (DM and PM) (Study Sifalimumab reduces immune cell infiltration in myositis muscle tissue of DM and PM patients.

Figure 42A:
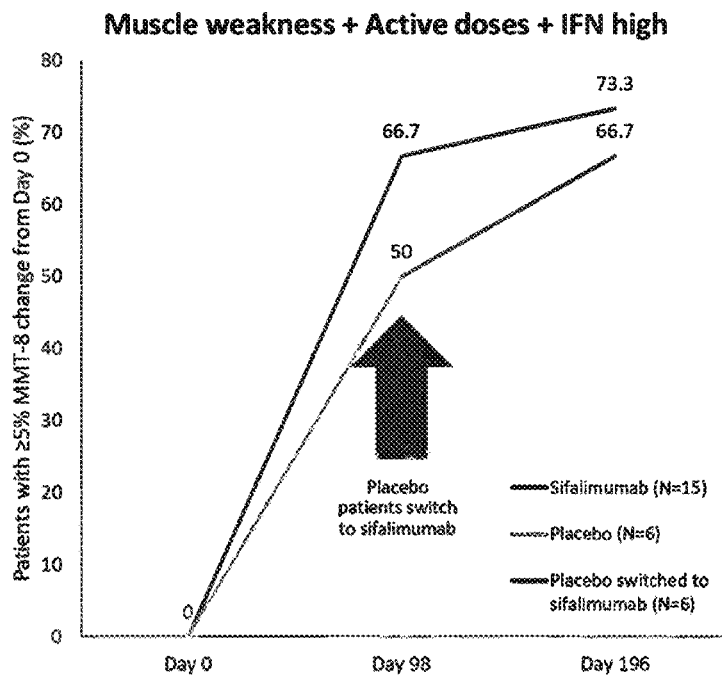
Figure 42B:
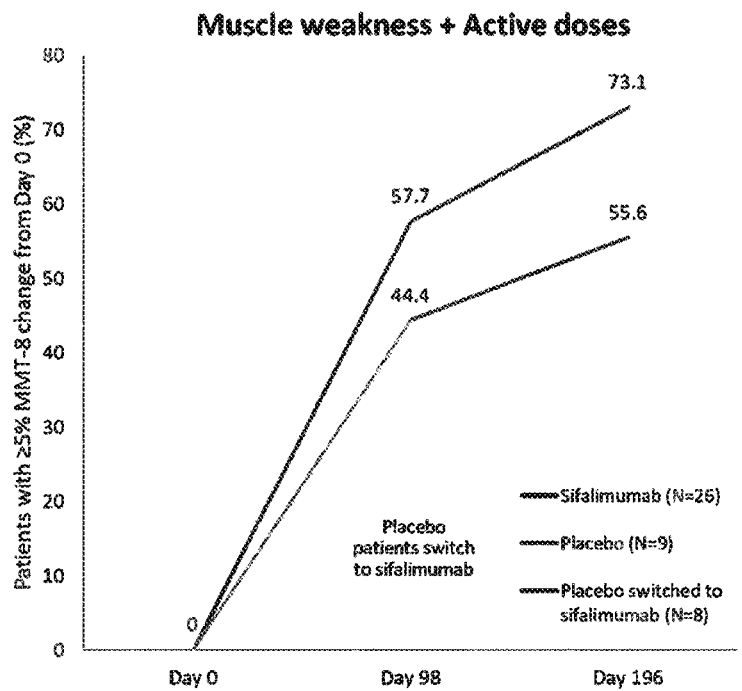

FIG. 42A-42B: Sifalimumab improves muscle strength at pharmacologically active doses Doses include 1 mg/kg, 3 mg/kg and 10 mg/kg. Sifalimumab groups: 6 months with 14 doses (Q2W). Placebo group: dosed for 3 months, then switched to sifalimumab for 3 months. Results are shown with (FIG. 42A) and without (FIG. 42B) interferon therapy.

FIG. 43: Comparison of the IFNGS neutralization effect of anifrolumab and sifalimumab Sifalimumab and anifrolumab were both tested in a phase II clinical trial in SLE (NCT01283139 and Study 1013, respectively, Table 6-1: Clinical studies). Both therapies had positive results and neutralized the type I IFN GS, with the effect size being larger for anifrolumab.

Figure 44A:
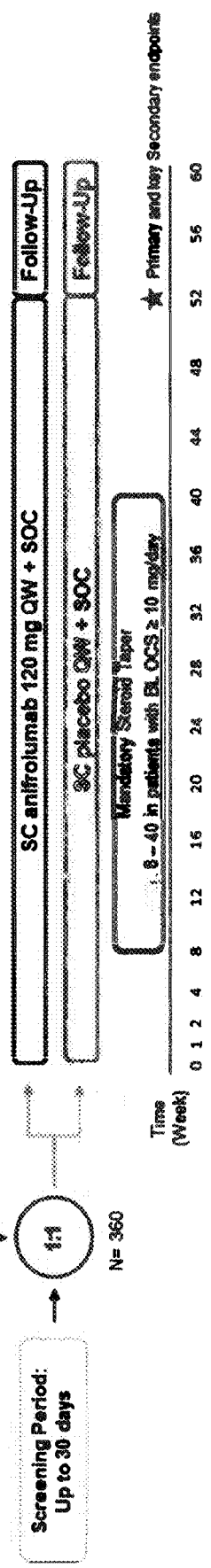
Figure 44B:
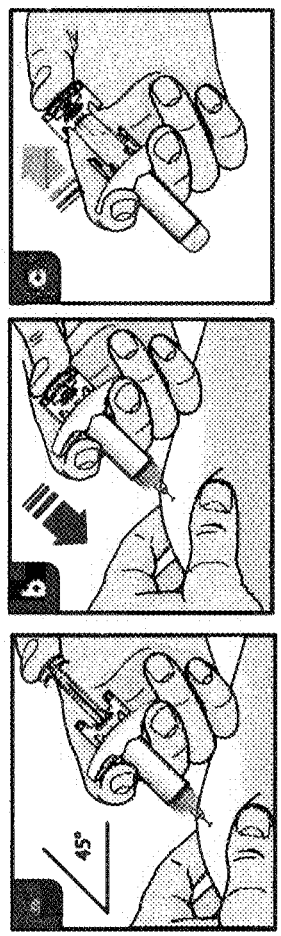
Figure 44C:
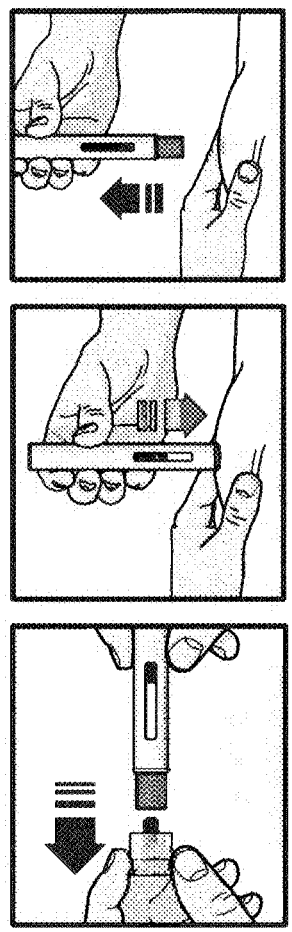

FIG. 44A-44C: Delivery device

Phase III study protocol (FIG. 44A). Anifrolumab is administered by an injection device [1] [9] such as a prefilled syringe (PFS) (FIG. 44B) or an autoinjector (FIG. 44C).

Figure 45A:
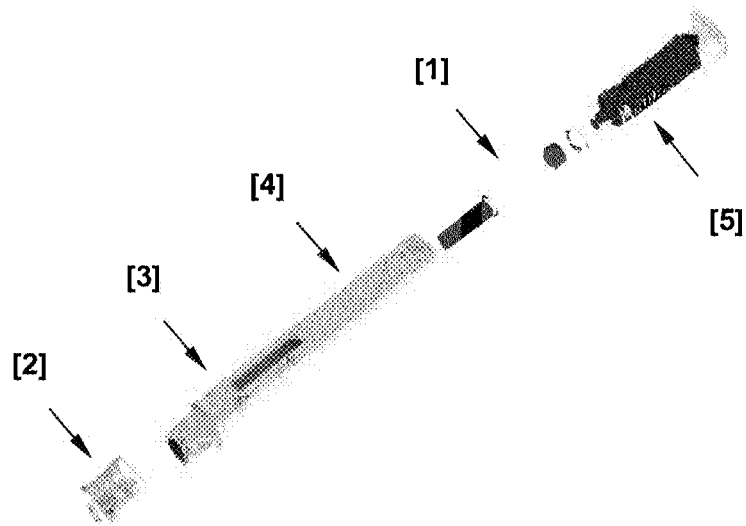
Figure 45B:
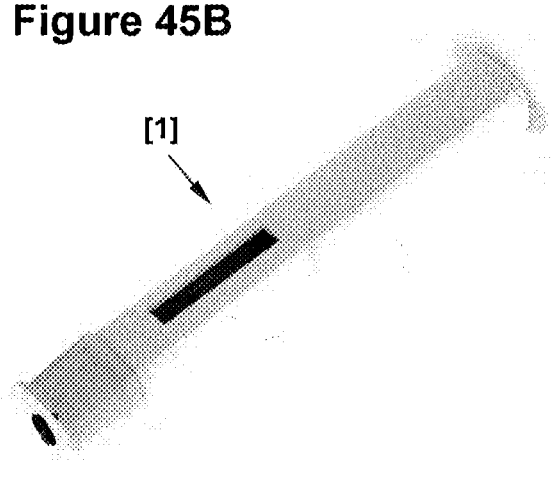
Figure 45C:
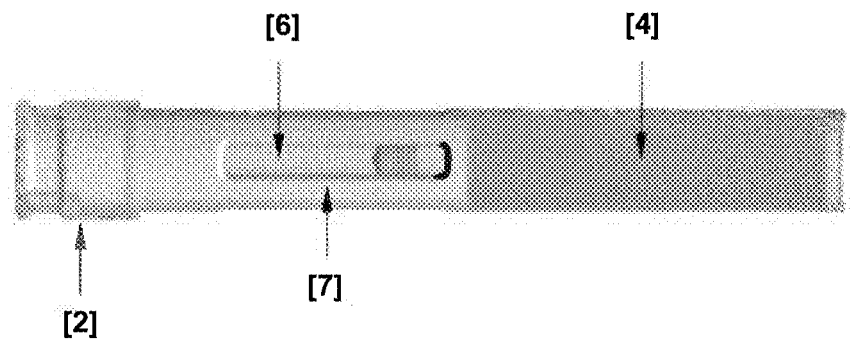

FIG. 45A-45C: Autoinjector

The autoinjector for administering anifrolumab of the functional variant thereof in exploded view (FIG. 45A), assembled (FIG. 45B) and filled with drug substance (FIG. 45C).

FIG. 46A-46D: Accessorized pre-filled syringe

Figure 46A:
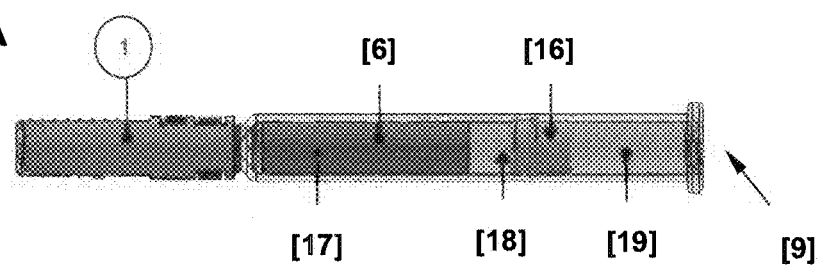
Figure 46B:
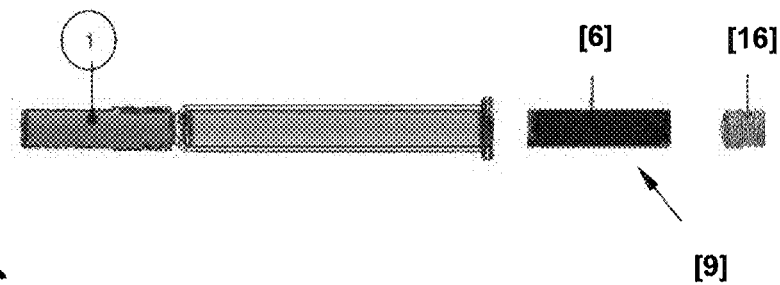
Figure 46C:
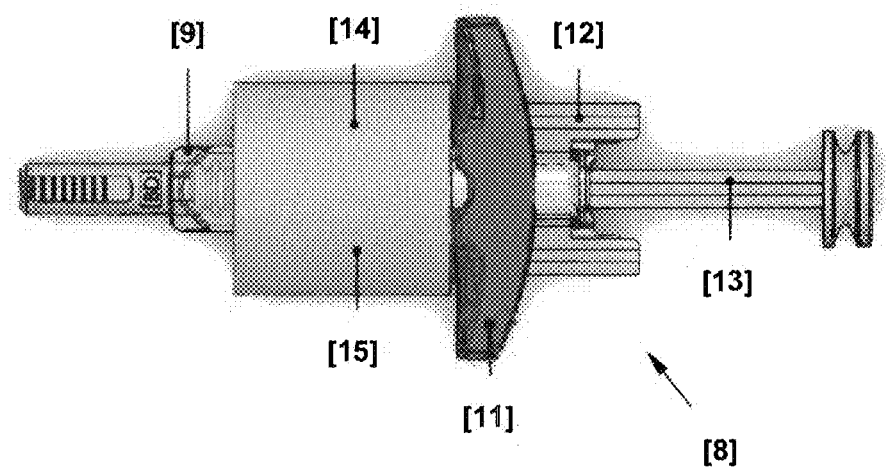
Figure 46D:
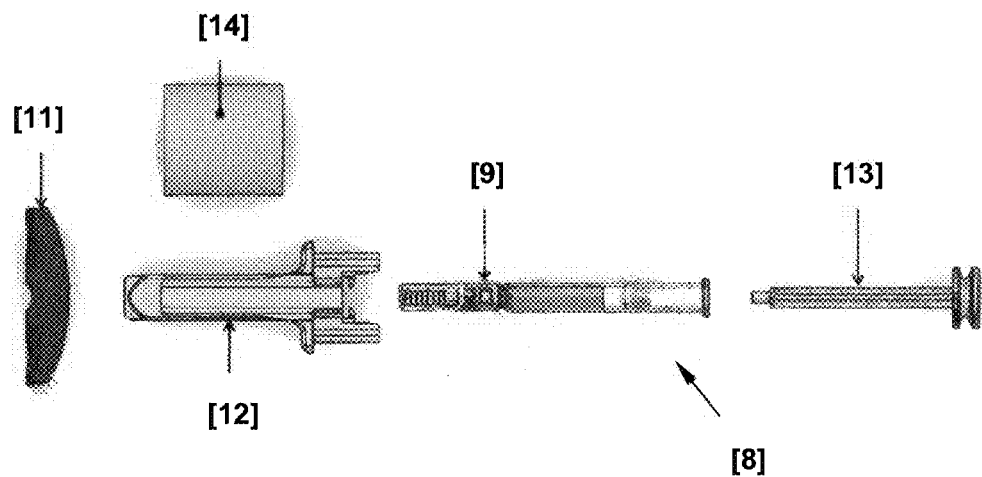

The accessorized pre-filled syringe (APFS) for anifrolumab of the functional variant thereof. The primary tube is shown in assembled form (FIG. 46A) and in exploded view (FIG. 46B). The APFS with its additional components is shown in assembled form (FIG. 46C) and in exploded view (FIG. 46D).

Figure 47:
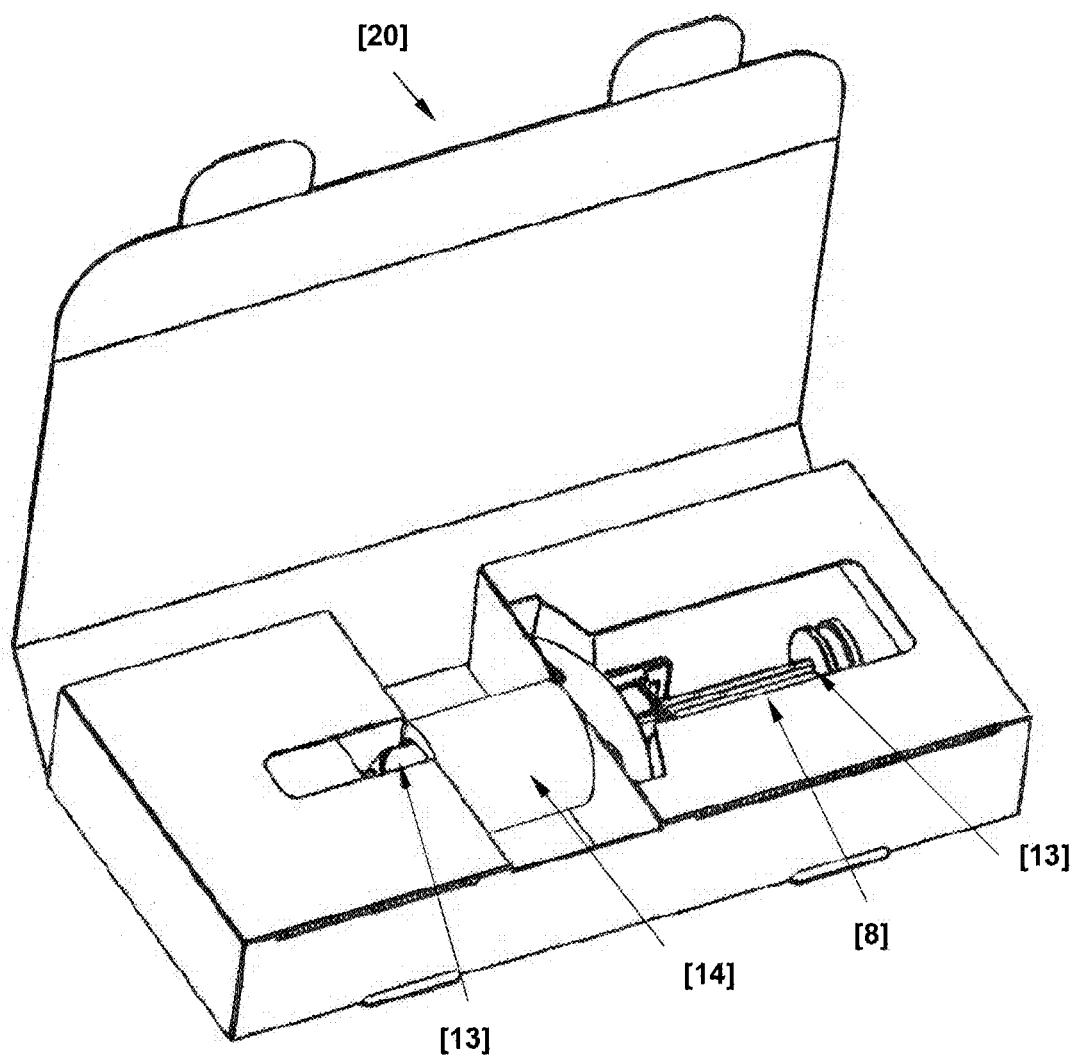

FIG. 47: Packaging for the delivery device
FIG. 48. Anifrolumab Heavy Chain alignment
FIG. 49. Anifrolumab Light Chain alignment

4. DETAILED DESCRIPTION

4.1. Subcutaneous Unit Dose

The present invention relates to a unit dose (pharmaceutical unit dose, unit dose form or pharmaceutical unit dose form) for subcutaneous administration comprising >105 mg (i.e. more than 105 mg) and <150 mg (i.e. less than 150 mg) anifrolumab or a functional variant thereof. The unit dose may be packaged or formulated as a unit dose, i.e. for administration in a single administration step to a subject.

The present invention relates to a unit dose (pharmaceutical unit dose, unit dose form or pharmaceutical unit dose form) for subcutaneous administration comprising >105 mg (i.e. more than 105 mg) and <150 mg (i.e. less than 150 mg) of a IFNAR1 inhibitor. The unit dose may be packaged or formulated as a unit dose, i.e. for administration in a single administration step to a subject.

The unit dose may comprise ≤135 mg (i.e. 135 mg or less) of the IFNAR1 inhibitor. The unit dose may comprise about 120 mg of the IFNAR1 inhibitor. The unit dose may comprise 120 mg of the IFNAR1 inhibitor. The unit dose may consist essentially of >105 mg and <150 mg of the IFNAR1 inhibitor. The unit dose may consist essentially of ≤135 mg of the IFNAR1 inhibitor. The unit dose may consist essentially of about 120 mg of the IFNAR1 inhibitor. The concentration of the IFNAR1 inhibitor in the unit dose may be about 150 mg/ml. The volume of the unit dose may be less than 1 ml. The dose or unit dose may have a volume of 0.5 to 1 ml. The concentration of the unit dose may be about 0.8 ml. The volume of the unit dose may be 0.8 ml. The unit dose may comprise a formulation of 150 to 200 mg/ml anifrolumab or the functional variant thereof, 25 to 150 mM of a lysine salt and an uncharged excipient. The unit dose may comprise a formulation of 150 to 200 mg/ml of the IFNAR1 inhibitor, 25 to 150 mM of a lysine salt and an uncharged excipient. The unit dose comprises a formulation of 25 mM histidine-HCL, 130 mM trehalose, and 0.05% w/v polysorbate 80. The formulation may have a pH of about 5.9.

The unit dose may comprise ≤135 mg (i.e. 135 mg or less) anifrolumab or the functional variant thereof. The unit dose may comprise about 120 mg anifrolumab or the functional variant thereof. The unit dose may comprise 120 mg anifrolumab or the functional variant thereof. The unit dose may consist essentially of >105 mg and <150 mg anifrolumab or the functional variant thereof. The unit dose may consist essentially of ≤135 mg anifrolumab or the functional variant thereof. The unit dose may consist essentially of about 120 mg anifrolumab or the functional variant thereof. The concentration of anifrolumab or the functional variant thereof in the unit dose may be about 150 mg/ml. The volume of the unit dose may be less than 1 ml. The dose or unit dose may have a volume of 0.5 to 1 ml. The concentration of the unit dose may be about 0.8 ml. The volume of the unit dose may be 0.8 ml. The unit dose may comprise a formulation of 150 to 200 mg/ml anifrolumab or the functional variant thereof, 25 to 150 mM of a lysine salt and an uncharged excipient. The unit dose may comprise a formulation of 150 to 200 mg/ml anifrolumab or the functional variant thereof, 25 to 150 mM of a lysine salt and an uncharged excipient. The unit dose comprises a formulation of 25 mM histidine-HCL, 130 mM trehalose, and 0.05% w/v polysorbate 80. The formulation may have a pH of about 5.9.

4.2. Method of Treating a Type I IFN-Mediated Disease

The invention also relates to a method for treating a type I interferon (IFN)-mediated disease in a subject, the method of treatment comprising subcutaneously administering the unit dose of the invention to a subject having a type I interferon (IFN)-mediated disease. The invention also relates to a method of treating a type I IFN-mediated disease in a subject, the method comprising subcutaneously administering a dose of a IFNAR1 inhibitor, wherein the dose is >105 mg and <150 mg. The invention also relates to a method of treating a type I IFN-mediated disease in a subject, the method comprising subcutaneously administering a dose of anifrolumab or a functional variant thereof, wherein the dose is >105 mg and <150 mg.

The invention also relates to a method of treating a type I IFN-mediated disease in a subject, the method comprising subcutaneously administering a dose of an IFNAR1 inhibitor, wherein administering the dose every week provides a plasma concentration in the subject that is at least equivalent to the plasma concentration provided by intravenous administration of 300 mg of the IFNAR1 inhibitor every 4 weeks. Administering the dose every week may provide a plasma concentration in the subject that is more than the plasma concentration provided by intravenous administration of 300 mg of the IFNAR1 inhibitor every 4 weeks. Administering the dose every week may provide a plasma concentration in the subject that is at least equivalent to the plasma concentration provided by intravenous administration of 400 mg of the IFNAR1 inhibitor every 4 weeks. The dose may be administered in a single-administration step. The dose administered to the subject may be <150 mg (i.e. less than 150 mg) of the IFNAR1 inhibitor. The dose administered to the subject may be >105 mg (i.e. more than 105 mg) of the IFNAR1 inhibitor. The dose administered to the subject may be ≤135 mg (i.e. 135 mg or less) of the IFNAR1 inhibitor. The dose administered to the subject may be about 120 mg of the IFNAR1 inhibitor.

The invention also relates to a method of treating a type I IFN-mediated disease in a subject, the method comprising subcutaneously administering a dose of anifrolumab or a functional variant thereof, wherein administering the dose every week provides a plasma concentration in the subject that is at least equivalent to the plasma concentration provided by intravenous administration of 300 mg of anifrolumab or the functional variant thereof every 4 weeks. Administering the dose every week may provide a plasma concentration in the subject that is more than the plasma concentration provided by intravenous administration of 300 mg of anifrolumab or the functional variant thereof every 4 weeks. Administering the dose every week may provide a plasma concentration in the subject that is at least equivalent to the plasma concentration provided by intravenous administration of 400 mg of anifrolumab or the functional variant thereof every 4 weeks. The dose may be administered in a single-administration step. The dose administered to the subject may be <150 mg (i.e. less than 150 mg) anifrolumab or the functional variant thereof. The dose administered to the subject may be >105 mg (i.e. more than 105 mg) anifrolumab or the functional variant thereof. The dose of administered to the subject may be ≤135 mg (i.e. 135 mg or less) anifrolumab or the functional variant thereof. The dose administered to the subject may be about 120 mg anifrolumab or the functional variant thereof.

The type I IFN-mediated disease may be lupus. The type I IFN-mediated disease may be systemic lupus erythematosus (SLE). Administration of the dose or unit dose may provide an improvement of the patient's BILAG-Based Composite Lupus Assessment (BICLA) response rate from baseline. Administration of the dose or unit dose may cause the subject to have a BICLA response, where a BICLA response is defined as (1) at least one gradation of improvement in baseline BILAG scores in all body systems with moderate or severe disease activity at entry (e.g., all A (severe disease) scores falling to B (moderate), C (mild), or D (no activity) and all B scores falling to C or D); (2) no new BILAG A or more than one new BILAG B scores; (3) no worsening of total SLEDAI score from baseline; (4) no significant deterioration (≤10%) in physicians global assessment; and (5) no treatment failure (initiation of non-protocol treatment). Administration of the dose or unit dose may provide an improvement of the patient's Systemic Lupus Erythematosus Responder Index (SRI)4 score from baseline. A subject achieves SRI(4) if all of the following criteria are met: 1. reduction from baseline of ≥4 points in the SLEDAI-2K; 2. no new organ system affected as defined by 1 or more BILAG-2004 A or 2 or more; 3. BILAG-2004 B items compared to baseline using BILAG-2004; 4. no worsening from baseline in the subjects' lupus disease activity defined by an increase ≥0.30 points on a 3-point PGA VAS. Lupus includes SLE, lupus nephritis and cutaneous lupus erythematosus (CLE).

The method of treatment may reduce SLE disease activity in the subject. Reducing SLE disease activity in the subject may comprise a) a BILAG-Based Composite Lupus Assessment (BICLA) response in the subject, b) an SRI(4) response in the subject, and/or reducing the subject's Cutaneous Lupus Erythematosus Disease Area and Severity Index (CLASI) score compared to the subject's CLASI score pre-treatment.

The type I IFN-mediated disease may be an autoimmune disease. The type I IFN-mediated disease may be myositis. The type I IFN-mediated disease may be Sjogren's syndrome. The type I IFN-mediated disease may be scleroderma.

A type I IFN-mediated disease may be defined as a disease wherein the patient has an elevated IFNGS compared to a healthy donor. The elevated IFNGS may be in the patient's whole blood and/or diseased tissue (e.g. muscle and/or skin). The elevated IFNGS may be measured as a 4-gene, 5-gene or 21-gene score.

4.3. Doses

A unit dose (also referred to as a unit dose form, a pharmaceutical unit dose or a pharmaceutical unit dose form) is a dose formed from a single unit. A unit dose (unit dose form) is suitable for administration to a subject in a single administration step. A unit dose (unit dose form) may be packaged in a single-unit container, for example a single-use pre-filled syringe or autoinjector. Unit doses provide the advantage that they can be ordered, packaged, handled and administered as single dose units containing a pre-determined amount of a drug. Unit doses decrease administration errors and reduce waste.

In another aspect the present invention relates to a unit dose (pharmaceutical unit dose, unit dose form or pharmaceutical unit dose form) for subcutaneous administration comprising >105 mg (i.e. more than 105 mg) and <150 mg (i.e. less than 150 mg) of an IFNAR1 inhibitor. The unit dose may comprise 105 to 149 mg of an IFNAR inhibitor.

In another aspect the present invention relates to a unit dose (pharmaceutical unit dose, unit dose form or pharmaceutical unit dose form) for subcutaneous administration comprising >105 mg (i.e. more than 105 mg) and <150 mg (i.e. less than 150 mg) anifrolumab or a functional variant thereof.

The unit dose may comprise ≤135 mg (i.e. 135 mg or less) of the IFNAR1 inhibitor. The unit dose may comprise 105 mg to 135 mg of an IFNAR inhibitor. The unit dose may comprise about 120 mg of the IFNAR1 inhibitor. The unit dose may comprise 120 mg of the IFNAR1 inhibitor. The unit dose may consist essentially of >105 mg and <150 mg of the IFNAR1 inhibitor. The unit dose may consist essentially of ≤135 mg of the IFNAR1 inhibitor. The unit dose may consist essentially of about 120 mg anifrolumab or the or the functional variant thereof. The concentration of the IFNAR1 inhibitor in the unit dose may be about 150 mg/ml. The volume of the unit dose may be 1 ml or less. The dose or unit dose may have a volume of 0.5 to 1 ml. The concentration of the unit dose may be about 0.8 ml. The volume of the unit dose may be 0.8 ml. The unit dose may comprise a formulation of 150 to 200 mg/ml the IFNAR1 inhibitor, 25 to 150 mM of a lysine salt and an uncharged excipient. The unit dose may comprise a formulation of 150 to 200 mg/ml the IFNAR1 inhibitor, 25 to 150 mM of a lysine salt and an uncharged excipient. The unit dose comprises a formulation of 25 mM histidine-HCL, 130 mM trehalose, and 0.05% w/v polysorbate 80. The formulation may have a pH of about 5.9.

In another aspect the invention relates to a method for treating lupus (e.g. SLE) in a subject, the method of treatment comprising subcutaneously administering the unit dose of the invention a subject having lupus (e.g. SLE). In another aspect the invention relates to a method of treating a lupus (e.g. SLE) in a subject, the method comprising subcutaneously administering a dose of anifrolumab or a functional variant thereof, wherein the dose is >105 mg and <150 mg. In another aspect the invention relates to a method of treating a lupus (e.g. SLE) in a subject, the method comprising subcutaneously administering a dose of anifrolumab or a functional variant thereof, wherein the dose 105 mg to 149 mg.

In another aspect the invention relates to a method of treating lupus (e.g. SLE) in a subject, the method comprising subcutaneously administering a dose of an IFNAR1 inhibitor, wherein administering the dose every week provides a plasma concentration in the subject that is at least equivalent to the plasma concentration provided by intravenous administration of 300 mg of the IFNAR1 inhibitor every 4 weeks. Administering the dose every week may provide a plasma concentration in the subject that is more than the plasma concentration provided by intravenous administration of 300 mg of anifrolumab or the functional variant thereof every 4 weeks. Administering the dose every week may provide a plasma concentration in the subject that is at least equivalent to the plasma concentration provided by intravenous administration of 400 mg of the IFNAR1 inhibitor every 4 weeks. The dose may be administered in a single-administration step. The dose administered to the subject may be <150 mg (i.e. less than 150 mg) the IFNAR1 inhibitor. The dose administered to the subject may be >105 mg (i.e. more than 105 mg) the IFNAR1 inhibitor. The dose of administered to the subject may be ≤135 mg (i.e. 135 mg or less) the IFNAR1 inhibitor. The dose of administered to the subject may be 105 mg to 135 mg of the IFNAR1 inhibitor. The dose administered to the subject may be about 120 mg the IFNAR1 inhibitor.

In another aspect the invention relates to a method of treating lupus (e.g. SLE) in a subject, the method comprising subcutaneously administering a dose of anifrolumab or a functional variant thereof, wherein administering the dose every week provides a plasma concentration in the subject that is at least equivalent to the plasma concentration provided by intravenous administration of 300 mg of anifrolumab or the functional variant thereof every 4 weeks. Administering the dose every week may provide a plasma concentration in the subject that is more than the plasma concentration provided by intravenous administration of 300 mg of anifrolumab or the functional variant thereof every 4 weeks. Administering the dose every week may provide a plasma concentration in the subject that is at least equivalent to the plasma concentration provided by intravenous administration of 400 mg of anifrolumab or the functional variant thereof every 4 weeks. The dose may be administered in a single-administration step. The dose administered to the subject may be <150 mg (i.e. less than 150 mg) anifrolumab or the functional variant thereof. The dose administered to the subject may be >105 mg (i.e. more than 105 mg) anifrolumab or the functional variant thereof. The dose administered to the subject may be 105 mg to 149 mg anifrolumab or the functional variant thereof. The dose of administered to the subject may be 105 mg to 135 mg anifrolumab or the functional variant thereof. The dose administered to the subject may be about 120 mg anifrolumab or the functional variant thereof.

The methods of the invention may comprise administering the dose or unit dose at intervals of 6-8 days. The dose or unit dose may be administered once per week (QW). The dose or unit dose may be 120 mg anifrolumab or the functional variant thereof, wherein the method comprises administering the dose in a single administration step once per week (QW). In other words, the method comprises administering 120 mg QW of anifrolumab of the functional variant thereof. The dose or unit dose may be administered once per week for at least about 4 weeks. The dose or unit dose may be administered once per week for at least about 8 weeks. The dose or unit dose may be administered once per week for at least about 12 weeks. The dose or unit dose may be administered once per week for at least about 16 weeks. The dose or unit dose may be administered once per week for at least about 20 weeks. The dose or unit dose may be administered once per week for at least about 24 weeks. The dose or unit dose may be administered once per week for at least about 28 weeks. The dose or unit dose may be administered once per week for at least about 32 weeks. The dose or unit dose may be administered once per week for about 8 weeks. The dose or unit dose may have a volume permitted it suitable delivery in a single subcutaneous administration step. The dose or unit dose may have a volume of 0.5 to 1 ml. The dose or unit dose may have a volume of less than 1 ml. The dose or unit dose may have a volume of about 0.8 ml.

Administration of the dose or unit dose may provide a plasma concentration of anifrolumab or the functional variant thereof in the patient of ≥10 μg (i.e. 10 μg or more) anifrolumab or the functional variant thereof per ml of plasma (i.e. a plasma concentration of ≥10 μg/ml). Administration of the dose or unit dose may provide a plasma concentration of anifrolumab or the functional variant thereof in the subject of about 10-100 μg/ml. Administration of the dose or unit dose may provide a plasma concentration of anifrolumab or the functional variant thereof in the subject of 20-80 μg/ml. Administration of the dose or unit dose may provide a plasma concentration of anifrolumab or the functional variant thereof in the subject of 30-70 μg/ml. Administration of the dose or unit dose may provide a trough concentration of anifrolumab or the functional variant thereof in the subject of ≥20 μg/ml (i.e. 20 μg/ml or more). Administration of the dose or unit dose may provide a trough concentration of anifrolumab or the functional variant thereof in the subject of ≥30 μg/ml (i.e. 30 μg/ml or more). Administration of the dose or unit dose may provide a trough concentration of anifrolumab or the functional variant thereof in the subject of ≥40 μg/ml (i.e. 40 μg/ml or more). Administration of the dose or unit dose may provide a trough concentration of anifrolumab or the functional variant thereof in the subject of 20-100 μg/ml. Administration of the dose or unit dose may provide a trough concentration of anifrolumab or the functional variant thereof in the subject of about 30-80 μg/ml. Administration of the dose or unit dose may provide a trough concentration of anifrolumab or the functional variant thereof in the subject of 40-70 μg/ml.

The dose or unit dose may provide a therapeutic effect in the subject that is at least equivalent to a therapeutic effect provided by administration of an intravenous dose of 300 mg anifrolumab or the functional variant thereof administered once every (Q4W). The dose or unit dose may provide a trough concentration of anifrolumab or the functional variant thereof in the subject that is greater than a trough concentration of anifrolumab or the functional variant thereof provided by administration of an intravenous dose of 300 mg anifrolumab or the functional variant thereof once every 4 weeks (Q4W).

The methods of the invention may comprise administering the dose or unit dose at intervals of 6-8 days. The dose or unit dose may be administered once per week (QW). The dose or unit dose may be 120 mg anifrolumab or the functional variant thereof, wherein the method comprises administering the dose in a single administration step once per week (QW). In other words, the method comprises administering 120 mg QW of anifrolumab of the functional variant thereof. The dose or unit dose may be administered once per week for at least 4 weeks. The dose or unit dose may be administered once per week for at least 8 weeks. The dose or unit dose may be administered once per week for at least 12 weeks. The dose or unit dose may be administered once per week for at least 16 weeks. The dose or unit dose may be administered once per week for at least 20 weeks. The dose or unit dose may be administered once per week for at least 24 weeks. The dose or unit dose may be administered once per week for at least 28 weeks. The dose or unit dose may be administered once per week for at least 32 weeks. The dose or unit dose may be administered once per week for about 8 weeks. The dose or unit dose may have a volume permitted it suitable delivery in a single subcutaneous administration step. The dose or unit dose may have a volume of 0.5 to 1 ml. The dose or unit dose may have a volume of less than 1 ml. The dose or unit dose may have a volume of about 0.8 ml.

Administration of the dose or unit dose may provide a plasma concentration of anifrolumab or the functional variant thereof in the patient of ≥10 μg (i.e. 10 μg or more) anifrolumab or the functional variant thereof per ml of plasma (i.e. a plasma concentration of ≥10 μg/ml). Administration of the dose or unit dose may provide a plasma concentration of anifrolumab or the functional variant thereof in the subject of 10-100 μg/ml. Administration of the dose or unit dose may provide a plasma concentration of anifrolumab or the functional variant thereof in the subject of 20-80 μg/ml. Administration of the dose or unit dose may provide a plasma concentration of anifrolumab or the functional variant thereof in the subject of 30-70 μg/ml. Administration of the dose or unit dose may provide a trough concentration of anifrolumab or the functional variant thereof in the subject of ≥20 μg/ml (i.e. 20 μg/ml or more). Administration of the dose or unit dose may provide a trough concentration of anifrolumab or the functional variant thereof in the subject of ≥30 μg/ml (i.e. 30 μg/ml or more). Administration of the dose or unit dose may provide a trough concentration of anifrolumab or the functional variant thereof in the subject of ≥40 μg/ml (i.e. 40 μg/ml or more). Administration of the dose or unit dose may provide a trough concentration of anifrolumab or the functional variant thereof in the subject of 20-100 μg/ml. Administration of the dose or unit dose may provide a trough concentration of anifrolumab or the functional variant thereof in the subject of about 30-80 μg/ml. Administration of the dose or unit dose may provide a trough concentration of anifrolumab or the functional variant thereof in the subject of 40-70 μg/ml.

The dose or unit dose may provide a therapeutic effect in the subject that is at least equivalent to a therapeutic effect provided by administration of an intravenous dose of 300 mg anifrolumab or the functional variant thereof administered once every (Q4W). The dose or unit dose may provide a trough concentration of anifrolumab or the functional variant thereof in the subject that is greater than a trough concentration of anifrolumab or the functional variant thereof provided by administration of an intravenous dose of 300 mg anifrolumab or the functional variant thereof once every 4 weeks (Q4W).

The dose or unit dose may be 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg or 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, or 149 mg.

4.4. The Subject

The subject may be a human subject. The subject may be an adult. The subject may have lupus. The subject may have SLE. The subject may have active SLE. The subject may have moderate to severe SLE. The subject may have lupus nephritis (LN). The subject may have CLE. The subject may have myositis. The subject may have scleroderma. The subject may have Sjogren's syndrome.

The subject may be a patient with an elevated type I IFN gene signature. The subject may be a type I interferon stimulated gene signature (IFNGS)-test high patient pre-administration with the dose or unit dose. The IFNGS may be a 21-gene signature. The IFNGS may be a 4-gene signature. The IFNGS may be a 5-gene signature. The subject may have elevated expression levels of the genes IFI27, IFI44, IFI44L, and RSAD2 in the whole blood. The subject may have elevated expression levels of the genes IFI27, RSAD2, IFI44, IFI44L, IFI6 in the whole blood. The method may comprise identifying the subject as IFNGS-test high patient pre-treatment with the dose or unit dose. The method may comprise measuring the expression of the genes IFI27, IFI44, IFI44L, and RSAD2 in the whole blood of the subject. The method may comprise measuring the expression of the genes IFI27, IFI44, IFI44L, and RSAD2 in the whole blood of the subject. The method may comprise measuring the expression of the genes IFI27, RSAD2, IFI44, IFI44L, IFI6 in the whole blood of the subject by RT-PCR. The gene expression may be measured in an isolated sample from the subject. The measuring may comprise a physical measuring step.

The subject may have a 21-IFNGS score of about 13 at baseline (i.e. pre-treatment with the dose). The subject may have a 21-IFNGS score of about 10, 11, 12, 13, 14, 15 or 16 at baseline (i.e. pre-treatment with the dose). The subject may have a 21-IFNGS score of about 13.1 at baseline (i.e. pre-treatment with the dose).

4.5. Pharmaceutical Composition

In another aspect the invention relates to a pharmaceutical composition for use in a treating SLE in a subject thereof, the method comprising subcutaneously administering the pharmaceutical composition to a subject, wherein the pharmaceutical composition comprises the unit dose of the invention.

In another aspect the invention relates to a pharmaceutical composition for use in a method of treating a type I IFN-mediated disease in a subject, the method comprising subcutaneously administering the pharmaceutical composition to a subject, wherein the pharmaceutical composition comprises the unit dose of the invention.

In another aspect the invention relates to a pharmaceutical composition for use in a method of treating a type I IFN-mediated disease in a subject, the method comprising subcutaneously administering the pharmaceutical composition to a subject, wherein the pharmaceutical composition comprises a dose of anifrolumab or functional variant thereof, wherein the dose is >105 mg and <150 mg. The dose of anifrolumab or the functional variant thereof may be a unit dose (unit dose form, pharmaceutical unit dose form, pharmaceutical unit dose). Functional anifrolumab variants include antigen-binding fragments of anifrolumab and antibody and immunoglobulin derivatives of anifrolumab.

In another aspect the invention relates to a pharmaceutical composition for use in a method of treating a type I IFN-mediated disease in a subject, the method comprising subcutaneously administering the pharmaceutical composition to the subject, wherein the pharmaceutical composition comprises a dose of anifrolumab or functional variant thereof, wherein administering the pharmaceutical composition every week provides a plasma concentration in the subject that is at least equivalent to the plasma concentration provided by intravenous administration of 300 mg of anifrolumab or the functional variant thereof every 4 weeks. Administering the dose every week may provide a plasma concentration in the subject that is about equivalent to the plasma concentration provided by intravenous administration of 400 mg of anifrolumab or the functional variant thereof every 4 weeks. The dose may be <150 mg (i.e. less than 150 mg) anifrolumab or the functional variant thereof. The dose may be >105 mg (i.e. more than 105 mg) anifrolumab or the functional variant thereof. The dose may be ≤135 mg (i.e. 135 mg or less) anifrolumab or the functional variant thereof. The dose may be about 120 mg anifrolumab or the functional variant thereof. The dose may be 120 mg anifrolumab or the functional variant thereof.

Administration of the pharmaceutical composition may provide a plasma concentration of anifrolumab or the functional variant thereof in the patient of ≥10 µg (i.e. 10 µg or more) anifrolumab or the functional variant thereof per ml of plasma (i.e. a plasma concentration of ≥10 µg/ml). Administration of the pharmaceutical composition may provide a plasma concentration of anifrolumab or the functional variant thereof in the subject of 10-100 µg/ml. Administration of the pharmaceutical composition may provide a plasma concentration of anifrolumab or the functional variant thereof in the subject of 20-80 µg/ml. Administration of the pharmaceutical composition may provide a plasma concentration of anifrolumab or the functional variant thereof in the subject of 30-70 µg/ml. Administration of the pharmaceutical composition may provide a trough concentration of anifrolumab or the functional variant thereof in the subject of ≥20 µg/ml (i.e. 20 µg/ml or more). Administration of the pharmaceutical composition may provide a trough concentration of anifrolumab or the functional variant thereof in the subject of ≥30 µg/ml (i.e. 30 µg/ml or more). Administration of the pharmaceutical composition may provide a trough concentration of anifrolumab or the functional variant thereof in the subject of ≥40 µg/ml (i.e. 40 µg/ml or more). Administration of the pharmaceutical composition may provide a trough concentration of anifrolumab or the functional variant thereof in the subject of 20-100 µg/ml. Administration of the pharmaceutical composition may provide a trough concentration of anifrolumab or the functional variant thereof in the subject of 30-80 µg/ml. Administration of the pharmaceutical composition may provide a trough concentration of anifrolumab or the functional variant thereof in the subject of 40-70 µg/ml.

The pharmaceutical composition may provide a therapeutic effect in the subject that is at least equivalent to a therapeutic effect provided by administration of an intravenous dose of 300 mg anifrolumab or the functional variant thereof administered once every (Q4W). The pharmaceutical composition may provide a trough concentration of anifrolumab or the functional variant thereof in the subject that is greater than a trough concentration of anifrolumab or the functional variant thereof provided by administration of an intravenous dose of 300 mg anifrolumab or the functional variant thereof once every 4 weeks (Q4W). The anifrolumab or the functional variant thereof may be comprised within a pharmaceutical composition. The pharmaceutical composition may comprise about 150 to 200 mg/ml anifrolumab or the functional variant thereof, about 25 to 150 mM of a lysine salt and an uncharged excipient. The pharmaceutical composition may comprise 150 mg/mL anifrolumab or the functional variant thereof. The pharmaceutical composition may comprise 50 mM lysine HCl. The pharmaceutical composition may comprise 130 mM trehalose dihydrate. The pharmaceutical composition may comprise 0.05% polysorbate 80. The pharmaceutical composition may comprise 25 mM histidine/histidine HCl. The pharmaceutical composition may comprise 150 mg/mL anifrolumab or the functional variant thereof, 50 mM lysine HCl, 130 mM trehalose dihydrate, 0.05% polysorbate 80 and 25 mM histidine/histidine HCl.

4.6. Formulation

The IFNAR1 inhibitor may be comprised within a pharmaceutical composition. The pharmaceutical composition may comprise about 150 to 200 mg/ml of the IFNAR1 inhibitor, about 25 to 150 mM of a lysine salt and an uncharged excipient. The pharmaceutical composition may comprise 150 mg/mL anifrolumab or the functional variant thereof. The pharmaceutical composition may comprise 50 mM lysine HCl. The pharmaceutical composition may comprise 130 mM trehalose dihydrate. The pharmaceutical composition may comprise 0.05% polysorbate 80. The pharmaceutical composition may comprise 25 mM histidine/histidine HCl. The pharmaceutical composition may comprise 150 mg/ml of the IFNAR1 inhibitor, 50 mM lysine HCl, 130 mM trehalose dihydrate, 0.05% polysorbate 80 and 25 mM histidine/histidine HCl.

The anifrolumab or the functional variant thereof may be comprised within a pharmaceutical composition. The pharmaceutical composition may comprise about 150 to 200 mg/ml anifrolumab or the functional variant thereof, about 25 to 150 mM of a lysine salt and an uncharged excipient. The pharmaceutical composition may comprise 150 mg/mL anifrolumab or the functional variant thereof. The pharmaceutical composition may comprise 50 mM lysine HCl. The pharmaceutical composition may comprise 130 mM trehalose dihydrate. The pharmaceutical composition may comprise 0.05% polysorbate 80. The pharmaceutical composition may comprise 25 mM histidine/histidine HCl. The pharmaceutical composition may comprise 150 mg/mL anifrolumab or the functional variant thereof, 50 mM lysine HCl, 130 mM trehalose dihydrate, 0.05% polysorbate 80 and 25 mM histidine/histidine HCl.

The unit dose may comprise about 150 to 200 mg/ml anifrolumab or the functional variant thereof, about 25 to 150 mM of a lysine salt and an uncharged excipient. The unit dose may comprise 150 mg/ml anifrolumab or the functional variant thereof. The unit dose may comprise 50 mM lysine HCl. The unit dose may comprise 130 mM trehalose dihydrate. The unit dose may comprise about 150 to 200 mg/ml anifrolumab or the functional variant thereof, about 25 to 150 mM of a lysine salt and an uncharged excipient. The unit dose may comprise 150 mg/mL anifrolumab or the functional variant thereof. The unit dose may comprise 50 mM lysine HCl. The unit dose may comprise 130 mM trehalose dihydrate. The unit dose may comprise 0.05% polysorbate 80. The unit dose may comprise 25 mM histidine/histidine HCl. The unit dose may comprise 150 mg/mL anifrolumab or the functional variant thereof, 50 mM lysine HCl, 130 mM trehalose dihydrate, 0.05% polysorbate 80 and 25 mM histidine/histidine HCl.

The pharmaceutical composition may comprise about 150 to 200 mg/ml anifrolumab or the functional variant thereof, about 25 to 150 mM of a lysine salt and an uncharged excipient. The pharmaceutical composition may comprise 150 mg/mL anifrolumab or the functional variant thereof. The pharmaceutical composition may comprise 50 mM lysine HCl. The pharmaceutical composition may comprise 130 mM trehalose dihydrate. The pharmaceutical composition may comprise about 150 to 200 mg/ml anifrolumab or the functional variant thereof, about 25 to 150 mM of a lysine salt and an uncharged excipient. The pharmaceutical composition may comprise 150 mg/mL anifrolumab or the functional variant thereof. The pharmaceutical composition may comprise 50 mM lysine HCl. The pharmaceutical composition may comprise 130 mM trehalose dihydrate. The pharmaceutical composition may comprise 0.05% polysorbate 80. The pharmaceutical composition may comprise 25 mM histidine/histidine HCl. The pharmaceutical composition may comprise 150 mg/mL anifrolumab or the functional variant thereof, 50 mM lysine HCl, 130 mM trehalose dihydrate, 0.05% polysorbate 80 and 25 mM histidine/histidine HCl.

Stable formulations suitable for administration to subjects and comprising anifrolumab are described in detail in U.S. patent Ser. No. 10/125,195 B1, which is incorporated herein in its in entirety.

4.7. Steroids

Many patients with lupus (e.g. SLE) receive corticosteroids (glucocorticoids, oral corticosteroids, OCS). However, corticosteroids are associated with organ damage. Anifrolumab permits tapering of the corticosteroids (glucocorticoids) in lupus (e.g. SLE) patients (steroid sparing). The method of treatment or method may comprise administering a corticosteroid to the subject, optionally wherein the corticosteroid is an oral corticosteroid. The method may comprise tapering dose of corticosteroids administered to the subject (steroid sparing). The method may comprise administering a first dose of the corticosteroid and subsequently administering a second dose of the corticosteroid, wherein the second dose of the corticosteroid is lower than the first dose of the corticosteroid. The second dose of the corticosteroid may be about a 7.5 mg prednisone-equivalent dose or less (see Table 5-4). The second dose of the corticosteroid may be a 5 mg prednisone-equivalent dose or less. The method or method of treatment may comprise administrating the second dose of the corticosteroid once per day. The first dose of the corticosteroid may be about a 10 mg prednisone-equivalent dose. The method may comprise tapering the dose of corticosteroid administered to the patient from 10 mg or more per day to less than 10 mg per day. The method or method of treatment may comprise administering the second dose of the corticosteroid once per day. The method may permit administration of a reduced dose of corticosteroids that is sustained for weeks. The second dose of the corticosteroid may be administered for at least 24 weeks. The second dose of the corticosteroid may be administered for at least 28 weeks.

The method or methods of the invention may comprise administering the standard of care (SOC) to the subject. The method or methods of the invention may comprise administering a steroid to the subject. The method or method of the invention may comprise steroid sparing in the subject, wherein the dose of the steroid administered to the subject is tapered from a pre-sparing dose at baseline to a post-sparing dose.

The method may comprise steroid sparing in the subject, wherein the dose of the steroid administered to the subject is tapered from a pre-sparing dose at baseline to a post-sparing dose. The post-sparing dose may be ≤7.5 mg/day prednisone or prednisone equivalent dose. The pre-sparing dose may be 20 mg/day prednisone or prednisone equivalent dose. The steroid may comprise a glucocorticoid. The steroid may comprise an oral glucocorticoid. The steroid may be selected from the group consisting of hydrocortisone, mometasone, fluticasone, fluocinolone acetonide, fluocinolone, flurandrenolone acetonide, ciclesonide, budesonide, beclomethasone, deflazacort, flunisolide, beclomethasone dipropionate, betamethasone, betamethasone valerate, methylprednisolone, dexamethasone, prednisolone, cortisol, triamcinolone, clobetasol, clobetasol propionate, clobetasol butyrate, cortisone, corticosterone, clocortolone, dihydroxycortisone, alclometasone, amcinonide, diflucortolone valerate, flucortolone, fluprednidene, fluandrenolone, fluorometholone, halcinonide, halobetasol, desonide, diflorasone, flurandrenolide, fluocinonide, prednicarbate, desoximetasone, fluprednisolone, prednisone, azelastine, dexamethasone 21-phosphate, fludrocortisone, flumethasone, fluocinonide, halopredone, hydrocortisone 17-valerate, hydrocortisone 17-butyrate, hydrocortisone 21-acetate, prednisolone, prednisolone 21-phosphate, clobetasol propionate, triamcinolone acetonide, or a mixture thereof. The steroid may be prednisone.

4.8. Device

The also invention relates to an injection device comprising the unit dose of the invention, or the pharmaceutical composition for the use of any of the invention. The pharmaceutical in the injection device may comprise >105 mg (i.e. more than 105 mg) and <150 mg (i.e. less than 150 mg) anifrolumab or a functional variant thereof. The pharmaceutical composition in the injection device may comprise about 120 mg anifrolumab or the functional variant thereof. The pharmaceutical composition in the injection device may comprise 120 mg anifrolumab or the functional variant thereof. The concentration of anifrolumab or the functional variant thereof in the pharmaceutical composition in the injection device may be 150 mg/ml. The volume of the pharmaceutical composition in the injection device may be at least about 0.8 ml. The volume of the pharmaceutical composition may be about 0.8 ml.

The pharmaceutical composition in the injection device may comprise about 150 to 200 mg/ml anifrolumab or the functional variant thereof, about 25 to 150 mM of lysine salt and an uncharged excipient. The pharmaceutical composition in the injection device may comprise 150 mg/mL anifrolumab or the functional variant thereof. The pharmaceutical composition in the injection device may comprise 50 mM lysine HCl. The pharmaceutical composition may comprise 130 mM trehalose dihydrate. The pharmaceutical composition in the injection device may comprise about 150 to 200 mg/ml anifrolumab or the functional variant thereof, about 25 to 150 mM of a lysine salt and an uncharged excipient. The pharmaceutical composition in the injection device may comprise 150 mg/mL anifrolumab or the functional variant thereof. The pharmaceutical composition may comprise 50 mM lysine HCl. The pharmaceutical composition in the injection device may comprise 130 mM trehalose dihydrate. The pharmaceutical composition in the injection device may comprise 0.05% polysorbate 80. The pharmaceutical composition in the injection device may comprise 25 mM histidine/histidine HCl. The pharmaceutical composition in the injection device may comprise 150 mg/mL anifrolumab or the functional variant thereof, 50 mM lysine HCl, 130 mM trehalose dihydrate, 0.05% polysorbate 80 and 25 mM histidine/histidine HCl.

As well as providing for subcutaneous administration of the antibody, the ability to self-administer (e.g. for home use) may further be enhanced by subcutaneous administration via an accessorized pre-filled syringe (APFS), an autoinjector (AI), or a combination thereof. Such devices have been found to be well-tolerated and reliable for administering subcutaneous doses of an antibody and provide further options for optimizing patient care. Indeed, such devices may reduce the burden of frequent clinic visits for patients. An example of a suitable APFS device is described in Ferguson et. al. [6], which is incorporated herein by reference in its entirety.

The dose elucidated by the inventors provides yet advantages in the context of APFS-administration, as an APFS device typically administers a maximal volume of 1 ml. A dose in the range of >105 mg to <155 mg can be readily accommodated by a volume of ~0.8 ml, such that the dose(s) of the present invention are uniquely suited to APFS and AI administration. For comparison, due to viscosity of the anifrolumab, larger doses (particularly doses of >150 mg) would need to be administered within a volume of >1 ml, requiring at least two SC injections, which is inconvenient for the patient, and would require a plurality of pre-filled devices.

The delivery device may be single use, disposable system that is designed to enable manual, SC administration of the dose.

The also invention relates to an injection device comprising a unit dose. The unit dose may comprise >105 mg (i.e. at least 105 mg) and <150 mg (i.e. less than 150 mg) anifrolumab or a functional variant thereof. The unit dose may comprise ≤135 mg (i.e. 135 mg or less) anifrolumab or the functional variant thereof. The unit dose may comprise about 120 mg anifrolumab or the functional variant thereof. The unit dose in the injection device may comprise 120 mg anifrolumab or the functional variant thereof. The unit dose in the injection device may consist essentially of >105 mg and <150 mg anifrolumab or the functional variant thereof. The unit dose in the injection device may consist essentially of ≤135 mg anifrolumab or the functional variant thereof. The unit dose in the injection device may consist essentially of about 120 mg anifrolumab or the or the functional variant thereof. The concentration of anifrolumab or the functional variant thereof in the unit dose in the injection device may be about 150 mg/ml. The volume of the unit dose in the injection device may be less than 1 ml. The unit dose in the injection device may have a volume of 0.5 to 1 ml. The concentration of the unit dose may be about 0.8 ml. The volume of the unit dose may be 0.8 ml. The unit dose in the injection device may comprise a formulation of about 150 to 200 mg/ml anifrolumab or the functional variant thereof, about 25 to 150 mM of a lysine salt and an uncharged excipient. The unit dose in the injection device may comprise a formulation of 150 to 200 mg/ml anifrolumab or the functional variant thereof, 25 to 150 mM of a lysine salt and an uncharged excipient. The unit dose comprises a formulation of 25 mM histidine-HCL, 130 mM trehalose, and 0.05% w/v polysorbate 80. The formulation may have a pH of about 5.9.

The injection device may be a pre-filled syringe (PFS). The injection device may be an accessorized pre-filed syringe (AFPS). The injection device may be an autoinjector (AI).

4.9. Kit

The invention also relates to a kit comprising a unit dose of the invention and instructions for use, wherein the instructions for use comprise instructions for subcutaneous administration of the unit dose to a subject. The invention also relates to a kit comprising the pharmaceutical composition for the use of the invention, wherein the instructions for use comprise instructions for subcutaneous administration of the pharmaceutical composition to a subject.

The invention also relates to a kit comprising the injection device of any of the invention, and instructions for use, wherein the instruction for use comprise instructions for use of the injection device to subcutaneously administer the unit dose or pharmaceutical composition to the subject.

The instructions for use may specify that the injection device, unit dose and/or pharmaceutical composition are for use in the treatment of SLE. The kit of the invention may comprise packaging, wherein the packaging is adapted to hold the injection device and the instructions for use. The instructions for use may be attached to the injection device. The instruction for use may comprise instructions for administration of >105 mg and <150 mg anifrolumab or functional variant thereof. The instruction for use may comprise instructions for administration of ≤135 mg anifrolumab or the functional variant thereof. The instruction for use may comprise instructions for administration of 120 mg anifrolumab or the functional variant thereof. The instruction for use may comprise instructions for administration of 120 mg anifrolumab or the functional variant thereof every 4 weeks. The instructions for use may define the subject as having a type I IFN mediated disease. The instructions may define the subject as having lupus (e.g. SLE). The instructions for use may be written instructions. The instructions for use may specify that the type I IFN inhibitor is for subcutaneous administration.

The instructions for use may specify that the injection device, unit dose and/or pharmaceutical composition are for use in any of the methods of the invention.

The invention also relates to methods of manufacturing the kit of the invention, or the pharmaceutical composition of the invention, or the unit dose of the invention.

4.10. Inhibitor of Type I IFN Mediated Signaling

The inhibitor of type I IFN mediated signaling may be an IFNAR1 inhibitor. The IFNAR1 inhibitor may be a human monoclonal antibody specific for IFNAR1. The IFNAR1 inhibitor may be a modified IgG1 class human monoclonal antibody specific for IFNAR1.

The antibody may comprise a heavy chain variable region complementarity determining region 1 (HCDR1) comprising the amino acid sequence of SEQ ID NO: 3. The antibody may comprise a heavy chain variable region complementarity determining region 2 (HCDR2) comprising the amino acid sequence of SEQ ID NO: 4. The antibody may comprise a heavy chain variable region complementarity determining region 3 (HCDR3) comprising the amino acid sequence of SEQ ID NO: 5. The antibody may comprise a light chain variable region complementarity determining region 1 (LCDR1) comprising the amino acid sequence SEQ ID NO: 6 The antibody may comprise a light chain variable region complementarity determining region 2 (LCDR2) comprising the amino acid sequence SEQ ID NO: 7. The antibody may comprise a light chain variable region complementarity determining region 3 (LCDR3) comprising the amino acid sequence SEQ ID NO: 8.

The antibody may comprise a human heavy chain variable region comprising the amino acid sequence of SEQ ID NO: 1. The antibody may comprise a human light chain variable region comprising the amino acid sequence of SEQ ID NO: 2. The antibody may comprise a human light chain constant region comprising the amino acid sequence of SEQ ID NO: 9. The antibody may comprise a human heavy chain constant region comprising the amino acid sequence of SEQ ID NO: 10. The antibody may comprise in the Fc region an amino acid substitution of L234F, as numbered by the EU index as set forth in Kabat and wherein said antibody exhibits reduced affinity for at least one Fc ligand compared to an unmodified antibody. The antibody may comprise a human heavy chain comprising the amino acid sequence of SEQ ID NO: 11. The antibody may comprise a human light chain comprising the amino acid sequence of SEQ ID NO: 12.

The antibody may comprise: (a) a heavy chain variable region complementarity determining region 1 (HCDR1) comprising the amino acid sequence of SEQ ID NO: 3; (b) a heavy chain variable region complementarity determining region 2 (HCDR2) comprising the amino acid sequence of SEQ ID NO: 4; c) a heavy chain variable region complementarity determining region 3 (HCDR3) comprising the amino acid sequence of SEQ ID NO: 5; (d) a light chain variable region complementarity determining region 1 (LCDR1) comprising the amino acid sequence SEQ ID NO: 6; (b) a light chain variable region complementarity determining region 2 (LCDR2) comprising the amino acid sequence SEQ ID NO: 7; c) a light chain variable region complementarity determining region 3 (LCDR3) comprising the amino acid sequence SEQ ID NO: 8.

The antibody may comprise (a) a human heavy chain comprising the amino acid sequence of SEQ ID NO: 11; and (b) a human light chain comprising the amino acid sequence of SEQ ID NO: 12.

The IFNAR1 inhibitor may be anifrolumab or a functional variant thereof.

The IFNAR1 inhibitor may have an $IC_{80}$ of about 3.88 µg mL$^{-1}$, where the $IC_{80}$ is defined as the approximate concentration required to produce 80% of the maximum inhibition of the 21-IFNGS expression relative to baseline. The IFNAR1 inhibitor may have an $IC_{50}$ of about 6. The IFNAR1 inhibitor may have an $IC_{50}$ of about 6.56 nM.

5. DEFINITIONS

5.1. Inhibitors of Type I IFN Signaling
5.1.1. Anifrolumab

Anifrolumab (MEDI-546, anifro, ANI) is a human immunoglobulin G1 kappa (IgG1$_K$) monoclonal antibody (mAb) directed against subunit 1 of the type I interferon receptor (IFNAR1). Anifrolumab downregulates IFNAR signaling and suppresses expression of IFN-inducible genes. Disclosures related to anifrolumab can be found in U.S. Pat. Nos. 7,662,381 and 9,988,459, which are incorporated herein by reference in their entirety. Sequence information for anifrolumab is provided in Table 5-1: Sequences, FIG. 48 and FIG. 49.

TABLE 5-1

Sequences

| Description | SEQ ID | Sequence |
|---|---|---|
| Anifrolumab VH | 1 | EVQLVQSGAEVKKPGESLKISCKGSGYIFTNYWIAWVRQMPGKGLESMGIIYPGDSDI RYSPSFQGQVTISADKSITTAYLQWSSLKASDTAMYYCARHDIEGFDYWGRGTLVTVS S |
| Anifrolumab VL | 2 | EIVLTQSPGTLSLSPGERATLSCRASQSVSSSFFAWYQQKPGQAPRLLIYGASSRATG IPDRLSGSGSGTDFTLTITRLEPEDFAVYYCQQYDSSAITFGQGTRLEIK |
| HCDR1 | 3 | NYWIA |
| HCDR2 | 4 | IIYPGDSDIRYSPSFQG |

TABLE 5-1-continued

Sequences

| Description | SEQ ID | Sequence |
|---|---|---|
| HCDR3 | 5 | HDIEGFDY |
| LCDR1 | 6 | RASQSVSSSFFA |
| LCDR2 | 7 | GASSRAT |
| LCDR3 | 8 | QQYDSSAIT |
| Light chain constant region | 9 | RTVAAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGEC |
| Heavy chain constant region | 10 | ASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKRVEPKSCDKTHTCPPCPAPE FEGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPASIEKTISKAKGQPREPQVY TLPPSREEMTKNQVSLTCLVKGFYPSDIAVEWESNGQPENNYKTTPPVLDSDGSFFLY SKLTVDKSRWQQGNVFSCSVMHEALHNHYTQKSLSLSPGK |
| Heavy chain | 11 | EVQLVQSGAEVKKPGESLKISCKGSGYIFTNYWIAWVRQMPGKGLESMGIIYPGDSDI RYSPSFQGQVTISADKSITTAYLQWSSLKASD TAMYYCARHD IEGFDYWGRGTLVTVSSASTKGPSVFPLAPSSKSTSGGTAALGCLVKDYFPEPVTVSW NSGALTSGVHTFPAVLQSSGLYSLSSVVTVPS SSLGTQTYIC NVNHKPSNTKVDKRVEPKSCDKTHTCPPCPAPEFEGGPSVFLFPPKPKDTLMISRTPE VTCVVVDVSHEDPEVKFNWYVDGVEVHNAKTK PREEQYNSTYRVVSVLTVLHQDWLNGKEYK CKVSNKALPA SIEKTISKAK GQPREPQVYTLPPSREEMTKNQVSLTCLVKGFYPSDIAVEWESNGQPENNYKTTPPVL DSDGSFFLYSKLTVDKSRWQQGNVFSCSVMHEALHNHYTQKS LSLSPGK |
| Light chain | 12 | EIVLTQSPGTLSLSPGERATLSCRASQSVS SSFFAWYQQK PGQAPRLLIY GASSRATGIPDRLSGSGSGT DFTLTITRLE PEDFAVYYCQ QYDSSAITFG QGTRLEIKRTVAAPSVFIFPPSDEQLKSGT ASVVCLLNNF YPREAKVQWK VDNALQSGNSQESVTEQDSKDSTYSLSSTLTLSKADYEKHKVYACEVTHQGLSSPVTK SFNRGEC |

Anifrolumab is a human immunoglobulin G1 kappa monoclonal antibody that binds to subunit 1 of the type I interferon receptor (IFNAR1) with high specificity and affinity. This binding inhibits type I IFN signaling thereby blocking the biologic activity of type I IFNs. Anifrolumab also induces the internalization of IFNAR1, thereby reducing the levels of cell surface IFNAR1 available for receptor assembly. Blockade of receptor mediated type I IFN signaling inhibits IFN responsive gene expression as well as downstream inflammatory and immunological processes. Inhibition of type I IFN blocks plasma cell differentiation and normalizes peripheral T-cell subsets, restoring the balance between adaptive and innate immunity that is dysregulated in SLE.

In adult patients with SLE, administration of anifrolumab at doses ≥300 mg, via intravenous infusion every 4 weeks, demonstrated consistent neutralization (≥80%) of a 21 gene type I interferon pharmacodynamic (PD) signature in blood. This suppression occurred as early as 4 weeks posttreatment and was either maintained or further suppressed over the 52-week treatment period. Following withdrawal of anifrolumab at the end of the 52-week treatment period in the SLE clinical trials, the type I IFN PD signature in blood samples returned to baseline levels within 8 to 12 weeks. Anifrolumab 150 mg IV showed <20% suppression of the gene signature at early timepoints, that reached a maximum of <60% by the end of the treatment period.

Anifrolumab is an immunoglobulin comprising an HCDR1, HCDR2 and HCDR3 of SEQ ID NO: 3, SEQ ID NO: 4, and SEQ ID NO: 5, respectively (or functional variant thereof); and an LCDR1, LCDR2 and LCDR3 of SEQ ID NO: 6, SEQ ID NO: 7, and SEQ ID NO: 8, respectively (or functional variant thereof). Anifrolumab is an immunoglobulin comprising a VH of SEQ ID NO: 1 and a VL of SEQ ID NO: 2.

The constant region of anifrolumab has been modified such that anifrolumab exhibits reduced affinity for at least one Fc ligand compared to an unmodified antibody. Anifrolumab is a modified IgG class monoclonal antibody specific for IFNAR1 comprising in the Fc region an amino acid substitution of L234F, as numbered by the EU index as set forth in Kabat (1991, NIH Publication 91-3242, National Technical Information Service, Springfield, Va.). Anifrolumab is a modified IgG class monoclonal antibody specific for IFNAR1 comprising in the Fc region an amino acid substitution of L234F, L235E and/or P331S, as numbered by the EU index as set forth in Kabat (1991, NIH Publication 91-3242, National Technical Information Service, Springfield, Va.). Anifrolumab is an antibody comprising a light chain constant region of SEQ ID NO: 9. Anifrolumab is an antibody comprising a heavy chain constant region of SEQ ID NO: 10. Anifrolumab is an antibody comprising a light chain constant region of SEQ ID NO: 9 and a heavy chain constant region of SEQ ID NO: 10. Anifrolumab is an antibody comprising a heavy chain of SEQ ID NO: 11. Anifrolumab is an antibody comprising a light chain of SEQ ID NO: 12. Anifrolumab is an antibody comprising a heavy chain of SEQ ID NO: 11 and a light chain of SEQ ID NO: 12.

Functional variants of anifrolumab are sequence variants that perform the same function as anifrolumab. Functional variants of anifrolumab are variants that bind the same target as anifrolumab and have the same effector function as anifrolumab. Functional anifrolumab variants include antigen-binding fragments of anifrolumab and antibody and immunoglobulin derivatives of anifrolumab. Functional variants include biosimilars and interchangeable products. The terms biosimilar and interchangeable product are defined by the FDA and EMA. The term biosimilar refers to a biological product that is highly similar to an approved (e.g. FDA approved) biological product (reference product, e.g. anifrolumab) in terms of structure and has no clinically meaningful differences in terms of pharmacokinetics, safety and efficacy from the reference product. The presence of clinically meaningful differences of a biosimilar may be assessed in human pharmacokinetic (exposure) and pharmacodynamic (response) studies and an assessment of clinical immunogenicity. An interchangeable product is a biosimilar that is expected to produce the same clinical result as the reference product in any given patient.

For example, a variant of the reference (anifrolumab) antibody may comprise: a heavy chain CDR1 having at most 2 amino acid differences when compared to SEQ ID NO: 3; a heavy chain CDR2 having at most 2 amino acid differences when compared to SEQ ID NO: 4; a heavy chain CDR3 having at most 2 amino acid differences when compared to SEQ ID NO: 5; a light chain CDR1 having at most 2 amino acid differences when compared to SEQ ID NO: 6; a light chain CDR2 having at most 2 amino acid differences when compared to SEQ ID NO: 7; and a light chain CDR3 having at most 2 amino acid differences when compared to SEQ ID NO: 8; wherein the variant antibody binds to the target of anifrolumab (e.g. IFNAR) and preferably with the same affinity.

A variant of the reference (anifrolumab) antibody may comprise: a heavy chain CDR1 having at most 1 amino acid difference when compared to SEQ ID NO: 3; a heavy chain CDR2 having at most 1 amino acid difference when compared to SEQ ID NO: 4; a heavy chain CDR3 having at most 1 amino acid difference when compared to SEQ ID NO: 5; a light chain CDR1 having at most 1 amino acid differences when compared to SEQ ID NO: 6; a light chain CDR2 having at most 1 amino acid difference when compared to SEQ ID NO: 7; and a light chain CDR3 having at most 1 amino acid difference when compared to SEQ ID NO: 8; wherein the variant antibody binds to the target of anifrolumab (e.g. IFNAR) optionally with the same affinity.

A variant antibody may have at most 5, 4 or 3 amino acid differences total in the CDRs thereof when compared to a corresponding reference (anifrolumab) antibody, with the proviso that there is at most 2 (optionally at most 1) amino acid differences per CDR. A variant antibody may have at most 2 (optionally at most 1) amino acid differences total in the CDRs thereof when compared to a corresponding reference (anifrolumab) antibody, with the proviso that there is at most 2 amino acid differences per CDR. A variant antibody may have at most 2 (optionally at most 1) amino acid differences total in the CDRs thereof when compared to a corresponding reference (anifrolumab) antibody, with the proviso that there is at most 1 amino acid difference per CDR.

A variant antibody may have at most 5, 4 or 3 amino acid differences total in the framework regions thereof when compared to a corresponding reference (anifrolumab) antibody, with the proviso that there is at most 2 (optionally at most 1) amino acid differences per framework region. Optionally a variant antibody has at most 2 (optionally at most 1) amino acid differences total in the framework regions thereof when compared to a corresponding reference (anifrolumab) antibody, with the proviso that there is at most 2 amino acid differences per framework region. Optionally a variant antibody has at most 2 (optionally at most 1) amino acid differences total in the framework regions thereof when compared to a corresponding reference (anifrolumab) antibody, with the proviso that there is at most 1 amino acid difference per framework region.

A variant antibody may comprise a variable heavy chain and a variable light chain as described herein, wherein: the heavy chain has at most 14 amino acid differences (at most 2 amino acid differences in each CDR and at most 2 amino acid differences in each framework region) when compared to a heavy chain sequence herein; and the light chain has at most 14 amino acid differences (at most 2 amino acid differences in each CDR and at most 2 amino acid differences in each framework region) when compared to a light chain sequence herein; wherein the variant antibody binds to the same target antigen as the reference (anifrolumab) antibody (e.g. IFNAR) and preferably with the same affinity.

The variant heavy or light chains may be referred to as "functional equivalents" of the reference heavy or light chains. A variant antibody may comprise a variable heavy chain and a variable light chain as described herein, wherein: the heavy chain has at most 7 amino acid differences (at most 1 amino acid difference in each CDR and at most 1 amino acid difference in each framework region) when compared to a heavy chain sequence herein; and the light chain has at most 7 amino acid differences (at most 1 amino acid difference in each CDR and at most 1 amino acid difference in each framework region) when compared to a light chain sequence herein; wherein the variant antibody binds to the same target antigen as the reference (anifrolumab) antibody (e.g. IFNAR) and preferably with the same affinity.

Functional variants of anifrolumab include the antibodies described in WO 2018/023976 A1, incorporated herein by reference (Table 5-2).

TABLE 5-2 anti-IFNAR antibody sequences

| Description | SEQ ID | Sequence |
|---|---|---|
| H15D10 (VH) | 13 | EVQLVQSGAEVKKPGESLRISCKGSGYTFTNYWVA WVRQMPGKGLESMGIIYPGDSDTRYSPSFQGHVTI SADKSISTAY |
| L8C3 (VL) | 14 | DIQMTQSPSSLSASLGDRVTITCRASQNVGNYLNW YQQKPGKAPKLLIYRASNLASGVPSRFSGSGSGTD FTLTISSLQPEDFATYYCQQMEHAPPTFGQGTKVE IKR |
| L16C11 (VL) | 15 | EIVLTQSPGTLSLSPGERATLSCRASQSVIGYYLA WYQQKPGQAPRLLIYSVSTLASGIPDRESGSGSGT DETLTISRLEPEDFAVYYCQQYYRFPITFGQGTKV EIK |
| H19B7 (VH) | 16 | EVQLVQSGAEVKKPGESLRISCKGSGYTFTNYWMA WVRQMPGKGLESMGIIYPSDSDTRYSPSFQGHVTI SADKSISTAYLQWSSLKASDTAMYYCARHDVEGYD YWGQGTLVTVSS |

Functional variants include antibodies comprising the VH amino acid sequence SEQ ID NO: 13. Functional variants include antibodies comprising the VH amino acid sequence SEQ ID NO: 16. Functional variants include antibodies comprising the VL amino acid sequence SEQ ID NO: 14. Functional variants include antibodies comprising the VL amino acid sequence SEQ ID NO: 15. Functional variants include antibodies comprising the VH amino acid sequence SEQ ID NO: 16. Functional variants include antibodies comprising the VH sequence SEQ ID NO: 13 and VL amino acid sequence SEQ ID NO: 16. Functional variants include antibodies comprising the VH sequence SEQ ID NO: 13 and VL amino acid sequence SEQ ID NO: 15. Functional variants include antibodies comprising the VH sequence SEQ ID NO: 16 and VL amino acid sequence SEQ ID NO: 15. Functional variants include antibodies comprising the VH sequence SEQ ID NO: 16 and VL amino acid sequence SEQ ID NO: 14.

IFNAR inhibitors may be a monoclonal antibody comprising the VH amino acid sequence SEQ ID NO: 13. The anti-IFNAR antibodies may comprise the VH amino acid sequence SEQ ID NO: 16. The anti-IFNAR antibodies may comprise the VL amino acid sequence SEQ ID NO: 14. The anti-IFNAR antibodies may comprise the VL amino acid sequence SEQ ID NO: 15. The anti-IFNAR antibodies may comprise the VL amino acid sequence SEQ ID NO: 16. The anti-IFNAR antibodies may comprise the VH sequence SEQ ID NO: 13 and VL amino acid sequence SEQ ID NO: 16. The anti-IFNAR antibodies may comprise the VH sequence SEQ ID NO: 13 and VL amino acid sequence SEQ ID NO: 15. The anti-IFNAR antibodies may comprise the VH sequence SEQ ID NO: 16 and VL amino acid sequence SEQ ID NO: 15. The anti-IFNAR antibodies may comprise the VH sequence SEQ ID NO: 16 and VL amino acid sequence SEQ ID NO: 14.

Functional variants of anifrolumab and anti-IFNAR antibodies include the QX006N antibody described in CN 11327807, incorporated herein by reference.

TABLE 3

QX006N antibody sequences

| Description | SEQ ID NO | Sequence |
|---|---|---|
| QX006N (VH) | 17 | EVQLVESGGGLVQPGGSLRLSCAASGFSLSS YYMTWVRQAPGKGLEWVSVINVYGGTYYASW AKGRFTISRDNSKNTLYLQMNSLRAEDTAVY YCAREDVAVYMAIDLWGQGTLVTVSS |
| QX006N (VL) | 18 | AIQMTQSPSSLSASVGDRVTITCQASQSISN QLSWYQQKPGKAPKLLIYDASSLASGVPSRF SGSRSGTKFTLTISSLQPEDFATYYCLGIYG DGADDGIAFGGGTKVEIK |
| QX006N (HCDR1) | 19 | SYYMT |
| QX006N (HCDR2) | 20 | VINVYGGTYYASWAKG |
| QX006N (HCDR3) | 21 | EDVAVYMAIDL |
| QX006N (LCDR1) | 22 | QASQSISNQLS |
| QX006N (LCDR2) | 23 | DASSLAS |
| QX006N (LCDR3) | 24 | LGIYGDGADDGIA |

IFNAR inhibitors may be a monoclonal antibody comprising the VH amino acid sequence SEQ ID NO: 17. The anti-IFNAR antibodies may comprise the VL amino acid sequence SEQ ID NO: 18.

QX006N is an immunoglobulin comprising an HCDR1, HCDR2 and HCDR3 of SEQ ID NO: 19, SEQ ID NO: 20, and SEQ ID NO: 21, respectively (or functional variant thereof); and an LCDR1, LCDR2 and LCDR3 of SEQ ID NO: 22, SEQ ID NO: 23, and SEQ ID NO: 23, respectively (or functional variant thereof). QX006N is an immunoglobulin comprising a VH amino acid sequence SEQ ID NO: 17 the VL amino acid sequence SEQ ID NO: 18.

5.1.2. Sifalimumab

Sifalimumab (MEDI-545) is a fully human, immunoglobulin G1$_K$ monoclonal antibody that binds to and neutralizes the majority of IFN-α subtypes [7]. Sifalimumab is described U.S. Pat. No. 7,741,449, which is incorporated herein by reference in its entirety. The efficacy and safety of sifalimumab were assessed in a phase IIb, randomised, double-blind, placebo-controlled study (NCT01283139) of adults with moderate to severe active systemic lupus erythematosus (SLE). 431 patients were randomised and received monthly intravenous sifalimumab (200 mg, 600 mg or 1200 mg) or placebo in addition to standard-of-care medications. The primary efficacy end point was the percentage of patients achieving an SLE responder index response at week 52. Compared with placebo, a greater percentage of patients who received sifalimumab (all dosages) met the primary end point (placebo: 45.4%; 200 mg: 58.3%; 600 mg: 56.5%; 1200 mg 59.8%).

5.2. Steroids

Oral corticosteroids (OCS, glucocorticoids) include prednisone, cortisone, hydrocortisone, methylprednisolone, prednisolone and triamcinolone. Examples of equivalent doses of oral prednisone are shown in (Table 5-4).

TABLE 5-4

Examples of equivalent doses of oral prednisone

| Oral Prednisone and Equivalents | Equivalent Dose | | | | |
|---|---|---|---|---|---|
| Oral Prednisone | 7.5 mg | 10 mg | 20 mg | 30 mg | 40 mg |
| Cortisone | 37.5 mg | 50 mg | 100 mg | 150 mg | 200 mg |
| Hydrocortisone | 30 mg | 40 mg | 80 mg | 120 mg | 160 mg |
| Methylprednisolone | 6 mg | 8 mg | 16 mg | 24 mg | 32 mg |
| Prednisolone | 7.5 mg | 10 mg | 20 mg | 30 mg | 40 mg |
| Triamcinolone | 6 mg | 8 mg | 16 mg | 24 mg | 32 mg |

5.3. End Points 5.3.1. SRI (Systemic Lupus Erythematosus Responder Index of ≥4)

A subject achieves SRI(4) if all of the following criteria are met:
Reduction from baseline of >4 points in the SLEDAI-2K;
No new organ system affected as defined by 1 or more BILAG-2004 A or 2 or more
BILAG-2004 B items compared to baseline using BILAG-2004;
No worsening from baseline in the subjects' lupus disease activity defined by an increase ≥0.30 points on a 3-point PGA VAS.

SRI(X) (X=5, 6, 7, or 8) is defined by the proportion of subjects who meet the following criteria:
Reduction from baseline of ≥X points in the SLEDAI-2K;
No new organ systems affected as defined by 1 or more BILAG-2004 A or 2 or
more BILAG-2004 B items compared to baseline using BILAG-2004;
No worsening from baseline in the subjects' lupus disease activity defined by an
increase ≥0.30 points on a 3-point PGA VAS 5.3.2. SLEDAI-2K (Systemic Lupus Erythematosus Disease Activity Index 2000)

The SLEDAI-2K disease activity index consists of a list of organ manifestations, each with a definition. A certified Investigator or designated physician will complete the SLEDAI-2K assessment and decide whether each manifestation is "present" or "absent" in the last 4 weeks. The assessment also includes the collection of blood and urine for assessment of the laboratory categories of the SLEDAI-2K.

The SLEDAI-2K assessment consists of 24 lupus-related items. It is a weighted instrument, in which descriptors are multiplied by a particular organ's "weight". For example, renal descriptors are multiplied by 4 and central nervous descriptors by 8 and these weighted organ manifestations are totaled into the final score. The SLEDAI-2K score range is 0 to 105 points with 0 indicating inactive disease. The SLEDAI-2K scores are valid, reliable, and sensitive clinical assessments of lupus disease activity.

5.3.3. BILAG-2004 (British Isles Lupus Assessment Group-2004)

The BILAG-2004 is a translational index with 9 organ systems (General, Mucocutaneous, Neuropsychiatric, Musculoskeletal, Cardiorespiratory, Gastrointestinal, Ophthalmic, Renal and Haematology) that is able to capture changing severity of clinical manifestations in SLE patients. It has ordinal scales by design and does not have a global score; rather it records disease activity across the different organ systems at a glance by comparing the immediate past 4 weeks to the 4 weeks preceding them. It is based on the principle of physicians' intention to treat and categorizes disease activity into 5 different levels from A to E:

Grade A represents very active disease requiring immunosuppressive drugs and/or a prednisone dose of >20 mg/day or equivalent Grade B represents moderate disease activity requiring a lower dose of corticosteroids, topical steroids, topical immunosuppressives, antimalarials, or NSAIDs Grade C indicates mild stable disease Grade D implies no disease activity but the system has previously been affected Grade E indicates no current or previous disease activity Although the BILAG-2004 was developed based on the principle of intention to treat, the treatment has no bearing on the scoring index. Only the presence of active manifestations influences the scoring.

5.3.4. BICLA (BILAG-Based Composite Lupus Assessment)

BICLA is a composite index that was originally derived by expert consensus of disease activity indices. BICLA response is defined as (1) at least one gradation of improvement in baseline BILAG scores in all body systems with moderate or severe disease activity at entry (e.g., all A (severe disease) scores falling to B (moderate), C (mild), or D (no activity) and all B scores falling to C or D); (2) no new BILAG A or more than one new BILAG B scores; (3) no worsening of total SLEDAI score from baseline; (4) no significant deterioration (≤10%) in physicians global assessment; and (5) no treatment failure (initiation of non-protocol treatment).

Particularly, a subject is a BICLA responder if the following criteria are met:

Reduction of all baseline BILAG-2004 A to B/C/D and baseline BILAG-2004 B to C/D, and no BILAG-2004 worsening in other organ systems, as defined by 1 new BILAG-2004 A or more than 1 new BILAG-2004 B item;

No worsening from baseline in SLEDAI-2K as defined as an increase from baseline of >0 points in SLEDAI-2K;

No worsening from baseline in the subjects' lupus disease activity defined by an increase ≥0.30 points on a 3-point PGA VAS;

BICLA response is a composite endpoint requiring improvement of all baseline BILAG-2004 A and B scores, no worsening as assessed by SLEDAI-2K and PGA, as well as no IP discontinuation and no use of restricted medication beyond protocol-allowed thresholds. The BILAG captures relative improvement in organ system (in contrast to SLEDAI-2K, which is used to show improvement in SRI, and which requires complete resolution in organ system); the BILAG-2004 used to measure improvement in BICLA can detect clinically meaningful relative improvement in an organ system.

5.3.5. CLASI (Cutaneous Lupus Erythematosus Disease Area and Severity Index)

The CLASI is a validated index used for assessing the cutaneous lesions of SLE and consists of 2 separate scores: the first summarizes the inflammatory activity of the disease; the second is a measure of the damage done by the disease. The activity score takes into account erythema, scale/hypertrophy, mucous membrane lesions, recent hair loss, and nonscarring alopecia. The damage score represents dyspigmentation, scarring/atrophy/panniculitis, and scarring of the scalp. Subjects are asked if their dyspigmentation lasted 12 months or longer, in which case the dyspigmentation score is doubled. Each of the above parameters is measured in 13 different anatomical locations, included specifically because they are most often involved in cutaneous lupus erythematosus (CLE). The most severe lesion in each area is measured.

5.3.6. Tender and Swollen Joints

The swollen and tender joint count may be based on left and right shoulder, elbow, wrist, metacarpophalangeal (MCP) 1, MCP2, MCP3, MCP4, MCP5, proximal interphalangeal (PIP) 1, PIP2, PIP3, PIP4, PIP5 joints of the upper extremities and left and right knee of the lower extremities. An active joint for the joint count assessment may be defined as a joint with tenderness and swelling.

5.4. Pharmacokinetics Glossary

Area under the curve (AUC): Area under the plasma drug concentration versus time curve, which serves as a measure of drug exposure.

$C_{ave}$: Steady-state average concentration.

$C_{max}$: The maximum (or peak) concentration of the drug in the plasma.

$C_{min}$: Minimum plasma drug concentration.

$C_{trough}$: the concentration of drug in plasma at steady state immediately prior to the administration of a next dose. Trough plasma concentration (measured concentration at the end of a dosing interval at steady state [taken directly before next administration]).

LLOQ: The lower limit of quantitation, the lowest amount of an analyte in a sample that can be quantitatively determined with suitable precision and accuracy.

Linear pharmacokinetics: When the concentration of the drug in the blood or plasma increases proportionally with the increasing dose, and the rate of elimination is proportional to the concentration, the drug is said to exhibit linear pharmacokinetics. The clearance and volume of distribution of these drugs are dose-independent.

Nonlinear pharmacokinetics: As opposed to linear pharmacokinetics, the concentration of the drug in the blood or plasma does not increase proportionally with the increasing dose. The clearance and volume of distribution of these may vary depending on the administered dose. Nonlinearity may be associated with any component of the absorption, distribution, and/or elimination processes.

5.5. PK/PD

Plasma levels obtainable by SC administration and IV administration may be compared on the basis of a plasma drug concentration-time curve (AUC), which reflects the body exposure to the antibody after administration of a dose of the drug. For example, during a clinical study, the patient's plasma drug concentration-time profile can be plotted by measuring the plasma concentration at several time points. Where an in silico modelling approach is employed, plasma drug concentration-time for any given dose may be predicted. The AUC (area under the curve) can then be calculated by integration of the plasma drug concentration-time curve. Suitable methodology is described in Tummala et. al. [8], which is incorporated herein by reference in its entirety. In the Examples described herein, PK parameters were calculated by non-compartmental analysis with Phoenix™ WinNonlin V/6.2 (Certara, Inc., Princeton, New Jersey, USA) and included the area under the serum concentration-time curve (AUC), clearance (CL, CL/F), maximum serum concentration ($C_{max}$) and time to reach maximum serum concentration ($t_{max}$). All data were analysed with SAS® System V.9.2 (SAS® Institute, Inc., Cary, NC, USA).

Conveniently, a ratio of the AUC obtainable with SC administration to the AUC obtainable by IV administration ($AUC_{SC}/AUC_{IV}$) may be calculated, providing a numerical comparison of bioavailability provided by the dosage routes. Reference to the "AUC Ratio" herein means the $AUC_{SC}/AUC_{IV}$ ratio. To provide statistical robustness, the AUC ratio is preferably a mean, median or mode (for example, a mean) value calculated from a plurality of repeat experiments (or computational simulations). This approach is demonstrated with reference to the Examples. The mean, median or mode (preferably mean) may be derived by pooling data obtained from multiple patients (or multiple computational simulations). Thus, the AUC Ratio may reflect the mean, median or mode (preferably mean) AUC in multiple patients.

Nonlinear PK occurs when clearance is not constant. In other words, nonlinear PK occurs when clearance changes with dose.

5.6. Type I IFN Mediated Disease

Type I IFN mediated disease may be defined as a disease characterized by dysregulation of type I IFN [9]. The type I IFN disease may be a type I IFN-mediated autoimmune disease. The type I IFN disease may be a type I IFN-mediated systemic autoimmune disease. Type I IFN-mediated diseases include lupus (including SLE, LN and CLE). The type I IFN-mediated disease may be lupus nephritis. The type I IFN-mediated diseases include cutaneous lupus erythematosus. Type I IFN-mediated diseases include myositis. Type I IFN-mediated disease include scleroderma. Type I IFN-mediated diseases include Sjogren's syndrome. Type I IFN-mediated diseases include interferonopathies. The Type I IFN-mediated disease may be characterized by association with a high 21-gene IFNGS compared to healthy subjects. The Type I IFN-mediated disease may be characterized by association with a high 4 gene-IFNGS compared to healthy subjects. The Type I IFN-mediated disease may be characterized by association with a high 5 gene-IFNGS compared to healthy subjects.

5.6.1. Myositis

Myositis (also known as idiopathic inflammatory myopathies (IMM)), like SLE, is a connective tissue disease with strong type 1 IFN involvement. Myositis is a rare, progressive and debilitating disease. Myositis is a type I IFN mediated disease. In particularly, type I IFN-inducible genes are overexpressed in whole blood and muscle in patients with myositis [10,11]. Type I IFN gene expression correlates with myositis disease activity [10,11]. Furthermore, type I IFN-secreting plasmacytoid DC (pDC) are present in the target tissues of patients with myositis [12,13]. Additionally, myositis is induced de novo or worsened with IFN treatment [13,14]. Finally, the anti-IFN-α monoclonal antibody, sifalimumab, neutralized IFN gene expression in both DM and PM in muscle, which was associated with improved muscle function (see Examples, Section 11.4). The clinical manifestations of fatigue, rash, photosensitivity and joint pain are common to both lupus and myositis.

5.6.2. Scleroderma

Systemic Sclerosis (Scleroderma, SSc), like SLE, is a connective tissue disease with strong type 1 IFN involvement. Systemic sclerosis is a multi-system autoimmune disease, characterized by functional and structural abnormalities of small blood vessels and fibrosis of skin and internal organs. Type 1 IFN pathway is a pathogenic driver in SSc. Evidence of the central role of Type I IFNs in pathogenesis of SSc (inflammatory and fibrotic processes) includes multiple associated genetic polymorphisms that implicate the type-1 IFN pathway in SSc [15]. Furthermore, SSc auto-antibodies have been found to directly amplify the type-1 IFN response [16], and there is evidence of type-1 IFN contribution to TGF-β dependent and independent fibrosis in lungs and skin of SSc patients [17]. Additionally, digital ulcers due to vascular lesions of small vessels in SSc are associated with high IFN signature [18].

5.7. Type I IFN Gene Signature (IFNGS)

The Interferon Gene Signature (IFNGS) is defined as a set of specific gene transcripts whose expression increases once the IFN receptor (IFNAR1) gets activated by binding of Type I IFN ligands (IFN-α, IFN-β and IFN-ω). Two Interferon Gene Signatures are used as part of the Saphnelo and sifalimumab trials to provide different readouts: The 4-genes Interferon Gene Signature is a peripheral blood signature that was derived from genome-wide gene expression studies and further validated by a quantitative PCT test (developed to specifically measure IFN gene expression based on 4 genes). It is further used at baseline to understand whether a disease or a particular patient's disease is type I IFN driven. The 21 Interferon Gene Signature is a peripheral blood signature that was derived from genome-wide gene expression studies. It is used to study the pharmacodynamic effect of Saphnelo by providing a measure for Type 1 interferon signaling inhibition after treatment.

The IFN 21-gene signature (IFNGS) is a validated pharmacodynamic marker of type I IFN signaling (FIG. 28), that is elevated in patients with type I IFN-mediated disease, including SLE, lupus nephritis, myositis, Sjogren's and scleroderma (FIG. 31A and FIG. 31B).

A 4-gene IFNGS score is calculated by measurement of IFI27, IFI44, IFI44L, and RSAD2 expression. A 5-gene IFNGS score is calculated by measurement of IFI27, RSAD2, IFI44, IFI44L, IFI6 expression. A 21-gene IFNGS score is calculated by measurement of the genes shown in FIG. 28. Gene expression may be measured by detecting mRNA in the whole blood or tissue of the subject. A IFNGS (4-gene, 5-gene or 21-gene) score may be detected in a subject by measuring the IFNGS gene expression (e.g. mRNA) in the blood or tissue of the subject and comparing the gene expression levels to expression of house-keeping or control genes, e.g. ACTB, GAPDH, and 18S rRNA, in the blood or tissue.

6. EXAMPLE 1: ANIFROLUMAB IN THE CLINIC

Anifrolumab safety has been evaluated in 8 blinded or open-label intravenous (IV) and subcutaneous (SC) studies: 6 studies in patients with SLE (Study 05, Study 04, Study 1013, Study 1145, and Study 08), 1 study in patients with systemic sclerosis (SSc) (Study MI-CP180), and 1 study in healthy volunteers (Study 06) (Table 6-1). Of these studies, two (Studies 08 and 06) employed SC anifrolumab administration. Two studies are ongoing: 1 study in patients with SLE (Study 09) and 1 study in patients with lupus nephritis (LN) (Study 07).

evaluate the effect of anifrolumab compared with placebo on overall disease activity. Secondary objectives were chosen to further characterize the efficacy of anifrolumab as compared with placebo, e.g. the ability to reduce glucocorticoid use, the effect on organ-specific endpoints (cutaneous SLE activity and joints), and flare rates.

TABLE 6-1

Clinical studies

| | IFN signaling inhibitor | Name | Subjects | Admin. | Dose | CT.gov |
|---|---|---|---|---|---|---|
| Phase III studies | | | | | | |
| Study 05 | anifrolumab | TULIP II | SLE patients | IV | 300 mg Q4W | NCT02446899 |
| Study 04 | anifrolumab | TULIP I | SLE patients | IV | 300 mg Q4W | NCT02962960 |
| Study 09 | anifrolumab | Long-term extension | SLE patients | IV | 300 mg | |
| Phase II studies | | | | | | |
| Study 1013 | anifrolumab | MUSE | SLE patients | IV | 300 mg or 1000 mg Q4W | NCT01438489 |
| Study 1145 | anifrolumab | MUSE OLE | | IV | 300 mg | NCT01753193 |
| Study 08 | anifrolumab | | SLE patients | SC | | NCT02962960 |
| Study 07 | anifrolumab | | LN patients | | | NCT02547922 |
| | sifalimumab | | SLE patients | IV | 200 mg, 600 mg, or 1200 mg | NCT01283139 |
| Phase I | | | | | | |
| Study MI-CP180 | anifrolumab | | Scleroderma patients | IV | 0.1, 0.3, 1.0, 3.0, 5.0, 10, 20.0 mg/kg | NCT00930683 |
| Study 06 [8] | anifrolumab | | Healthy volunteers | IV and SC | 300 mg, SC, 300 mg IV or 600 mg SC | NCT02601625 |
| Study MI-CP151 | sifalimumab | | Myositis patients | IV | 0.3, 1.0, 3.0 or 10.0 mg/kg | NCT00533091 |

Study MI-CP151 is described in further detail in Higgs et al. 2013 [10]. Study 1013 is described in further detail in Furie et al. 2017 [19], which is incorporated herein by reference in its entirety. Study 04 is described in further detail in Furie et al. 2019 [20], which is incorporated herein by reference in its entirety. The results of Study 05 are presented in Morand et al. 2020 [21], herein incorporated by reference in its entirety. A full summary of the evidence for intravenous anifrolumab clinical efficacy in SLE is provided in Tanaka et al., 2020 [22], which is incorporated herein by reference in its entirety.

7. EXAMPLE 2: SAFETY AND EFFICACY OF INTRAVENOUS ANIFROLUMAB

7.1. Efficacy

The main evaluation of anifrolumab efficacy is based on data from the 3 global, randomized, double-blind, placebo-controlled studies (Phase 3 Studies 04 and 05, and Phase 2 Study 1013). These studies were highly similar in design in that they included a 52-week treatment period and had similar patient characteristics and consistent inclusion/exclusion criteria. The primary objective in all 3 studies was to Across the 3 double-blind, global Phase 2/3 studies (Studies 04, 05, and 1013), the efficacy of anifrolumab 300 mg IV Q4W in patients with moderate-to-severe SLE was observed across a range of clinically important endpoints. Anifrolumab showed an early and sustained effect on overall disease activity, the ability to taper steroid use to a clinically beneficial level ($7.5 mg/day) and maintain this level to Week 52, an early and sustained benefit on cutaneous skin activity, and leads to a clinically meaningful reduction in the rate of flares.

2.1.1: Study 1013 (MUSE, NCT01438489)

Study 1013 (MUSE, NCT01438489) was a phase 2b, multicenter, double-blind, randomized, placebo-controlled, 52-week study of anifrolumab 300 mg and 1000 mg compared with placebo in adult patients with moderately to severely active SLE despite standard of care (SOC) therapy. OCS tapering was encouraged during the trial but was at the discretion of the investigators. The primary efficacy endpoint was evaluated based on reduction in SLE disease activity measured by SRI(4) with sustained reduction in OCS use after 24 weeks of treatment.

The primary endpoint of a composite of SRI(4) response with sustained OCS reduction at Week 24 was met by more patients receiving anifrolumab (34.3% and 28.8% for patients receiving 300 mg [n=99] and 1000 mg [n=104], respectively) than placebo (17.6% [n=102]; p=0.014 and p=0.063 for 300 mg and 1000 mg vs placebo, respectively). A greater effect size was observed in patients with a high IFNGS at baseline, with 36.0% (p=0.004) and 28.2% (p=0.029) of patients treated with anifrolumab 300 mg and 1000 mg, respectively, achieving the primary endpoint vs 13.2% of patients receiving placebo. In patients with a low IFNGS at baseline, the respective response rates for patients achieving the primary endpoint were 29.2%, 30.8%, and 30.8% for anifrolumab 300 mg, anifrolumab 1000 mg and placebo.

Study 1013 is described in further detail in Furie et al. 2017 [19], which is incorporated herein by reference in its entirety.

7.1.1. Studies 04 and 05 (TULIP I and TULIP II)

The pivotal TULIP (Treatment of Uncontrolled Lupus via the IFN Pathway) program comprised two phase 3, multinational, randomized, double-blind, placebo-controlled, parallel-group clinical trials, TULIP-1 (Study 04) and TULIP-2 (Study 05). The design of Study 04 and Study 05 were nearly identical (FIG. 1). Both studies consisted of a 52-week treatment period with anifrolumab or placebo IV Q4W from Week 0 to Week 48 for a total of 13 doses. Primary endpoint was evaluated at Week 52. OCS tapering attempts were mandated in both studies between Weeks 8 and 40 for patients receiving baseline oral prednisone ≥10 mg/day or equivalent, until a dosage ≤7.5 mg/day was achieved, which had to be sustained through to Week 52. Composite endpoints that detected clinically meaningful improvement of SLE disease activity were used in both studies: SRI(4) (primary endpoint in TULIP-1) and BICLA (primary endpoint in TULIP-2).

The selection of the dose of 300 mg anifrolumab every 4 weeks (Q4W) for these studies was based on safety and efficacy results from the interim analysis of the Phase 2b 1013 study where 2 doses of anifrolumab (300 mg and 1000 mg) are evaluated relative to placebo as well as dose-response modelling and simulation (as described in U.S. Pat. No. 9,493,570, corresponding to PCT publication WO2013188494, incorporated herein by reference in its entirety). In the interim analysis of the Phase 2b study, clinically meaningful benefit was observed with the 300 mg dose, with no incremental benefit at 1000 mg. In addition, a higher proportion of subjects reporting herpes zoster reactivations was observed at 1000 mg compared to 300 mg. Given the comparable efficacy between the 300 and 1000 mg anifrolumab doses and the increased frequency of herpes zoster events in the 1000 mg dose group relative to the 300 mg dose group, the benefit:risk profile appeared to favor the 300 mg dose.

In TULIP-1 and TULIP-2, patients with moderate to severe SLE despite standard therapy were randomized to receive anifrolumab 300 mg (TULIP-1 and TULIP-2), anifrolumab 150 mg (TULIP-1 only), or placebo intravenously Q4W for 48 weeks alongside standard therapy. Randomization was stratified depending on Systemic Lupus Erythematosus Disease Activity Index 2000 (SLEDAI-2K) score (<10 vs ≥10) and 4-gene IFNGS status (high versus low) at screening, and oral glucocorticoid dosage (<10 vs ≥10 mg day$^{-1}$ prednisone or equivalent) at baseline. The TULIP-1 and TULIP-2 trials had consistent efficacy variables, safety variables, frequency of assessments, and inclusion/exclusion criteria (FIG. 1).

7.1.2. Study 04 (TULIP I, NCT02446912)

Study 04 compared anifrolumab 150 mg and 300 mg with placebo in adult patients with moderately to severely active SLE despite SOC treatment. Efficacy was evaluated based on reduction in SLE disease activity as measured by SRI(4) response.

In Study 04, the proportion of patients at Week 52 achieving the primary outcome of SRI(4) response was comparable between anifrolumab 300-mg (84/180 [47%]) and placebo groups (79/184 [43%]; difference −3.9; 95% CI −6.3, 14.1; p=0.45) (FIG. 2). Similarly, in the prespecified analysis (unamended restricted medication rules), the proportion of patients at Week 52 with an SRI(4) response was 65 (36%) of 180 treated with anifrolumab 300 mg and 74 (40%) of 184 in the placebo group (difference −4.2; 95% CI −14.2, 5.8; p=0.41).

Study 04 is described in further detail in Furie et al. 2019 [20], which is incorporated herein by reference in its entirety.

7.1.3. Study 05 (TULIP II, NCT02446899)

In Study 05 (TULIP-2), a protocol amendment changed the primary endpoint from SRI(4) to BICLA response before unblinding of trial data and after completion of TULIP-1. This change was informed by MUSE and TULIP-1 analyses.

Study 05 compared anifrolumab 300 mg with placebo in adult patients with moderately to severely active SLE despite SOC treatment. Efficacy in this trial was evaluated based on reduction in SLE disease activity as measured by BILAG-based Composite Lupus Assessment (BICLA) response.

In Study 05, a higher percentage of patients achieved the primary outcome of BICLA response at Week 52 in the anifrolumab group (47.8%) than in the placebo group (31.5%; adjusted difference 16.3%; 95% CI 6.3, 26.3; p=0.001) (FIG. 2, FIG. 3A and FIG. 3B). In the IFNGS test-high subgroup, the percentage of patients with BICLA response at Week 52 was 48.0% (72/150) in the anifrolumab group and 30.7% (46/151) in the placebo group (adjusted difference 17.3%; 95% CI 6.5, 28.2; adjusted p=0.002). The corresponding results in the IFNGS test-low subgroup were 46.7% (14/30) and 35.5% (11/31) of patients in the anifrolumab and placebo groups, respectively (adjusted difference 11.2; 95% CI −13.5, 35.8). There was uniformity of BICLA responses favoring anifrolumab across the other protocol-defined patient subgroups of baseline disease severity, race, ethnicity, age, sex, age at disease onset, and anti-drug antibody status. The HR for time to attainment of sustained BICLA responses up to Week 52 in the overall group favored the anifrolumab 300-mg group over placebo (HR 1.55; 95% CI 1.11, 2.18).

Anifrolumab also showed a significant benefit for sustained OCS reduction and reduction in severity of skin disease (reduction in CLASI score) (FIG. 2). Among patients receiving prednisone ≥10 mg/day or equivalent at baseline, 51.7% (45/87) of anifrolumab-treated patients and 30.1% (25/83) of those receiving placebo achieved a sustained reduction to ≤7.5 mg/day (adjusted difference 21.2%; 95% CI 6.8, 35.7; adjusted p=0.01). Among patients with at least moderately active skin disease (CLASI score ≥10) at baseline, 49.0% (24/49) of those receiving anifrolumab and 25.0% (10/40) of those receiving placebo experienced CLASI score reductions ≥50% at Week 12 (adjusted difference 24.0%; 95% CI 4.3, 43.6; adjusted p=0.04). Although treatment response in organs other than skin and joints was not part of the prespecified analyses, the BICLA response definition requires improvement in all organ systems affected at baseline (reduction of all baseline BILAG-2004 A and B domain scores to B/C/D and C/D, respectively) and no new flares in the remaining BILAG-2004 organ systems. At baseline, the most affected organ domains for enrolled patients were mucocutaneous and musculoskeletal (>80% with BILAG-2004 A or B involvement). Baseline BILAG-2004 A or B scores occurred less frequently in the cardiorespiratory, constitutional, renal, neuropsychiatric, gastrointestinal, hematologic, and ophthalmic domains. Therefore, by definition, response occurred across all these affected BILAG-2004 organ systems in patients who achieved BICLA response. The BILAG-2004-based annualized flare rate was 0.43 in the anifrolumab group and 0.64 in the placebo group (adjusted rate ratio 0.67; 95% CI 0.48, 0.94; adjusted p=0.08) [37]. Among patients with ≥6 swollen and ≥6 tender joints at baseline, 42.2% (30/71) in the anifrolumab group and 37.5% (34/90) in the placebo group (adjusted difference 4.7%; 95% CI −10.6, 20.0; adjusted p=0.55) had a ≥50% reduction in both swollen and tender joint counts at Week 52.

The results of Study 05 are presented in Morand et al. 2020 [21], herein incorporated by reference in its entirety.

7.1.4. Efficacy Conclusion

Study 05 provided strong evidence for anifrolumab efficacy for the treatment of patients with moderately to severely active SLE despite SOC treatment based on the prespecified BICLA primary endpoint. The combined data from all three clinical trials further support the efficacy of anifrolumab 300 mg in these patients across a range of clinically significant endpoints. Importantly, there was a consistent benefit of anifrolumab 300 mg in all studies for BICLA response rate at Week 52; treatment differences >16% compared with placebo were observed in BICLA response rates in all three studies. In addition, in both TULIP-2 and MUSE, anifrolumab suggested treatment benefit for SRI(4) response. The consistent, supporting efficacy evidence for anifrolumab 300 mg across the many key secondary endpoints (e.g. OCS reduction, improvement in CLASI score, flare reduction) is relevant to characterize the full extent of anifrolumab's treatment effect, particularly given the heterogeneity of SLE manifestations.

Anifrolumab shows efficacy for the reduction of flares, and the onset of treatment effect for reducing disease activity occurs as early as 8-12 weeks after treatment initiation, when numerical separation of BICLA response rates by >10% were observed in favor of anifrolumab 300 mg and remained throughout 52 weeks of treatment. In addition, the steroid-sparing effect of anifrolumab potentially reduces the cumulative risk of long-term organ damage associated with SLE. The improvements seen with anifrolumab treatment in skin manifestations (CLASI activity score) are also particularly important as they are common, and the face, head, and neck are frequently involved with lesions that are visible.

A full summary of the evidence for intravenous anifrolumab clinical efficacy in SLE is provided in Tanaka et al., 2020 [22], which is incorporated herein by reference in its entirety.

7.2. Safety

Safety and tolerability of anifrolumab were consistent and generally similar across all three efficacy studies. The percentage of patients with any adverse event (AE) ranged from 85% to 89% across the studies among those treated with anifrolumab, and from 77% to 84% in placebo groups. The most common AEs included upper respiratory tract infections, nasopharyngitis, and infusion-related reactions. Anifrolumab infusions were generally well tolerated, and there was one report of anaphylaxis that occurred in a patient receiving anifrolumab 150 mg in TULIP-1. Few patients had hypersensitivity, and most infusion-related AEs were not serious and were mild or moderate in intensity. Serious AEs (SAEs) occurred in 8-16% of anifrolumab-treated patients and in 16-19% of patients receiving placebo. There was one death each in the treatment period of TULIP-1 and TULIP-2, both of which occurred in the anifrolumab treatment arm and were due to pneumonia. There was also one death in MUSE of a patient who received 1 dose of anifrolumab 1000 mg and had acute colitis. The percentage of patients with AEs leading to discontinuation was smaller among those receiving anifrolumab vs placebo in TULIP-2 and MUSE but larger among anifrolumab-treated patients in TULIP-1 (6% vs 3% with placebo).

There was an increased incidence of herpes zoster in the anifrolumab treatment groups (5-7%) compared with placebo groups (1-2%); most occurrences were cutaneous, not serious, and did not lead to discontinuation. All responded to SOC treatment and generally resolved without sequelae. For other AEs of special interest, the incidence was low and similar across treatment groups.

A full summary of the evidence for anifrolumab safety and tolerability is provided in Tanaka et al., 2020 [22], which is incorporated herein by reference in its entirety.

7.3. Conclusion

Anifrolumab demonstrated a clinically relevant benefit in subjects with moderate to severe SLE treated with SOC. The efficacy was supported by a broad range of clinical measures of global (various levels of SRI responses, BICLA) and organ specific disease activity (CLASI, joint count). A clinically relevant increase in the proportion of subjects achieving prespecified corticosteroid reduction in the 300 mg group was also observed compared with placebo, while no apparent difference was observed comparing the 1000 mg group and placebo.

Anifrolumab was generally well tolerated. A dose-related increase in the number of subjects with uncomplicated herpes zoster infections was observed in subjects receiving anifrolumab compared with placebo.

BICLA response was consistently achieved by a greater number of patients receiving anifrolumab compared with placebo across all three studies, as were sustained OCS reduction and improvement in CLASI. In both MUSE and TULIP-2, a greater percentage of patients also achieved an SRI(4) response with anifrolumab vs placebo. The safety profile of anifrolumab was generally similar across the efficacy studies, with SAEs occurring in 8-16% of anifrolumab-treated patients and 16-19% of patients receiving placebo. There was an increased incidence of herpes zoster in the anifrolumab treatment groups compared with placebo groups in all three studies, but most occurrences were cutaneous in presentation and responded to SOC treatment. Evidence from the clinical trials discussed suggests that in patients with active SLE, anifrolumab 300 mg administered IV Q4W is superior to placebo in achieving composite endpoints of disease activity response, as well as reducing OCS dosage, severity of skin disease, and flare rate. Thus, it was concluded from the clinical studies of IV anifrolumab administration that 300 mg IV Q4W was the optimal dose when compared to 150 mg Q4W. Increasing the dose to 1000 mg Q4W was found to provide only incremental benefit and dose-related increase in herpes zoster infection was observed (FIG. 4).

8. EXAMPLE 3: SUBCUTANEOUS ADMINISTRATION OF ANIFROLUMAB

8.1. Phase I Study MI-CP180 of IV Anifrolumab in Patients with SSc

Mean anifrolumab serum concentrations after a single-dose administration based on body weight are presented in FIG. 5A. After a single-dose administration, anifrolumab exhibited nonlinear-linear PK at lower dose levels (<10.0 mg/kg) in both IFNGS high and IFNGS low patients. A dose-proportional increase in $C_{max}$ was observed, but an increase in AUC was more than dose proportional between 0.1 and 10.0 mg/kg. Anifrolumab t1/2 was more prolonged in higher dose cohorts. At the highest dose level investigated (20.0 mg/kg), the terminal t1/2 was approximately 12 days.

8.2. Phase I of IV and SC Anifrolumab in Healthy Volunteers (Study 06)

In this Phase I randomized, placebo-controlled study, 30 healthy adults were assigned to three treatment cohorts (anifrolumab 300 mg SC (n=6), anifrolumab 300 mg intravenous (n=6), anifrolumab 600 mg SC (n=6)) and placebo (n=4/cohort). After SC administration, exposure to anifrolumab increased dose proportionally from 300 mg to 600 mg based on area under the serum concentration-time curve. Arithmetic mean serum anifrolumab concentration-time profiles following single IV and SC administration are shown in FIG. 5B. As reported in Tummala et al. 2018 [8], which is incorporated herein by reference in its entirety, this study estimated the bioavailability to anifrolumab in healthy volunteers to be 87% of the intravenous exposure.

8.3. Phase II of SC Anifrolumab in SLE Patients (Study 08)

This study was designed to characterize the pharmacokinetics and pharmacodynamics of subcutaneously administered anifrolumab (FIG. 6A).

The study explored the clinical pharmacology, safety, and exploratory efficacy of subcutaneous anifrolumab. Pharmacokinetics in Study 08 were consistent with the high bioavailability in Study 06 (healthy volunteers) and high CL in IFNGS high patients with SLE. Anifrolumab, administered subcutaneously every 2 weeks to patients with SLE and moderate-to-severe skin manifestations had non-linear pharmacokinetics that were more than dose proportional, and neutralized the type I interferon gene signature in a dose-dependent manner (FIG. 6B and FIG. 6C). In particular, 150 mg or 300 mg of subcutaneous anifrolumab administered every 2 weeks for 50 weeks had non-linear pharmacokinetics, whereby $C_{trough}$ concentrations were more than dose proportional. The number of adverse events with subcutaneous anifrolumab was similar to the numbers observed following intravenous administration in larger studies of patients with SLE.

The results of Study 08 are fully described in Bruce et al. [23], which is incorporated herein by reference in its entirety.

Study 08 was limited by small samples sizes, and no conclusions could be drawn about the biological effects of the study drug (e.g., on complement C3 or C4 concentrations) or its clinical efficacy. The inclusion of only patients with high type I interferon gene signatures and active skin disease also limited the generalizability of the study to patients with similar disease characteristics. The study was further limited by the increasing frequency of missing values with time.

8.4. Conclusion

The PK of anifrolumab consistently exhibited target mediated drug disposition where the concentrations or exposures decreased more than dose-proportional at lower dose levels. High bioavailability of anifrolumab administered via SC injection was observed in Study 06 (healthy volunteers); the ratio of the AUC of anifrolumab SC to anifrolumab IV under 300 mg was approximately 87%.

9. EXAMPLE 4: DETERMINATION OF THE OPTIMAL SUBCUTANEOUS UNIT DOSE 9.1. Aim

In order to detect an optimal dosage regimen for subcutaneous administration of anifrolumab, the inventors developed a population PK and a PK/PD model, designed to utilize existing human clinical trial. The PK data from phase III Studies 04 and 05 and phase II Study 1013 were used to assist the development of the population PK model.

An initial goal of the inventors was to detect a subcutaneous dose providing an equivalent exposure as a standard 300 mg IV (Q4W) dose, while concomitantly allowing more regular dosing that could be provided in a lower volume. This was based on the understanding that 300 mg IV Q4W provides optimal clinical PK profiles and clinical efficacy (e.g. in terms of achieving BICLA response) as reported e.g. in Furie et. al. 2017 which is incorporated herein by reference in its entirety.

9.2. Results 9.2.1. Initial Selection of the Subcutaneous Dose for Anifrolumab

In an initial analysis, the inventors determined specific dosage regimens predicted to provide equivalent exposure to that achievable with 300 mg Q4W IV. A dosage regimen of 105 mg subcutaneous weekly (QW) was initially found to provide an AUC ratio close to (or slightly greater than) 1 (FIG. 7A), even where projected bioavailability was reduced by ~7% relative to that reported in Tummal et. al. 2018 [8] (incorporated herein by reference in its entirety) to account for inter-individual variance in bioavailability (FIG. 7B). 105 mg subcutaneous QW appeared to provide comparable or improved median trough concentrations and IFNGS suppression as the comparative 300 Q4W mg IV dose (FIG. 8A and FIG. 8B). From these initial analyses it appeared that SC 105 mg QW dose of anifrolumab should be selected as equivalent to a 300 mg Q4W and thus as having the optimal efficacy/risk profile for the treatment of SLE patients. Importantly these analyses assumed that the 300 mg IV dose was on or close to the plateau of the dose response curve for anifrolumab, i.e. that increasing the dose beyond 300 mg IV Q4W would provide not provide any meaningful benefit to patients, particularly when taking into account the increased risk of herpes zoster infection for higher doses.

9.2.2. Amended Selection of the Subcutaneous Dose for Anifrolumab

The inventors therefore first considered 105 mg QW to be the optimal SC dose of anifrolumab for the treatment of type I IFN mediated disease based on the data available from the MUSE study, Study 06 and Study 08. However, to confirm the selection of the 105 mg SC dose, the inventors conducted further analysis of the data from the TULIP I (Study 04) and TULIP II (Study 05) clinical trials.

Using the additional data, a positive-exposure-BICLA relationship in IFNGS high patients was demonstrated. Surprisingly, this relationship was observed even within the 300 mg IV Q4W group (FIG. 9A and FIG. 9B). BICLA response within the 300 mg IV Q4W patient group was therefore variable. Logistic regression of the week 52 BILCA response in patients confirmed that PK exposure was a significant covariate in both TULIP I and TULIP II. $C_{ave}$ was found to be statistically significant in both the analysis of all-comers and IFNGS high completed the treatments in both TULIP I and TULIP II independently and pooled TULIP I and TULIP II analysis. Exposure-response demonstrating higher $C_{ave}$ were correlated with higher BICLA and SRI(4) in pooled data from the TULIP I and TULIP II studies. In other words, there was exposure-dependent variability in response to anifrolumab within lupus patients administered 300 mg Q4W IV (FIG. 9A and FIG. 9B).

Surprisingly, the 300 mg IV Q4W dose was thus found to reside on the onset of the plateau of exposure response, whilst the suboptimal 150 mg IV dose resided in the step region of the exposure-response curve (FIG. 10A). As a consequence of these analyses, the inventors determined that a 105 mg QW subcutaneous dose (previously considered equivalent to a 300 mg IV Q4W dose) would not provide the optimal balance of efficacy and safety in lupus patients. The inventors thus determined to select another dose for SC administration that would mitigate the impact of variability in response a population of lupus patients.

In summary, from initial analysis, it appeared that administration of a subcutaneous dose of 105 mg QW anifrolumab would achieve at least a similar efficacy as 300 mg IV Q4W. However, surprisingly, following further analysis by the inventors of newly available data from further studies, it was found that the concentration of this weekly (QW) dose could be increased without reaching a maximum threshold in terms of bioavailability and efficacy. In other words, the QW dose could be increased beyond 105 mg to provide even greater blood plasma concentrations and IFNGS suppression, and to mitigate the observed variability in response in SLE patients. A dose of 105 mg would therefore be suboptimal.

The surprising additional dose-response curve data were further validated by demonstrating that the probability of meeting a relevant BICLA response (in IFNGS high patients) was increased for weekly subcutaneous administration with concentrations higher than the 105 mg dose (Table 9-1). These data demonstrate the unexpected position of the dose-response plateau (e.g. under subcutaneous administration), which shifts to the right for doses increasing above 105 mg (FIG. 10B), showing the maximal BICLA response is in fact achievable with a dose of greater than 105 mg and that a higher dose would be preferable (Table 9-1).

TABLE 9-1

SC Efficacy Projection assuming no dose delays/interruptions.

| | 90 mg SC QW | 105 mg SC QW | 120 mg SC QW | 135 mg SC QW | 150 mg SC QW |
|---|---|---|---|---|---|
| | Equivalent IV dose | | | | |
| | ~300 mg IV Q4W | ~< 400 mg IV Q4W | ~< 450 mg IV Q4W | <500 mg IV Q4W ~300 mg SC Q2W | |
| Median Cave ratio to 300 mg IV | 0.92 | 1.14 | 1.36 | 1.59 | 1.81 |
| % exceeded 95$^{th}$ percentile of 300 mg IV | 3.3% | 9.4% | 20.1% | 33.5% | 48.9% |
| % overlapped with ≥5$^{th}$ percentile of 1000 mg IV | 0.3% | 1.8% | 5% | 11% | 21% |
| % IFNGS high pts with 55% chance of BICLA response | ~86% | ~94% | ~98% | ~99% | ~100% |
| % IFNGS high pts with 60% chance of BICLA response | ~10% | ~23% | ~38% | ~55% | ~68% |

9.2.3. The Bioavailability of Anifrolumab is Highly Variable

Upon further investigation as to the bioavailability of anifrolumab, the inventors elucidated that a surprisingly high level of variability in anifrolumab bioavailability subsequent to subcutaneous administration may exist amongst different patients. The high level of variability in anifrolumab bioavailability was not appreciated in previous studies reporting >80% bioavailability for subcutaneous administration (see Example 3) [8]. The bioavailability (F1) of anifrolumab in Study 08 (SLE patients, SC) was found to be 81% in healthy volunteers using the population PK model (Table 9-2).

TABLE 9-2

Anifrolumab bioavailability based on healthy volunteers

| Parameters ± SE | Final IV SLE model (including 6 subjects from 06 IV arm) | Study 06 HVs (300 mg IV: 6, 300 mg SC: 6, 600 mg SC: 6) |
|---|---|---|
| CL (IFNGS high) | 0.193 L/day | — |
| CL (IFNGS low/HVs) | 0.153 L/day | 0.146 ± 0.036 L/day |
| IIV: CL | 0.109 (CV: 33.1%) | 0.0431 (CV: 20.8%) |
| F1 | — | 0.812 ± 0.12 |
| Ka | — | 0.274 ± 0.124 /day |
| IIV: Ka | — | 0.221 (CV: 47%) |

The inventors conducted external validation of Study 08, Ph2 SC in SLE, using a PPK model developed with healthy volunteers and SLE patients from IV studies to determine the bioavailability in lupus population.

In-depth analysis of the data from Study 08 revealed that bioavailability was affected by SC administration site. In particular, when the bioavailability of 300 mg at the abdomen was estimated versus IV, the bioavailability (F1) was estimated to be 85.4% compared to 81% when the sites of injection was not taken into consideration. As such, $C_{troughs}$ following injection at thigh trended downward compared to injection at abdomen (FIG. 11A and FIG. 11B). As such, it was surprisingly concluded that bioavailability may, in fact, be as low as 70%, taking into account variability due to injection site and the higher variability in bioavailability for lupus (SLE) patients compared to healthy volunteers. Importantly, if a bioavailability (F1) of 81-87% was assumed, 105 mg was initially projected to provide a comparable $C_{ave}$ to that of 300 mg IV (FIG. 12). By contrast, when the estimated bioavailability was reduced to ~70% or less, the median $C_{ave}$ of the 105 mg QW subcutaneous dose fell to below 1 (FIG. 13A, FIG. 13B and Table 9-3).

TABLE 9-3

Anifrolumab bioavailability

| Bioavailability | 90 mg SC QW | 105 mg SC QW | 120 mg SC QW | 135 mg SC QW | 150 mg SC QW |
|---|---|---|---|---|---|
| 82% | 0.92 | 1.14 | 1.36 | 1.59 | 1.81 |
| ~70% | 0.73 | 0.92 | 1.11 | 1.31 | 1.49 |
| ~60% | 0.57 | 0.73 | 0.89 | 1.06 | 1.22 |

Values = median $C_{ave}$ to 300 mg IV; SC = subcutaneous

Furthermore, there was an undesirable 30% overlap in $C_{ave}$ between 105 mg SC QW and the suboptimal IV dose, 150 mg Q4W versus the only 16% overlap observed when the bioavailability was assumed to be 81% (FIG. 13A). However, when a SC 120 mg dose was used, the $C_{ave}$ overlap with the 150 mg IV dose was less than the overlap with the optimal IV dose of 300 mg IV, even when a low bioavailability of 70% was assumed (FIG. 13B). Furthermore, the 120 mg SC QW dose had minimal overlap with the undesirable 1000 mg IV dose (FIG. 13C), at which the risk of herpes zoster infection is increased (FIG. 15). A 150 mg SC QW dose had an undesirable overlap with the 1000 mg IV Q4W dose. Even more surprisingly, a SC dose of 120 mg or more was projected to have better PD suppression (Table 9-4) than the assumed optimal 300 mg IV dose (Table 9-5).

Selection of a dose higher than 105 mg, preferably 120 mg or higher, therefore optimizes the exposure-response by minimizing the impact of the variability of the onset of response and bioavailability in patients with lupus (e.g. SLE) (Table 9-4, FIG. 14A, FIG. 14B). A SC dose of below 150 mg QW is also desirable to reduce the risk of herpes zoster infection (FIG. 15).

TABLE 9-4

Calculated % PD suppression at week 24, SC dose

| SC Dose (mg) | WK24 Suppression (%) | | |
|---|---|---|---|
| | 75% | 80% | 90% |
| 90 | 89.0 | 84.6 | 63.8 |
| 105 | 92.9 | 89.8 | 69.2 |
| 120 | 94.8 | 91.9 | 74.2 |
| 135 | 96.0 | 93.9 | 75.8 |
| 150 | 96.5 | 94.6 | 80.2 |

TABLE 9-5

Calculated % PD suppression at week 24, IV dose

| IV Dose (mg) | WK24 Suppression (%) | | |
|---|---|---|---|
| | 75% | 80% | 90% |
| 300 | 74.2 | 68.3 | 42.5 |
| 400 | 82.9 | 77.9 | 54.7 |
| 450 | 85.9 | 80.8 | 56.4 |
| 500 | 88.7 | 84.8 | 62.5 |
| 600 | 92.7 | 88.8 | 68.9 |
| 1000 | 96.9 | 94.5 | 80.2 |

Doses of 120 mg and 135 mg QW particularly provide reasonable benefit-risk profiles. At doses at 150 mg QW or above, there is an increase in safety risk e.g. an increase in the risk of herpes zoster in patients, given that a SC dose of 150 mg QW is equivalent to a 1000 mg IV Q4W (FIG. 13C, FIG. 15A). A subcutaneous dose of less than 150 mg QW and more than 105 mg QW was therefore determined as the preferred dose. A subcutaneous dose of less than 150 mg QW and less or equal to 135 mg was determined as the more preferred dose. A subcutaneous dose of 120 mg was determined as optimal dose.

To summarize, the inventors found that the optimal subcutaneous dose of anifrolumab may first appear to be 105 mg QW given the preliminary data that was previously available (FIG. 15). However, further data and analyses surprisingly revealed that a dose of 105 mg QW or lower would under-dose a significant proportion of patients (FIG. 10B, Table 9-3). Thus, a particularly advantageous dosing regimen demonstrated by the inventors was doses higher than 105 mg QW. A particularly optimal dose was determined to be 120 mg subcutaneous QW, which is equivalent to approximately 400 mg IV Q4W, depending on estimated bioavailability. The optimal SC dose is therefore surprisingly >30% higher than what would be considered optimal based solely on a comparison with 300 mg IV Q4W and the previously understood bioavailability of anifrolumab. In other words, the data from Study 06 (300 mg IV versus 300 mg and 600 mg SC (Abdomen), suggested a bioavailability of anifrolumab of about 86% (comparing 300 mg SC to 300 mg IV). However, surprisingly, further analysis of Study 08 (150 mg and 300 mg SC, Q2W) found that $C_{troughs}$ following injection at the thigh trended downward compared to injection at the abdomen. Bioavailability was therefore estimated to be about 81% when the sites of injection was not taken into consideration based on modeling and simulation, but could be as low as 70%, justifying a SC dose selection of higher than 105 mg QW (FIG. 14).

The inventors have thus surprisingly demonstrated that a dose of greater than 105 mg SC QW and less than 150 mg SC QW, and in particular a dose of 120 mg QW (a) maximizes efficacy whilst maintaining an acceptable safety profile, (b) mitigates the impact of variability in bioavailability and (c) mitigates the impact of variability in the onset of response. Thus, dosing at greater than 105 mg QW advantageously accounts for the variance in bioavailability, leading to improved therapeutic outcome. A dose of less than 150 mg QW mitigates the risk of herpes zoster infection.

Pharmacokinetic data in healthy volunteers (study 06 [IV arm only]) and in patients with SLE (Studies 1013, 02, 04, and 05) were also pooled to evaluate the impacts of covariates, such as demographics and renal/liver function tests, on PK exposure. Higher body weight and type I IFN test high patients were found to have significantly higher clearance (CL) and lower concentrations. However, surprisingly there was no clinically relevant impact of these covariates on efficacy and safety. Surprisingly, other covariates pertaining to specific populations evaluated in population PK modeling were not found to be significant including race/ethnicity/region, age, gender, renal/hepatic function tests, standard of care therapy (e.g., OCS, anti-malarial, azathioprine, methotrexate, mycophenolate mofetil, mycophenolic acid, mizoribine, and NSAIDs), and commonly used medications in SLE patients (ACE inhibitors and HMG-COA reductase inhibitors).

9.3. Conclusion

The present inventors have demonstrated that an anifrolumab dose of <150 mg Q and >105 mg QW will provide at least similar or even a higher $C_{ave}$ over 52 weeks to that of 300 mg IV Q4W. A 120 mg SC QW dose will particularly provide an efficacy at least equivalent to that demonstrated for a 300 mg IV Q4W dose in lupus patients. It is further plausibly demonstrated that a 120 mg SC QW dose will provide an efficacy greater than that demonstrated for a 300 mg IV Q4W dose.

On the basis of the data demonstrated herein a subcutaneous dose of anifrolumab for has been selected for a multi-center, randomized, double-blind, placebo-controlled, phase 3 study evaluating the efficacy and safety of subcutaneous anifrolumab in adult patients with SLE. In summary, two doses of SC anifrolumab (150 mg and 300 mg every 2 weeks [Q2W]) were evaluated in the completed Phase 2 SC study in SLE patients with Type I IFN test high results and active skin disease (Study 06). The primary pharmacokinetic (PK)/pharmacodynamic (PD) endpoints of the Phase 2 SC study were analyzed at Week 12 and safety, and tolerability of SC administration of anifrolumab was assessed through Week 52. Based on PK/PD data from the Phase 2 SC study as well as data from anifrolumab IV studies, a dose of 120 mg QW was selected for this current Phase 3 SC study to provide comparable and noninferior average concentration ($C_{ave}$) to 300 mg IV in a single injection and hence 120 mg SC QW is expected to provide at least similar efficacy to 300 mg IV Q4W.

Given the change of dosing interval from Q4W to QW and by providing at least similar $C_{ave}$, the troughs concentrations of 120 mg SC QW are projected to be higher than those of 300 mg IV Q4W, and hence it is expected to provide noninferior PD suppression to that of 300 mg IV. In addition, the $C_{ave}$ of 120 mg SC QW over 52 weeks has minimal overlap with that of 1000 mg IV (evaluated in the Phase 2b Study 1013) which was shown to be safe and tolerable, and thus, any dose equivalent to below 1000 mg IV Q4W is considered to be safe.

Development of a SC route of administration using APFS of AI for anifrolumab is expected to provide increased convenience and dosing flexibility and reduced exposure to infection risk related to clinic visits for dosing (including but not limited to influenza or COVID-19) for patients and/or caregivers and to improve treatment accessibility and compliance.

10. EXAMPLE 5: THE RELATIONSHIP BETWEEN ANIFROLUMAB PHARMACOKINETICS, PHARMACODYNAMICS, AND EFFICACY IN PATIENTS WITH MODERATE TO SEVERE SYSTEMIC LUPUS ERYTHEMATOSUS 10.1. Abstract This study aimed to elucidate the pharmacokinetic/pharmacodynamic and pharmacodynamic/efficacy relationships of anifrolumab, a type I interferon receptor antibody, in patients with moderate to severe systemic lupus erythematosus (SLE). Data were pooled from the randomized, 52-week, placebo-controlled TULIP-1 and TULIP-2 trials of intravenous anifrolumab (150 mg/300 mg, every 4 weeks [Q4W] for 48 weeks). Pharmacodynamic neutralization was measured with a 21-gene type I interferon gene signature (21-IFNGS) in IFNGS-high patients. The pharmacokinetic/pharmacodynamic relationship was analyzed graphically and modeled with a nonlinear mixed-effects model. British Isles Lupus Assessment Group-based Composite Lupus Assessment (BICLA) response rates were compared across 21-IFNGS neutralization quartiles. Overall, 819 patients received ≥1 dose of anifrolumab or placebo, of whom 676 were IFNGS high. Over 52 weeks, higher average anifrolumab serum concentrations were associated with increased median 21 IFNGS neutralization, which was rapid and sustained with anifrolumab 300 mg (>80%, Weeks 12-52), lower and delayed with anifrolumab 150 mg (>50%, Week 52), and minimal with placebo. The proportion of patients with Week 24 anifrolumab trough concentration ($C_{trough}$) exceeding the $IC_{80}$ (3.88 µg/mL) was greater with anifrolumab 300 mg versus anifrolumab 150 mg (~83% vs ~27%), owing to the higher estimated median $C_{trough}$ (15.6 vs 0.2 µg/mL). BICLA response rates increased with 21 IFNGS neutralization; more patients had a BICLA response in the highest versus lowest neutralization quartiles at Week 52 (58.1% vs 37.6%). In conclusion, anifrolumab IV 300 mg Q4W rapidly, substantially, and sustainably neutralized the 21 IFNGS and was associated with clinical efficacy, supporting the 300 mg IV dosing regimen in patients with SLE, and the corresponding 120 mg SC dose.

10.2. Introduction

Systemic lupus erythematosus (SLE) is a chronic autoimmune condition characterized by innate and adaptive immune pathway dysregulation, hyperinflammatory signaling cascades, and immune deposits in tissues, which can cause irreversible damage to vital organs. The type I interferon (IFN) signaling pathway plays an instrumental role in SLE pathogenesis. All 5 classes of type I IFNs (α, β, ε, κ, ω) activate the type I IFN-α receptor (IFNAR), which mediates downstream signaling to stimulate IFN-regulated gene transcription, measured using the IFN gene signature (IFNGS). An elevated type I IFNGS in blood or tissues occurs in 50%-80% of patients with SLE and is associated with increased disease activity. [10-13]IFNGS-high patients have more active SLE disease with higher levels of anti-double-stranded DNA (anti-dsDNA) antibodies versus IFNGS-low patients.

Anifrolumab is a human, immunoglobulin G1K ($IgG1_K$) monoclonal antibody that binds the type I IFNAR subunit 1 (IFNAR1) with high affinity and specificity, sterically inhibiting the formation of the functional IFNAR complex. The subsequent antibody-receptor complex is internalized rapidly, preventing IFNAR1-mediated signaling in response to all classes of type I IFNs.

In the randomized, placebo-controlled, 52-week phase 3 TULIP-1 and TULIP-2 trials in patients with moderate to severe SLE despite standard therapy, intravenous anifrolumab 300 mg every 4 weeks (Q4W) for 48 weeks was well tolerated and more efficacious than placebo across a range of clinical endpoints, including British Isles Lupus Assessment Group (BILAG)-based Composite Lupus Assessment (BICLA) responses, skin responses, oral glucocorticoid dosage reductions, and flare rates. In line with the proposed mechanism of action, anifrolumab 300 mg elicited substantial (median >85%) pharmacodynamic (PD) neutralization of the 21-gene type I IFNGS (21-IFNGS) in IFNGS-high patients, which was attained as early as Week 4 and sustained through Week 52.

In an analysis of anifrolumab pharmacokinetic (PK) exposure across 5 clinical trials, the median anifrolumab serum concentrations with anifrolumab 300 mg Q4W were consistent throughout the 52-week treatment period (across trials and within each trial), with few patients having trough concentrations ($C_{trough}$) below the limit of quantification. High IFNGS expression was associated with lower systemic anifrolumab exposure, as the median time to elimination was shorter in IFNGS-high patients than in IFNGS-low patients (57 vs 67 days). Anifrolumab PK concentrations were also inversely associated with body weight, but were not impacted by other covariates examined (race, age, sex, renal and hepatic function, immunogenicity, and use of common SLE medications).

Higher anifrolumab dosages were associated with greater PD neutralization in patients with systemic sclerosis and SLE; however, the PK/PD relationship and PD/efficacy relationships, and whether these were impacted by disease characteristics, remained to be characterized fully. Here, we aimed to confirm that the intravenous anifrolumab 300 mg Q4W dosing regimen, which is the proposed recommended dosage, provides adequate PK exposure and PD neutralization in IFNGS-high patients with SLE. PD neutralization was quantified as the change from baseline 21-IFNGS score; therefore, we did not include IFNGS-low patients in our analyses, as their baseline 21-IFNGS expression would be insufficient to observe meaningful PD neutralization. To investigate PK and PD in IFNGS-high patients, we evaluated how varying serum anifrolumab exposure influences PD neutralization of the 21-IFNGS and how 21-IFNGS neutralization, in turn, is associated with clinical efficacy, using data pooled from the TULIP-1 and TULIP-2 trials.

10.3. Methods 10.3.1. Study Design

For this analysis, data were pooled from the randomized, double-blind, parallel-group, placebo-controlled, 52-week phase 3 TULIP-1 (NCT02446912) and TULIP-2 (NCT02446899) trials (FIG. 1).

10.3.2. Patients

The TULIP-1 and TULIP-2 trials enrolled adults (18-70 years) who fulfilled the American College of Rheumatology classification criteria for SLE. All patients had moderate to severe SLE, defined as a SLEDAI-2K score ≥6 (excluding points attributed to fever, lupus-related headache, or organic brain syndrome) and a clinical (not including laboratory results) SLEDAI-2K score ≥4. At screening, patients were seropositive for antinuclear antibodies, anti-dsDNA antibodies, and/or anti-Smith antibodies, and were receiving at least one stable standard therapy treatment. At screening, patients were classified as 4-gene type I IFNGS high or low by a central laboratory using an analytically validated 4-gene (IFI27, IFI44, IFI44L, and RSAD2) quantitative polymerase chain reaction (qPCR)-based test from patients' whole blood.

10.3.3. Efficacy Endpoints

The TULIP-1 and TULIP-2 trials both assessed the proportion of patients in the anifrolumab 300 mg group versus the placebo group with a BICLA response at Week 52 (primary endpoint in TULIP-2, secondary endpoint in TULIP-1) or an SLE Responder Index of ≥4 (SRI[4]) response at Week 52 (primary endpoint in TULIP-1, secondary endpoint in TULIP-2). The percentages of patients who were classified as BICLA or SRI(4) responders, the differences between anifrolumab and placebo groups, and the associated 95% confidence intervals (CIs) were adjusted for the stratification factors, with the use of a Cochran-Mantel-Haenszel method.

A BICLA response was defined as all of the following: reduction of all baseline BILAG-2004 A and B domain scores to B/C/D and C/D, respectively, and no worsening in other BILAG-2004 organ systems; no increase in SLEDAI-2K score (from baseline); no increase in Physician's Global Assessment (PGA) score (≥0.3 points from baseline); no study treatment discontinuation; and no use of restricted medications.

An SRI(4) response was defined as all of the following: ≥4-point reduction in SLEDAI-2K; <1 new BILAG-2004 A or <2 new BILAG-2004 B organ domain scores; no increase in PGA score (≥0.3 points from baseline); no study treatment discontinuation; and no use of restricted medications.

10.3.4. PK Measures and Modeling

The PK analysis dataset included all patients who received anifrolumab 150 mg or anifrolumab 300 mg who had at least one quantifiable serum PK observation post-first dose. PK measurements were taken at pre-dose Weeks 0, 12, 24, 36, and 48, post-dose 15±5 minutes after the end of infusion at Weeks 0 and 48, and the final anifrolumab PK measurement was taken at Week 52. Anifrolumab concentrations were determined using an electrochemiluminescence assay on the Meso Scale Discovery (MSD®) platform (Meso Scale Diagnostics, Rockville, MD, USA). The assay measurement range was 20 to 1280 ng mL$^{-1}$ for human serum diluted 1:10, with a lower limit of quantitation of 20 ng mL$^{-1}$. The population PK model that was developed for SLE was used to estimate predicted anifrolumab concentrations at specified timepoints (for example, the Week 24 anifrolumab trough concentration [$C_{trough}$]) and the predicted average anifrolumab concentrations over the treatment duration ($C_{ave}$), as described previously.

10.3.5. PD Measures

PD was measured using the 21-IFNGS assay consisting of 21 type I IFN-α/β-inducible genes (FIG. 28), which included the 4 genes in the dichotomous IFNGS test, as described previously [24,25]. The PD measurement taken at baseline was expressed as the median fold-change in 21-IFNGS score relative to the pooled healthy control sample from 30 healthy volunteers. PD was also measured at Weeks 12, 24, 36, and 52, where median PD neutralization was expressed as the median percentage change from baseline in 21-IFNGS +/− median absolute deviation (MAD). All PD analyses excluded 25 patients who were missing the baseline PD measurement.

10.3.6. PK/PD Analysis

IFNGS-low patients have baseline 21-IFNGS scores similar to healthy subjects, which would be insufficient to observe meaningful PD neutralization; therefore, IFNGS-low patients were not included in the PK/PD or PD/efficacy analyses.

10.3.6.1. Graphic PK/PD Analysis

The graphic PK/PD analysis included IFNGS-high patients who had at least one PD measurement before discontinuation for all treatment groups, as well as at least one quantifiable serum PK observation in the anifrolumab 150 mg and 300 mg groups. Patients who were treated with anifrolumab were categorized depending on the individual predicted average anifrolumab concentration over treatment duration ($C_{ave}$) medians or tertiles (depending on the sample size) for anifrolumab 150 mg or anifrolumab 300 mg, respectively. Median 21-IFNGS PD neutralization over the 52-week treatment period was compared across $C_{ave}$ subgroups.

10.3.6.2. PK/PD Modeling

The PK/PD modeling analysis population included IFNGS-high patients with baseline and at least one post-baseline PD measurement before discontinuation in all groups, as well as at least one quantifiable serum PK observation in the anifrolumab groups. The relationship between anifrolumab exposure (PK) and PD neutralization of the 21-IFNGS was described by an indirect response model in which the type I IFN-inducible gene production is inhibited by anifrolumab. The model was a nonlinear mixed-effects model first developed to describe the PK/PD relationship of anifrolumab in patients with systemic sclerosis. The model schematic is shown in FIG. 16. The PK/PD model was implemented in the software NONMEM® (version 7.3 or higher, ICON Development Solutions, Ellicott City, MD; 2006) to provide the PK/PD parameter estimates. Visual predictive checks were conducted to ensure observed data were adequately captured by the 95% prediction interval, which was generated based on 5000 model simulations.

10.3.7. PD/Efficacy Analysis

The PD/efficacy analysis included IFNGS-high patients with a baseline and at least one post-baseline PD assessment before discontinuation. Individual median 21-IFNGS neutralization from baseline to steady-state levels were computed over Weeks 12, 24, 36, and 52, based on observed data pooled from the anifrolumab 150-mg and 300-mg treatment groups, excluding PD measurements collected after discontinuation. Patients in the pooled anifrolumab 150-mg and 300-mg treatment groups were categorized into subgroups depending on median percent 21-IFNGS neutralization quartiles. BICLA and SRI(4) response rates at Week 52 were computed for the quartile subgroups, as well as overall in the placebo treatment group.

10.4. Results

10.4.1. Demographics and Baseline Characteristics by IFNGS

There were 819 patients who received at least one dose of anifrolumab 300 mg, anifrolumab 150 mg, or placebo in the TULIP-1 and TULIP-2 trials; 676 (82.5%) and 143 (17.5%) were 4-gene type I IFNGS high and IFNGS low, respectively. As the 4 genes of the dichotomous 4-gene IFNGS test are a subset of the continuous 21-IFNGS,[19, 27] the 4-gene IFNGS status (high versus low) was strongly correlated with median 21-IFNGS score, which was 15.1 in IFNGS-high patients and 1.1 in IFNGS-low patients (Table 10-1, FIG. 17).

IFNGS-high (72.6% vs 88.5%-90.9%). The proportion of patients who were IFNGS-high was higher in Black/African American patients (86.1%) and Asian patients (95.2%) than in White patients (78.3%), which was driven by North America.

TABLE 10-1

Pooled Characteristics of IFNGS-high and IFNGS-low Patients at Baseline and Throughout the TULIP-1 and TULIP-2 Trials

| Characteristics | IFNGS high (n = 676) | IFNGS low (n = 143) |
|---|---|---|
| Baseline Demographic | | |
| Median 21-IFNGS score (IQR) (n = 794)[a] | 15.1 (8.8, 22.4) | 1.1 (0.8, 1.6) |
| Female, n (%) | 625 (92.5) | 135 (94.4) |
| Median age (IQR), years | 40 (32, 49) | 46 (37, 55) |
| Median body weight (IQR), kg | 67.6 (58.0, 82.3) | 77 (64.8, 94.7) |
| Proportion of IFNGS-High Patients by Geographic Region, n (%)[b] | | |
| Asia Pacific (n = 77) | 70 (90.9) | 7 (9.1) |
| Europe (n = 270) | 239 (88.5) | 31 (11.5) |
| Latin America (n = 129) | 115 (89.1) | 14 (10.9) |
| North America (n = 318) | 231 (72.6) | 87 (27.4) |
| Rest of world (n = 25) | 21 (84.0) | 4 (16.0) |
| Proportion of IFNGS-High Patients by Race, n (%)[b] | | |
| White (n = 543) | 425 (78.3) | 118 (21.7) |
| Black/African American (n = 108) | 93 (86.1) | 15 (13.9) |
| Asian (n = 84) | 80 (95.2) | 4 (4.8) |
| Other or missing data (n = 84) | 78 (92.9) | 6 (7.1) |
| Baseline Disease Characteristic | | |
| SLEDAI-2K score ≥10, n (%) | 486 (71.9) | 90 (62.9) |
| Mean BILAG-2004 global score (SD) | 18.9 (5.5) | 19.6 (5.4) |
| Mean CLASI activity score (SD) | 8.3 (7.7) | 6.8 (5.2) |
| Mean oral glucocorticoid dosage, mg day$^{-1}$ (SD) | 10.2 (9.4) | 6.4 (6.3) |
| Anti-dsDNA | | |
| Seropositive, n (%)[c] | 329 (48.7) | 37 (25.9) |
| Median (IQR), U mL$^{-1}$ | 14.0 (2.4, 53.5) | 2.4 (0.3, 15.6) |
| Abnormal C3, n (%)[d] | 282 (41.7) | 19 (13.3) |
| Abnormal C4, n (%)[d] | 182 (26.9) | 8 (5.6) |
| Characteristic During 52-Week Double-Blind Period | | |
| Discontinuation before Week 52, n/N (%)[e] — Placebo | 75/302 (24.8) | 15/64 (23.4) |
| Anifrolumab 150 mg | 14/76 (18.4) | 4/17 (23.5) |
| Anifrolumab 300 mg | 55/298 (18.5) | 7/62 (11.3) |
| Restricted medication use, n/N (%)[f] — Placebo | 103/302 (34.1) | 12/64 (18.8) |
| Anifrolumab 150 mg | 17/76 (22.4) | 4/17 (23.5) |
| Anifrolumab 300 mg | 63/298 (21.1) | 13/62 (21.0) |

Anti-dsDNA, anti-double-stranded DNA; BILAG-2004, British Isles Lupus Assessment Group-2004; C3, complement 3; C4, complement 4; CLASI, Cutaneous Lupus Erythematosus Disease Area and Severity Index; IFNGS, interferon gene signature; IQR, interquartile range; SD, standard deviation; SLEDAI-2K, Systemic Lupus Erythematosus Disease Activity Index 2000.
Table includes all patients who received at least one dose of anifrolumab 300 mg, anifrolumab 150 mg, or placebo in the TULIP-1 and TULIP-2 trials.
[a]21-IFNGS score was calculated as the expression relative to 30 pooled healthy control samples. There were 25 patients (18 IFNGS high and 7 IFNGS low) who were missing baseline 21-IFNGS score.
[b]Percentage displayed is the percentage of patients who were IFNGS high or low in each geographic region or race group including patients treated with anifrolumab 150 mg, anifrolumab 300 mg, or placebo from TULIP-1 and TULIP-2.
[c]Anti-dsDNA antibody levels were classified as positive (>15 U mL$^{-1}$) or negative (≤15 U mL$^{-1}$) and were measured in a central laboratory using an automated fluoroimmunoassay.
[d]Complement levels were classified as abnormal (C3 < 0.9 g L$^{-1}$; C4 < 0.1 g L$^{-1}$) or normal (C3 ≥ 0.9 g L$^{-1}$; C4 ≥ 0.1 g L$^{-1}$) and were measured in a central laboratory.
[e]Discontinuation rates are displayed as the number of patients who discontinued (n) over the number of patients in each treatment subgroup (N).
[f]Rates of restricted medication use are displayed as the number of patients who used any medication beyond the protocol-permitted allowances (n), over the number of patients in each treatment subgroup (N).

Baseline characteristics for type I IFNGS-high and IFNGS-low patients are displayed in Table 10-1. IFNGS-high patients were younger than IFNGS-low patients (median age 40 vs 46 years). The negative association between age and IFNGS expression was observed for both the dichotomous IFNGS test at screening and median 21-IFNGS score at baseline (FIG. 18). Compared with other geographic regions, patients in North America were slightly older (median age 44 vs 40-41 years) and slightly less likely to be IFNGS-high patients had more severe disease than IFNGS-low patients; at baseline, there were higher rates of anti-dsDNA seropositivity (48.7% vs 25.9%), abnormal C3 (41.7% vs 13.3%), and abnormal C4 (26.9% vs 5.6%), and more patients with SLEDAI-2K score ≥10 (71.9% vs 62.9%) (Table 10-1). The association between disease severity and IFNGS was also reflected in the placebo group, with higher proportions of IFNGS-high patients using medications restricted by the TULIP-1 and TULIP-2 protocols 16,17 than IFNGS-low patients (34.1% vs 18.8%); in contrast, IFNGS-high patients receiving anifrolumab 300 mg had similar restricted medication usage to IFNGS-low patients by Week 52 (~21%).

10.4.2. PK/PD Analysis

The IFNGS-low subgroup had baseline 21-IFNGS scores similar to healthy subjects, which was insufficient to observe meaningful PD neutralization; thus, the median percent neutralization of the 21-IFNGS over time was minimal with both anifrolumab 300 mg and placebo in IFNGS-low patients (FIG. 19). Therefore, IFNGS-low patients were not included in the PK/PD or PD/efficacy analyses.

TABLE 10-2

Anifrolumab Cave Subgroup Thresholds for the Graphical PK/PD Analysis

| $C_{ave}$ (µg mL$^{-1}$) | | TULIP-1 | TULIP-2 |
|---|---|---|---|
| Anifrolumab 300 mg Q4W | T1 | <32.0 | <32.4 |
| | T2 | 32-<44.3 | 32.4-<47.9 |
| | T3 | ≥44.3 | ≥47.9 |
| Anifrolumab 150 mg Q4W | M1 | ≤11.5 | — |
| | M2 | >11.5 | — |

$C_{ave}$, average anifrolumab concentration over treatment duration; M, median; PD, pharmacodynamic; PK, pharmacokinetic; T, tertile.

In contrast, in IFNGS-high patients treated with anifrolumab 300 mg, PD neutralization of the 21-IFNGS occurred across all baseline 21-IFNGS groups. However, patients in the lowest baseline 21-IFNGS quartile (who had baseline 21-IFNGS that was closest to that observed in IFNGS-low patients), had lower PD neutralization with larger variability than patients in higher baseline 21-IFNGS quartiles (FIG. 20).

10.4.2.1. PK/PD Graphic Analysis

The PK/PD graphic analysis included 357 IFNGS-high patients from TULIP-1, who received placebo (n=144), anifrolumab 150 mg (n=72), or anifrolumab 300 mg (n=141), and 297 IFNGS-high patients from TULIP-2, who received placebo (n=149) or anifrolumab 300 mg (n=148) (FIG. 21).

Patients treated with anifrolumab 300 mg were categorized by $C_{ave}$ tertiles, which were generally consistent across TULIP-1 and TULIP-2. Patients treated with anifrolumab 150 mg were split into subgroups depending on $C_{ave}$ values above or below the median (11.5 µg mL$^{-1}$), owing to smaller sample sizes. Patients treated with anifrolumab 300 mg generally had higher $C_{ave}$ values than those treated with anifrolumab 150 mg, and there was minimal overlap in the observed $C_{ave}$ values between groups, owing to nonlinearity of PK exposure, as reported previously (Table 10-2).

All anifrolumab 300-mg $C_{ave}$ tertiles reached a median PD neutralization ~80% that was sustained from Week 12 through Week 52; however, the variability was greater in the lowest $C_{ave}$ tertile versus the two higher $C_{ave}$ tertiles across both trials (FIG. 21A, FIG. 21B). The two highest $C_{ave}$ tertiles had median PD neutralizations that plateaued at ~90%. Substantial and sustained PD neutralization with anifrolumab 300 mg was observed consistently across baseline disease activity subgroups, including subgroups based on SLEDAI-2K score (<10 vs ≥10), oral glucocorticoid dosage (<10 vs ≥10 mg day$^{-1}$), and lupus serologies (anti-dsDNA antibodies, C3, and C4) (FIG. 22). In contrast, in the subgroup of patients treated with anifrolumab 150 mg who had $C_{ave}$ values below the median, PD neutralization was highly variable (large MAD values), although it was numerically greater than the minimal PD neutralization observed with placebo.

10.4.2.2. PK/PD Modeling Analysis

The PK/PD modeling analysis included 646 IFNGS-high patients from the pooled TULIP-1 and TULIP-2 trials who received placebo (n=289), anifrolumab 150 mg (n=70), or anifrolumab 300 mg (n=287). The PK/PD indirect response model adequately captured the observed data by the 95% prediction interval as demonstrated by visual predictive checks (FIG. 23). The NONMEM® output diagnostic plot is shown in FIG. 25A-D. The PK/PD model parameter estimates are shown in Table 10-3.

The $IC_{80}$ was defined as the approximate anifrolumab concentration required to produce 80% of the maximum inhibition of the 21-IFNGS expression relative to baseline. The model gave an $IC_{80}$ estimate of 3.88 µg mL$^{-1}$, which was based on the $IC_{50}$ estimate of 6.56 nM and the anifrolumab molecular weight of 148 kDa. The estimated median Week 24 $C_{trough}$ was higher with anifrolumab 300 mg than with anifrolumab 150 mg (15.6 vs 0.2 µg mL$^{-1}$), owing to nonlinearity (FIG. 24). Thus, the Week 24 $C_{trough}$ exceeded the $IC_{80}$ in a higher proportion of patients treated with anifrolumab 300 mg vs 150 mg (~83% vs ~27%). The model-estimated baseline 21-IFNGS score was 13.1 for IFNGS-high patients (Table 10-3).

TABLE 10-3

PK/PD Model Estimated Parameters for Anifrolumab

| Parameter | Parameter Estimates | Standard Error |
|---|---|---|
| $I_{max}$ | 0.94 | 0.00355 |
| $IC_{50}$ (nM) | 6.56 | 0.90 |
| Baseline type I IFN 21-gene fold-change, $GS_0$ | 13.1 | 0.395 |
| $K_{out}$ (d$^{-1}$) | 0.746 | 0.479 |
| Var ($\eta_{IC50}$) | 2.80 | 0.381 |
| Var ($\eta_{GS0}$) | 0.466 | 0.0309 |
| $\sigma^2$ | 0.182 | 0.00617 |

$GS_0$, baseline gene signature; $IC_{50}$, potency, the approximate anifrolumab concentration required to produce 50% of the maximum inhibition of the 21-IFNGS expression relative to baseline; IFN, interferon; $I_{max}$, the approximate anifrolumab concentration required to produce the maximal inhibition of the 21-IFNGS expression relative to baseline; $k_{out}$, elimination rate constant; PD, pharmacodynamic; PK, pharmacokinetic; Var ($\eta_{IC50}$), inter-subject variability of $IC_{50}$; Var($\eta_{GS0}$), inter-subject variability of $GS_0$; $\sigma^2$, residual variability.

10.4.3. PD Neutralization in Pooled Anifrolumab 150 mg and 300 mg Groups

The 341 IFNGS-high patients who received anifrolumab 150 mg or 300 mg were categorized depending on PD neutralization quartiles (Q1 <51.7%, Q2 ≥51.7%-85.3%, Q3 ≥85.3%-92.6%, Q4 ≥92.6%). Patients in the anifrolumab 300 mg group resided predominantly in the higher PD neutralization quartiles (Q2-Q4); the median PD neutralization from Week 12 to Week 52 was >86% with anifrolumab 300 mg versus <37% with anifrolumab 150 mg.

Of the 273 IFNGS-high patients from the anifrolumab 300 mg group included in the PD neutralization analysis, 41 (15.0%) were in lowest quartile of PD neutralization (<51.7% neutralization). Of these 41 patients, 18 (43.9%) had baseline 21-IFNGS scores in the bottom quartile (Q1 <3.8), which were associated with lower PD neutralization (FIG. 20). The remaining 23 patients tended to have low PK exposures; 19 were in the lowest anifrolumab 300 mg PK $C_{ave}$ quartile ($C_{ave}$ <27.6 µg mL$^{-1}$) and 4 were in the second quartile (27.6-39.2 µg mL$^{-1}$) (pooled TULIP-1 and TULIP-2 anifrolumab 300 mg PK $C_{ave}$ quartiles are shown in Table 10-4). Compared with the total IFNGS-high population (n=676), these 23 patients tended to have more active baseline disease, with numerically higher proportions of patients with anti-dsDNA antibody positivity (56.2% vs 48.7%), low C3 (56.5% vs 41.7%), low C4 (47.8% vs 26.9%), SLEDAI-2K scores ≥10 (78.2% vs 71.9%), or higher oral glucocorticoid dosages (12.4 vs 10.2 mg day$^{-1}$).

TABLE 10-4

Cave PK Quartiles for Anifrolumab 300 mg in Pooled TULIP-1 and TULIP-2 Data

| $C_{ave}$ (µg mL$^{-1}$) | | Pooled TULIP-1 and TULIP-2 |
|---|---|---|
| Anifrolumab 300 mg Q4W | Q1 | <27.6 |
| | Q2 | 27.6-<39.2 |
| | Q3 | 39.2-<49.8 |
| | Q4 | ≥49.8 |

$C_{ave}$, average anifrolumab concentration over treatment duration; M, median; PK, pharmacokinetic; Q, quartile; Q4W, every 4 weeks.
Quartiles for average PK concentrations are based on patients in pooled data from TULIP-1 and TULIP-2 who were treated with anifrolumab 300 mg and who completed treatment.

10.4.4. PD/Efficacy Analysis

The PD/efficacy analysis included the 341 IFNGS-high patients who received anifrolumab 150 mg or 300 mg and 280 patients who received placebo. The PD/efficacy analysis is displayed in FIG. 26A and FIG. 26B. The proportions of patients with BICLA responses at Week 52 increased with higher PD neutralization in the anifrolumab group (Q1 37.6%, Q2 49.4%, Q3 51.8%, Q4 58.1%); response rates in all anifrolumab quartiles were numerically greater than placebo (30%). Similarly, the proportions of patients with SRI(4) responses at Week 52 increased with PD neutralization subgroups in the anifrolumab group (Q1 48.2%, Q2 56.5%, Q3 58.8%, Q4 64.0%); response rates in all anifrolumab quartiles were numerically greater than placebo (40%).

The inventors next investigated whether there was an association between BICLA response rates at Week 52 and 21-IFNGS score at baseline. In the anifrolumab 300 mg group, BICLA response rates at Week 52 were numerically greater in patients who had a high baseline 21-IFNGS score (Q4 ≥20.7) compared with those who had a low 21-IFNGS score (Q1 <3.8) (TULIP-1: 54% vs 40%; TULIP-2: 47% vs 43%). However, BICLA responses were higher with anifrolumab 300 mg versus placebo across all baseline 21-IFNGS score quartiles in TULIP-1 and TULIP-2 (FIG. 27).

10.5. Discussion

Correlating drug concentrations, pharmacodynamics, and efficacy can provide important insights into the relationship between a drug's mechanism of action and clinical response. In this analysis, the inventors evaluated pooled data from the phase 3 TULIP-1 and TULIP-2 trials of patients with moderate to severe SLE to examine the PK/PD and PD/efficacy relationships of anifrolumab. This study identified an association between anifrolumab serum concentrations and PD neutralization of type I IFN-inducible genes (21-IFNGS), which in turn was associated with improved efficacy at Week 52 in patients who were IFNGS high at screening. The findings support the mechanism of action of anifrolumab; namely, measures of disease activity and clinical efficacy were improved by blocking the type I IFN pathway and inhibiting the downstream expression of genes that propagate SLE disease activity and drive lupus pathogenesis.

In IFNGS-low patients at screening, PD neutralization was not meaningful, and thus only IFNGS-high patients were included in the analysis. Also, it was important to consider IFNGS-high patients specifically, as these patients have higher clearance of anifrolumab than IFNGS-low patients. Elevated IFNGS expression is associated with more active, treatment-resistant disease, increased serum concentrations of IFN-α, as well as serum markers of inflammation and immune dysregulation, including tumor necrosis factor, IL-2, IFN-γ, and IL-1R2. Consistently, it was found that, relative to IFNGS-low patients, IFNGS-high patients had higher baseline disease activity, with more patients seropositive for anti-dsDNA antibodies or with abnormal C3/C4 at baseline. In the placebo group, IFNGS-high patients were more likely to use restricted medications throughout the trial than IFNGS-low patients. Treatment with anifrolumab 300 mg, however, was associated with a reduction in restricted medication usage in IFNGS-high patients to a usage similar to that observed in IFNGS-low patients. The rate of treatment discontinuation was lower with anifrolumab 300 mg than with placebo in both IFNGS-high and IFNGS-low patients.

The PK/PD model, the IFNAR1 internalization kinetics, and information from SLE studies, appeared robust because estimates aligned with observed data. The model-predicted parameters were indicative of a strong PK/PD relationship. A predicted ~83% of patients in the anifrolumab 300 mg group had an anifrolumab trough concentration that could elicit >80% inhibition of 21-IFNGS expression. Indeed, a rapid (by Week 12), substantial (~80%), and sustained (through Week 52) neutralization of the 21-IFNGS was observed across all anifrolumab 300-mg $C_{ave}$ tertiles. In contrast, only a predicted ~27% of patients in the anifrolumab 150 mg group had an anifrolumab trough concentration that could elicit >80% inhibition of the 21-IFNGS. Thus, a lower, more variable, and delayed PD neutralization was observed with anifrolumab 150 mg, especially in patients with $C_{ave}$ below the median, where PD neutralization was minimal and similar to that observed with placebo. Lower anifrolumab serum exposure resulted in more variable PD neutralization profiles across trials and dosing regimens.

A small subset (15%) of IFNGS-high patients in the anifrolumab 300 mg group did not experience high PD neutralization throughout the trial (median percentage neutralization of baseline 21-IFNGS was less than 51.7%). Nearly half of these patients had baseline 21-IFNGS scores in the bottom quartile, despite being assigned IFNGS-high status, owing to the dichotomous nature of the 4-gene IFNGS test, and therefore did not need high PD neutralization to obtain 21-IFNGS scores similar to healthy controls. The other half of these patients had low PK exposures, supporting the PK/PD relationship, and tended to have numerically higher disease activity at baseline. However, baseline disease activity measures did not appear to impact PD neutralization with anifrolumab 300 mg in the overall pooled population, further supporting anifrolumab IV 300 mg dosing regimen, and the corresponding 120 mg subcutaneous dose, across patient subgroups, regardless of disease activity.

Consequently, it might be suggested that a subset of patients with low PD neutralization might benefit from a dosage of anifrolumab higher than 300 mg; however, there is no evidence to suggest that BICLA response rates would have been higher at doses greater than IV 300 mg. For example, in the phase 2 MUSE study, BICLA response rates at Week 52 were higher with anifrolumab 300 mg (53.3%) than with anifrolumab 1000 mg (41.2%). Furthermore, in an analysis that modeled the relationship between PK exposure and BICLA response rates in TULIP-1 and TULIP-2, anifrolumab 1000 mg was predicted to provide only incremental benefit over anifrolumab 300 mg owing to nonlinearity.

However, as shown in EXAMPLE 4: Determination of the optimal subcutaneous unit dose, this variability in combination with the variability in bioavailability justifies a surprisingly high subcutaneous dose of more than 105 mg.

PD neutralization of the 21-IFNGS was associated with improved clinical efficacy. All anifrolumab PD neutralization quartiles had numerically greater proportions of BICLA and SRI(4) responders than the placebo group. However, the highest anifrolumab PD neutralization quartile had ~21% and ~16% higher absolute rates of BICLA and SRI(4) responses, respectively, than the lowest anifrolumab PD neutralization quartile (made up predominantly of patients in the anifrolumab 150 mg group). These results are consistent with analyses of the association between PK and efficacy in the TULIP-1 and TULIP-2 trials, which identified an exposure-efficacy relationship and demonstrated that all anifrolumab PK subgroups had greater BICLA/SRI(4) response rates than the placebo group.

Early changes in PD markers that associate with clinical efficacy at later time points are clinically valuable. This study suggests that the degree of IFNGS neutralization can be used as an established PD marker in the design of future anifrolumab trials investigating different populations (such as pediatric patients or other lupus populations, such as those with lupus nephritis (LN) or cutaneous lupus erythematosus (CLE)) or different methods of administration, such as subcutaneous injections.

Anifrolumab IV 300 mg every 4 weeks was selected as the optimal dosing regimen in patients with moderate to severe SLE because of its favorable benefit-risk profile in the phase 2 MUSE trial. The $C_{ave}$ with anifrolumab 300 mg was consistent across studies and was higher than the concentration elicited by anifrolumab 150 mg, with small overlap between subgroups, in line with the nonlinear PK profile of anifrolumab. Anifrolumab steady-state concentrations, quantified with Week 24 trough concentrations, were predicted to be ~80-fold higher with anifrolumab 300 mg than with anifrolumab 150 mg.

10.6. Conclusion

Here, the inventors elucidated a clear relationship between anifrolumab serum exposure and PD neutralization in patients with moderate to severe SLE despite standard therapy, providing evidence to support the anifrolumab IV 300 mg Q4W dosing regimen and the anifrolumab SC 120 mg QW dosing regimen. Indeed, anifrolumab 300 mg provided IFNGS-high patients with adequate PK exposure to result in rapid, substantial, and sustained neutralization of the 21-IFNGS, which, in turn, was associated with improved clinical efficacy. The same clinical efficacy is thus expected for an anifrolumab SC dose of greater than 105 mg, e.g. 120 mg, QW.

11. EXAMPLE: 7: TREATMENT OF TYPE I IFN DISEASE 11.1. Type I IFN Signature

To understand the relationship between type I IFN expression and response to anti-IFN therapy, it is necessary to know if a subject's disease is driven by type I IFN activation. However, direct measurement of type I IFN remains a challenge. As such, a transcript-based marker was developed to evaluate the effect of over expression of the target protein on a specific set of mRNA markers. The expression of these markers is easily detected in whole blood, for example using PCR (e.g. TaqMan™) assays.

The expression of the genes may be measured by RT-PCR. Suitable primers and probes for detection of the genes may be found in WO2011028933. A suitable kit for measuring gene expression for the IFNGS test is the QIAGEN Therascreen® IFIGx RGQ RT-PCR kit (IFIGx kit), as described in Brohawn et al. [26], which is incorporated herein by reference in its entirety. The 21-IFNGS assay consists of 21 type I IFN-α/β-inducible genes (FIG. 28), which includes the 4 genes in the dichotomous IFNGS test, as described previously [24,25].

The bimodal distribution of the transcript scores for SLE subjects supports defining an IFN test high and low subpopulation (using the 4-gene IFN test) (FIG. 29A). The type I IFN test is described in WO2011028933 A1, which is incorporated herein by reference in its entirety. The type I IFN gene signature may be used to identify a subject has a type I IFN gene signature (IFNGS)-test high patient or an IFNGS-test low patient (FIG. 29B). The 4-gene IFNGS test measures expression of the genes IFI27, IFI44, IFI44L, and RSAD2 compared with 3 reference genes; 18S, ACTB and GAPDH in the whole blood of the subject. The result of the test is a score that is compared with a pre-established cut-off that classifies patients into 2 groups with low or high levels of IFN inducible gene expression (FIG. 29B).

The type I IFN gene score demonstrates a correlation with expression in diseased tissue such as skin in SLE. Particularly, high type I IFN gene signature is associated with increased disease activity and OCS use in SLE (FIG. 29C).

The IFNGS can be used to identify other type I IFN mediated diseases suitable for treatment with an IFNAR1 inhibitor. Type I IFN mediated diseases include lupus nephritis (LN) and Sjogren's syndrome, wherein patients may be identified as having an elevated IFNGS (FIG. 31A and FIG. 31B). A similar core type I IFN signature (5-gene score) is activated in SSc and myositis patients (FIG. 32).

11.2. Lupus

The IFNGS (21-gene) in lupus (SLE) is neutralized by an inhibitor of type I IFN signaling, e.g. the anti-IFNα antibody sifalimumab (FIG. 30A), or the type I IFN receptor (IFNAR1) inhibitor anifrolumab (FIG. 30B). See also Section 10.

11.3. Scleroderma

Systemic sclerosis (scleroderma, SSc) is a rare autoimmune disease characterized by chronic immune activation and excessive deposition of extracellular matrix components. A Phase 1, dose-escalation trial (Study CP180) investigated the safety and tolerability of anifrolumab in subjects with SSc (FIG. 33). The IFNGS score in SSc patients was determined to be a median fold change (FC) of 5 IFN-inducible genes, which were among the highest differentially regulated genes in scleroderma patients compared to healthy control. The 5 genes are a subset of the 21-gene IFNGS.

The 5-gene IFNGS is elevated in the whole blood (WB) of Scleroderma patients as measured using the 5-gene signature (IFI27, RSAD2, IFI44, IFI44L, IFI6) (FIG. 31B). The 5-gene IFNGS score in SSc patients is comparable to the 5-gene IFNGS in SLE patients (FIG. 32A, FIG. 34A). Baseline IFN signatures are highly correlated between affected tissues and periphery and with baseline disease activity (FIG. 34B). There is also a positive correlation between baseline the 5-gene IFNGS score and SSc disease activity (FIG. 34C), as measured by modified Rodnan skin score (mRTSS).

5-gene IFNGS may be neutralized in scleroderma (SSc) patients (FIG. 35A), as described in WO 2013/188494 (incorporated herein by reference in its entirety). In particular, in study CP180 (NCT0093082), about 2/3 SSc patients are type I IFN signature positive at baseline. Following treatment with anifrolumab, there was a quick and close to complete suppression of the IFNGS (day 1) at 1 mg/kg (mpk) dose or above (both single and multi-dose) (FIG. 35B) with a clear dose-dependent effect on the time the signature remained inhibited before recovery (FIG. 35B and FIG. 35C). The IFN score used for study CP180, which is similar to what has been used in other autoimmune indications, was confirmed to be a sensitive PD marker relevant to treatment with an inhibitor of type I IFN mediated signaling in SSc.

Anifrolumab treatment of SSc patients also suppressed T cell activation (via lowered CXCL10 and CD40L) (FIG. 36). Anifrolumab further suppressed markers of collagen formation and upregulated markers of collagen degradation (FIG. 36), suggesting a mechanism of action through which inhibition of type I IFN signaling in SSc patients modulates tissue is modulated. There was further improvement in skin scores (mRSS at the highest dose).

In summary, treatment of scleroderma patients with anifrolumab shows near complete suppression of the type I IFN score in WB and skin in a dose-dependent manner. The core IFNGS is elevated in SSc patients, and treatment with anifrolumab neutralities this gene signature. Anifrolumab has also been shown to have a treatment effect in SSc patients. Anifrolumab is therefore expected to have a similar treatment effect in SSc patients as SLE and LN patients, at a similar or the same dose of anifrolumab as has been shown to be safe and efficacious in SLE, i.e. 300 mg IV Q4W or the equivalent SC dose of more than 105 mg and less than 150 mg QW, particularly 120 mg SC QW.

11.4. Myositis

The presence of type I IFN in myositis muscle biopsy was first observed by immunohistochemical studies [27], followed by reports that PDCs are increased in dermatomyositis (DM) muscle and skin biopsies [28,29]. The onset of DM or polymyositis (PM) has been observed to occur after IFN-α or IFN-β therapy, suggesting type I IFN as a potential target for treatment in these two indications [30,31]. IFN-β and not IFN-α transcripts were over-expressed in PM as well as dermatomyositis/JDM7. IFNβ is elevated in the blood of DM patients and correlates with type I IFN-inducible genes in the blood [32]. Gene expression profiling analysis of muscle biopsies from myositis patients has shown that the most over-expressed transcripts in DM patients compared to normal controls are IFN-α/β-inducible genes [28].

There is an overexpression of type I IFN-inducible genes (136 genes) in the blood of patients with dermatomyositis (DM) or polymyositis (PM) compared to healthy volunteers (define as a value of <4) [11], and particularly IFI44L and RSAD2. Greenberg et al. identified a 13 type I IFN signature PD marker or elevated IFI27, RSAD2, IFI44L, IFI44, OAS1, IFIT1, ISG15, OAS3, HERC5, MX1, ESPTI1, IFIT3 and IFI6 expression compared to healthy donors [11]. In study MI-CP151 (NCT00533091), patient blood and muscle biopsy specimens were collected. Baseline type I IFN gene signature (4-gene and 13-gene score) values for DM and PM patients in muscle and blood were determined, revealing elevated IFNGS score in the whole blood and muscle of both BM and PM patients (FIG. 37, FIG. 31A, FIG. 38) [10]. See also WO 2009/011770 and WO 2009/011770, both of which are incorporated herein by reference.

An inhibitor of type I IFN gene signaling (sifalimumab) neutralized the 13-gene IFNGS score in blood and muscle of DM and PM patients, in a dose dependent manner (Study MI-CP151, FIG. 39). In particular, the type I IFN gene signature was maximally neutralized at a median of 91% in the 0.3 mg/kg cohort, with an average neutralization across sifalimumab-treated cohorts of 47%, 33%, and 65% observed at days 28, 56, and 98, respectively. At day 98, the four sifalimumab-treated cohorts showed a median neutralization of the gene signature ranging from 54%-91%. Treatment of myositis patients with sifalimumab showed up to 80% of neutralization of the type I IFN signature in the muscle (FIG. 38). More IFNGS suppression was observed in a dose dependent manner in all 4 sifalimumab dose groups (0.3, 1.0, 3.0 and 10 mg·kg) vs the placebo group. IFN α inhibition reduced immune cell infiltration into myositis muscle (DM and PM) (FIG. 41). Sifalimumab suppressed pathways downstream of type I IFN in muscle from myositis patients and target neutralization correlated with muscle function (MMT8) improvement in myositis patient [10,11] (FIG. 42). Therefore, importantly, target modulation of the type I IFN gene signature in blood showed a correlative trend with disease activity in DM or PM patients (FIG. 40A). Furthermore, target suppression of the type I IFN gene signature was correlated with suppression of important disease related signaling events in muscle tissue (FIG. 40B).

In summary, the core IFNGS is elevated in myositis patients, and treatment with sifalimumab neutralities this gene signature. The IFNGS signature data therefore plausibly suggest that IFN pathway activation is within a similar range for myositis as SLE. A similar IFN activation is observed across SLE, DM and PM (FIG. 32). Furthermore, general receptor availability is the overriding driver for dose selection in myositis due to the ubiquitous nature of the type I IFN receptor. The data show that there is a similar PF/PD available across disease states (e.g. comparing SLE and SSc). Furthermore, the subcutaneous dose data available from Study 06 and 08 support the selection of a dose of about 120 mg SC QW in myositis. Anifrolumab completely suppressed the type I IFN signaling through the IFNAR, while sifalimumab only targets the majority of IFN-α (FIG. 43). Anifrolumab is therefore expected to have a similar neutralising effect on the IFNGS in myositis patients as sifalimumab, at a similar or the same dose of anifrolumab as has been shown to be safe and efficacious in SLE, i.e. 300 mg IV Q4W or the equivalent SC dose of more than 105 mg and less than 150 mg QW, particularly 120 mg SC QW.

12. EXAMPLE 8: INJECTION DEVICE

Anifrolumab is administered by an injection device [1] [9] such as a prefilled syringe (PFS) (FIG. 44A) or an autoinjector (AI) (FIG. 44B).

12.1. Autoinjector

Anifrolumab may be administered by an autoinjector [1]. The autoinjector is shown in exploded view (FIG. 45A) and in an assembled form (FIG. 45B). A label [4] is wrapped around and attached to the autoinjector [1] (FIG. 45C). The autoinjector has an autoinjector housing [3], cap and cap remover [2] and drive unit [5]. The liquid anifrolumab formulation unit dose [6] is contained in the autoinjector housing [3]. The unit dose [6] can be viewed through the viewing window [7].

12.1.1.1. Accessorized Pre-Frilled Syringe

Anifrolumab may be administered by accessorized pre-filled syringe (APFS) [8]. The APFS [8] includes the unit dose of anifrolumab [6] contained in a primary container [9] shown in an assembled state in FIG. 46A and in an exploded view in FIG. 46B. The primary container [9] has a plunger stopper [16]. The primary container has a nominal fill volume of 0.8 ml but may contain slightly more than 0.8 ml. The remainder of the space in the primary container [9] is taken up by an air bubble [18]. The air bubble may have a size of 3-5 mm, optionally, 4 mm. The primary container [9] has a defined stopper position [19].

The accessorized pre-filled syringe (APFS) primary container [9] is provided in a PFS assembly [8] including a needle guard [12], a finger flange and a plunger rod [13]. A label is provided with the primary container [9] in the PFS assembly [8]. The label is wrapped around the syringe [9] in the label placement position [15].

12.1.1.2. Packaging

The injection device [1] [8] is provided in a kit (FIG. 47). A label [4] is provided with the APFS or autoinjector in the packaging. The label includes instruction for the use of the injection device [1], [8]. The packaging includes a tamper seal.

REFERENCES

All publications mentioned in the specification and/or referenced below are herein incorporated by reference.

[1] M. R. Turner and S. V. Balu-Iyer, J. Pharm. Sci. 107, 1247 (2018).
[2] B. Bittner, W. Richter, and J. Schmidt, Biodrugs 32, 425 (2018).
[3] J. Witcher et al., Br. J. Clin. Pharmacol. 81, 908 (2016).
[4] D. A. Isenberg et al., Ann. Rheum. Dis. 75, 323 (2016).
[5] J. T. Merrill et al., Ann. Rheum. Dis. 75, 332 (2016).
[6] G. T. Ferguson et al., J. Asthma Allergy 11, 63 (2018).
[7] M. Khamashta et al., Ann. Rheum. Dis. 75, 1909 (2016).
[8] R. Tummala et al., Lupus Sci. Med. 5, e000252 (2018).
[9] A. Psarras, P. Emery, and E. M. Vital, Rheumatol. Oxf. Engl. 56, 1662 (2017).
[10] B. W. Higgs et al., Ann. Rheum. Dis. 73, 256 (2014).
[11] S. A. Greenberg et al., Genes Immun. 13, 207 (2012).
[12] J. C. Hall and A. Rosen, Nat. Rev. Rheumatol. 6, 40 (2010).
[13] L. Bolko et al., Brain Pathol. Zurich Switz. 31, e12955 (2021).
[14] A.-K. Somani et al., Arch. Dermatol. 144, 1341 (2008).
[15] B. Skaug and S. Assassi, Cytokine 132, 154635 (2020).
[16] B. W. Higgs et al., Ann. Rheum. Dis. 70, 2029 (2011).
[17] X. Liu et al., Arthritis Rheum. 65, 226 (2013).
[18] X. Guo et al., J. Invest. Dermatol. 135, 2402 (2015).
[19] R. Furie et al., Arthritis Rheumatol. Hoboken Nj 69, 376 (2017).
[20] R. A. Furie et al., Lancet Rheumatol. 1, e208 (2019).
[21] E. F. Morand et al., N. Engl. J. Med. 382, 211 (2020).
[22] Y. Tanaka and R. Tummala, Mod. Rheumatol. 0, 1 (2020).
[23] I. N. Bruce et al., Lancet Rheumatol. 0, (2020).
[24] Y. Yao et al., Arthritis Rheum. 60, 1785 (2009).
[25] Y. Yao et al., Hum. Genomics Proteomics HGP 2009, (2009).
[26] ACR Meeting Abstracts (n.d.).
[27] D. A. Isenberg et al., Clin. Exp. Immunol. 63, 450 (1986).
[28] S. A. Greenberg et al., Neurology 65, 1782 (2005).
[29] J. Wenzel et al., Clin. Exp. Dermatol. 31, 576 (2006).
[30] L. Dietrich, A. Bridges, and M. Albertini, Med. Oncol. 17, 64 (2000).
[31] C. Gota and L. Calabrese, Autoimmunity 36, 511 (2003).
[32] A. P. Liao et al., Ann. Rheum. Dis. 70, 831 (2011).

The invention claimed is:

1. A method of treating type I interferon (IFN)-mediated disease in a subject comprising subcutaneously administering a unit dose comprising 120 mg to 135 mg of a type I interferon (IFN) receptor (IFNAR1) inhibitor, wherein the IFNAR1 inhibitor is anifrolumab and wherein the unit dose is for subcutaneous injection once per week (QW) to the subject in need thereof.

2. The method of claim 1, wherein the disease is an autoimmune disease.

3. The method of claim 2, wherein the disease is lupus.

4. The method of claim 3, wherein the disease is systemic lupus erythematosus (SLE).

5. The method of claim 4, wherein the disease is moderate to severe, active autoantibody-positive SLE.

6. The method of claim 3, wherein the disease is lupus nephritis (LN).

7. The method of claim 3, wherein the disease is cutaneous lupus erythematosus (CLE).

8. The method of claim 2, wherein the disease is myositis.

9. The method of claim 2, wherein the disease is scleroderma.

10. The method of claim 1, wherein the unit dose comprises 120 mg of anifrolumab.

* * * * *

```
SEQUENCE LISTING

Sequence total quantity: 24
SEQ ID NO: 1              moltype = AA  length = 117
FEATURE                   Location/Qualifiers
source                    1..117
                          mol_type = protein
                          note = Anifrolumab VH
                          organism = synthetic construct
SEQUENCE: 1
EVQLVQSGAE VKKPGESLKI SCKGSGYIFT NYWIAWVRQM PGKGLESMGI IYPGDSDIRY    60
SPSFQGQVTI SADKSITTAY LQWSSLKASD TAMYYCARHD IEGFDYWGRG TLVTVSS     117

SEQ ID NO: 2              moltype = AA  length = 108
FEATURE                   Location/Qualifiers
source                    1..108
                          mol_type = protein
                          note = Anifrolumab VL
                          organism = synthetic construct
SEQUENCE: 2
EIVLTQSPGT LSLSPGERAT LSCRASQSVS SSFFAWYQQK PGQAPRLLIY GASSRATGIP    60
DRLSGSGSGT DFTLTITRLE PEDFAVYYCQ QYDSSAITFG QGTRLEIK               108

SEQ ID NO: 3              moltype = AA  length = 5
FEATURE                   Location/Qualifiers
source                    1..5
                          mol_type = protein
                          note = HCDR1
                          organism = synthetic construct
SEQUENCE: 3
NYWIA                                                                 5

SEQ ID NO: 4              moltype = AA  length = 17
FEATURE                   Location/Qualifiers
source                    1..17
                          mol_type = protein
                          note = HCDR2
                          organism = synthetic construct
SEQUENCE: 4
```

```
IIYPGDSDIR YSPSFQG                                                          17

SEQ ID NO: 5              moltype = AA  length = 8
FEATURE                   Location/Qualifiers
source                    1..8
                          mol_type = protein
                          note = HCDR3
                          organism = synthetic construct
SEQUENCE: 5
HDIEGFDY                                                                     8

SEQ ID NO: 6              moltype = AA  length = 12
FEATURE                   Location/Qualifiers
source                    1..12
                          mol_type = protein
                          note = LCDR1
                          organism = synthetic construct
SEQUENCE: 6
RASQSVSSSF FA                                                               12

SEQ ID NO: 7              moltype = AA  length = 7
FEATURE                   Location/Qualifiers
source                    1..7
                          mol_type = protein
                          note = LCDR2
                          organism = synthetic construct
SEQUENCE: 7
GASSRAT                                                                      7

SEQ ID NO: 8              moltype = AA  length = 9
FEATURE                   Location/Qualifiers
source                    1..9
                          mol_type = protein
                          note = LCDR3
                          organism = synthetic construct
SEQUENCE: 8
QQYDSSAIT                                                                    9

SEQ ID NO: 9              moltype = AA  length = 107
FEATURE                   Location/Qualifiers
source                    1..107
                          mol_type = protein
                          note = Light chain constant region
                          organism = synthetic construct
SEQUENCE: 9
RTVAAPSVFI FPPSDEQLKS GTASVVCLLN NFYPREAKVQ WKVDNALQSG NSQESVTEQD           60
SKDSTYSLSS TLTLSKADYE KHKVYACEVT HQGLSSPVTK SFNRGEC                        107

SEQ ID NO: 10             moltype = AA  length = 330
FEATURE                   Location/Qualifiers
source                    1..330
                          mol_type = protein
                          note = Heavy chain constant region
                          organism = synthetic construct
SEQUENCE: 10
ASTKGPSVFP LAPSSKSTSG GTAALGCLVK DYFPEPVTVS WNSGALTSGV HTFPAVLQSS           60
GLYSLSSVVT VPSSSLGTQT YICNVNHKPS NTKVDKRVEP KSCDKTHTCP PCPAPEFEGG          120
PSVFLFPPKP KDTLMISRTP EVTCVVVDVS HEDPEVKFNW YVDGVEVHNA KTKPREEQYN          180
STYRVVSVLT VLHQDWLNGK EYKCKVSNKA LPASIEKTIS KAKGQPREPQ VYTLPPSREE          240
MTKNQVSLTC LVKGFYPSDI AVEWESNGQP ENNYKTTPPV LDSDGSFFLY SKLTVDKSRW          300
QQGNVFSCSV MHEALHNHYT QKSLSLSPGK                                           330

SEQ ID NO: 11             moltype = AA  length = 440
FEATURE                   Location/Qualifiers
source                    1..440
                          mol_type = protein
                          note = Heavy chain
                          organism = synthetic construct
SEQUENCE: 11
EVQLVQSGAE VKKPGESLKI SCKGSGYIFT NYWIAWVRQM PGKGLESMGI IYPGDSDIRY           60
SPSFQGQVTI SADKSITTAY LQWSSLKASD TAMYYCARHD IEGFDYWGRG TLVTVSSAST          120
KGPSVFPLAP SSKSTSGGTA ALGCLVKDYF PEPVTVSWNS GALTSGVHTF PAVLQSSGLY          180
SLSSVVTVPS SSLGTQTYIC NVNHKPSNTK VDKRVEPKSC DKTHTCPPCP APEFEGGPSV          240
FLFPPKPKDT LMISRTPEVT CVVVDVSHED PEVKFNWYVD GVEVHNAKTK PREEQYNSTY          300
RVVSVLTVLH QDWLNGKEYK CKVSNKALPA SIEKTISKAK GQPREPQVYT LPPSREEMTK          360
NQVSLTCLVK GFYPSDIAVE WESNGQPENN YKTTPPVLDS DGSFFLYSKL TVDKSRWQQG          420
NVFSCSVMHE ALHNHYTQKS                                                      440

SEQ ID NO: 12             moltype = AA  length = 215
```

```
FEATURE                 Location/Qualifiers
source                  1..215
                        mol_type = protein
                        note = Light chain
                        organism = synthetic construct
SEQUENCE: 12
EIVLTQSPGT LSLSPGERAT LSCRASQSVS SSFFAWYQQK PGQAPRLLIY GASSRATGIP      60
DRLSGSGSGT DFTLTITRLE PEDFAVYYCQ QYDSSAITFG QGTRLEIKRT VAAPSVFIFP     120
PSDEQLKSGT ASVVCLLNNF YPREAKVQWK VDNALQSGNS QESVTEQDSK DSTYSLSSTL     180
TLSKADYEKH KVYACEVTHQ GLSSPVTKSF NRGEC                                215

SEQ ID NO: 13           moltype = AA  length = 80
FEATURE                 Location/Qualifiers
source                  1..80
                        mol_type = protein
                        note = H15D10 (VH)
                        organism = synthetic construct
SEQUENCE: 13
EVQLVQSGAE VKKPGESLRI SCKGSGYTFT NYWVAWVRQM PGKGLESMGI IYPGDSDTRY      60
SPSFQGHVTI SADKSISTAY                                                  80

SEQ ID NO: 14           moltype = AA  length = 108
FEATURE                 Location/Qualifiers
source                  1..108
                        mol_type = protein
                        note = L8C3 (VL)
                        organism = synthetic construct
SEQUENCE: 14
DIQMTQSPSS LSASLGDRVT ITCRASQNVG NYLNWYQQKP GKAPKLLIYR ASNLASGVPS      60
RFSGSGSGTD FTLTISSLQP EDFATYYCQQ MEHAPPTFGQ GTKVEIKR                  108

SEQ ID NO: 15           moltype = AA  length = 108
FEATURE                 Location/Qualifiers
source                  1..108
                        mol_type = protein
                        note = L16C11 (VL)
                        organism = synthetic construct
SEQUENCE: 15
EIVLTQSPGT LSLSPGERAT LSCRASQSVI GYYLAWYQQK PGQAPRLLIY SVSTLASGIP      60
DRFSGSGSGT DFTLTISRLE PEDFAVYYCQ QYYRFPITFG QGTKVEIK                  108

SEQ ID NO: 16           moltype = AA  length = 117
FEATURE                 Location/Qualifiers
source                  1..117
                        mol_type = protein
                        note = H19B7 (VH)
                        organism = synthetic construct
SEQUENCE: 16
EVQLVQSGAE VKKPGESLRI SCKGSGYTFT NYWMAWVRQM PGKGLESMGI IYPSDSDTRY      60
SPSFQGHVTI SADKSISTAY LQWSSLKASD TAMYYCARHD VEGYDYWGQG TLVTVSS        117

SEQ ID NO: 17           moltype = AA  length = 119
FEATURE                 Location/Qualifiers
source                  1..119
                        mol_type = protein
                        note = QX006N (VH)
                        organism = synthetic construct
SEQUENCE: 17
EVQLVESGGG LVQPGGSLRL SCAASGFSLS SYYMTWVRQA PGKGLEWVSV INVYGGTYYA      60
SWAKGRFTIS RDNSKNTLYL QMNSLRAEDT AVYYCAREDV AVYMAIDLWG QGTLVTVSS      119

SEQ ID NO: 18           moltype = AA  length = 111
FEATURE                 Location/Qualifiers
source                  1..111
                        mol_type = protein
                        note = QX006N (VL)
                        organism = synthetic construct
SEQUENCE: 18
AIQMTQSPSS LSASVGDRVT ITCQASQSIS NQLSWYQQKP GKAPKLLIYD ASSLASGVPS      60
RFSGSRSGTK FTLTISSLQP EDFATYYCLG IYGDGADDGI AFGGGTKVEI K              111

SEQ ID NO: 19           moltype = AA  length = 5
FEATURE                 Location/Qualifiers
source                  1..5
                        mol_type = protein
                        note = QX006N (HCDR1)
                        organism = synthetic construct
SEQUENCE: 19
SYYMT                                                                   5
```

```
SEQ ID NO: 20           moltype = AA  length = 16
FEATURE                 Location/Qualifiers
source                  1..16
                        mol_type = protein
                        note = QX006N (HCDR2)
                        organism = synthetic construct
SEQUENCE: 20
VINVYGGTYY ASWAKG                                                          16

SEQ ID NO: 21           moltype = AA  length = 11
FEATURE                 Location/Qualifiers
source                  1..11
                        mol_type = protein
                        note = QX006N (HCDR3)
                        organism = synthetic construct
SEQUENCE: 21
EDVAVYMAID L                                                               11

SEQ ID NO: 22           moltype = AA  length = 11
FEATURE                 Location/Qualifiers
source                  1..11
                        mol_type = protein
                        note = QX006N (LCDR1)
                        organism = synthetic construct
SEQUENCE: 22
QASQSISNQL S                                                               11

SEQ ID NO: 23           moltype = AA  length = 7
FEATURE                 Location/Qualifiers
source                  1..7
                        mol_type = protein
                        note = QX006N (LCDR2)
                        organism = synthetic construct
SEQUENCE: 23
DASSLAS                                                                     7

SEQ ID NO: 24           moltype = AA  length = 13
FEATURE                 Location/Qualifiers
source                  1..13
                        mol_type = protein
                        note = QX006N (LCDR3)
                        organism = synthetic construct
SEQUENCE: 24
LGIYGDGADD GIA                                                             13
```